United States Patent
Tobata et al.

(10) Patent No.: US 9,611,429 B2
(45) Date of Patent: *Apr. 4, 2017

(54) LIQUID CRYSTAL MEDIUM, OPTICAL DEVICE AND LIQUID CRYSTAL COMPOUND

(71) Applicants: JNC CORPORATION, Tokyo (JP); JNC PETROCHEMICAL CORPORATION, Tokyo (JP)

(72) Inventors: Hitoshi Tobata, Chiba (JP); Koki Sago, Chiba (JP); Shin-Ichi Yamamoto, Chiba (JP); Yasuhiro Haseba, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/893,073

(22) PCT Filed: May 22, 2014

(86) PCT No.: PCT/JP2014/063568
§ 371 (c)(1),
(2) Date: Nov. 23, 2015

(87) PCT Pub. No.: WO2014/192627
PCT Pub. Date: Dec. 4, 2014

(65) Prior Publication Data
US 2016/0122648 A1    May 5, 2016

(30) Foreign Application Priority Data
May 27, 2013   (JP) ................. 2013-110788

(51) Int. Cl.
| | |
|---|---|
| *G02F 1/1333* | (2006.01) |
| *C09K 19/34* | (2006.01) |
| *C07D 319/06* | (2006.01) |
| *C09K 19/20* | (2006.01) |
| *C09K 19/58* | (2006.01) |
| *C09K 19/12* | (2006.01) |
| *C09K 19/38* | (2006.01) |
| *C09K 19/56* | (2006.01) |

(Continued)

(52) U.S. Cl.
CPC ........ *C09K 19/3402* (2013.01); *C07D 319/06* (2013.01); *C09K 19/12* (2013.01); *C09K 19/20* (2013.01); *C09K 19/3444* (2013.01); *C09K 19/3447* (2013.01); *C09K 19/3458* (2013.01); *C09K 19/38* (2013.01); *C09K 19/56* (2013.01); *C09K 19/586* (2013.01); *C09K 19/588* (2013.01); *G02F 1/137* (2013.01); *C09K 2019/0466* (2013.01); *C09K 2019/122* (2013.01); *C09K 2019/123* (2013.01); *C09K 2019/124* (2013.01); *C09K 2019/3422* (2013.01); *G02F 2001/13793* (2013.01)

(58) Field of Classification Search
CPC   C09K 19/3402; C09K 19/3447; C09K 19/20; C09K 19/3458; C09K 19/586; C09K 19/588; C09K 19/12; C09K 19/3444; C09K 19/38; C09K 19/56; C09K 2019/0466; C09K 2019/3422; C09K 2019/122–2019/124; G02F 1/137; G02F 1/1333; C07D 319/06
USPC .................. 252/299.01, 299.6; 349/182
See application file for complete search history.

(56) References Cited

U.S. PATENT DOCUMENTS

| | | | |
|---|---|---|---|
| 6,329,027 B1 | 12/2001 | Kondo et al. | |
| 8,409,673 B2 * | 4/2013 | Haseba .............. | C09K 19/20 252/299.61 |

(Continued)

FOREIGN PATENT DOCUMENTS

| | | |
|---|---|---|
| EP | 1690917 | 8/2006 |
| JP | 2003-327966 | 11/2003 |

(Continued)

OTHER PUBLICATIONS

Kikuchi et al., "Polymer-stabilised liquid crystal blue phases", Nature Materials, 1, pp. 64-68, Sep. 2002.

(Continued)

*Primary Examiner* — Geraldina Visconti
(74) *Attorney, Agent, or Firm* — Jianq Chyun IP Office

(57) ABSTRACT

A liquid crystal medium has stability to heat, light and so forth, and significantly high dielectric anisotropy, and develops an optically isotropic liquid crystal phase. Moreover, various kinds of optical devices can be used in a wide temperature range and have a short response time, a large contrast ratio and low driving voltage.

A liquid crystal composition contains achiral component T containing at least one compound 1 represented by formula (1) and a chiral agent, and develops the optically isotropic liquid crystal phase.

(1)

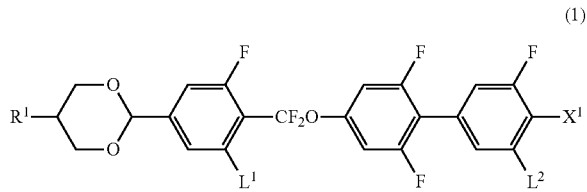

In formula (1), for examples, $R^1$ is alkyl, $L^1$ and $L^2$ are each independently fluorine or hydrogen, and $X^1$ is halogen.

17 Claims, 1 Drawing Sheet

(51) Int. Cl.
*C09K 19/04* (2006.01)
*G02F 1/137* (2006.01)

(56) References Cited

U.S. PATENT DOCUMENTS

| | | | |
|---|---|---|---|
| 8,858,830 B2 * | 10/2014 | Yamamoto | C09K 19/3402 252/299.01 |
| 9,175,222 B2 * | 11/2015 | Sago | C09K 19/3402 |
| 2006/0006363 A1 | 1/2006 | Heckmeier et al. | |
| 2006/0050354 A1 | 3/2006 | Heckmeier et al. | |
| 2006/0227283 A1 | 10/2006 | Ooi et al. | |
| 2008/0259254 A1 | 10/2008 | Kikuchi et al. | |
| 2011/0242473 A1 | 10/2011 | Haseba et al. | |
| 2012/0099039 A1 | 4/2012 | Haseba et al. | |
| 2013/0100369 A1 | 4/2013 | Sagou et al. | |
| 2013/0306908 A1 | 11/2013 | Jansen et al. | |
| 2014/0339471 A1 | 11/2014 | Hattori et al. | |
| 2015/0240159 A1 * | 8/2015 | Yamamoto | C09K 19/20 349/86 |
| 2015/0291548 A1 * | 10/2015 | Sago | C07D 319/06 349/139 |

FOREIGN PATENT DOCUMENTS

| | | |
|---|---|---|
| JP | 2005-157109 | 6/2005 |
| JP | 2005-336477 | 12/2005 |
| JP | 2006-506477 | 2/2006 |
| JP | 2006-506515 | 2/2006 |
| JP | 2006-89622 | 4/2006 |
| JP | 2006-127707 | 5/2006 |
| JP | 2006-225655 | 8/2006 |
| JP | 2006-299084 | 11/2006 |
| WO | 98/23561 | 6/1998 |
| WO | 2005/080529 | 9/2005 |
| WO | 2005/090520 | 9/2005 |
| WO | 2006/063662 | 6/2006 |
| WO | 2010/058681 | 5/2010 |
| WO | 2010/134430 | 11/2010 |
| WO | 2011/162142 | 12/2011 |
| WO | 2012/100809 | 8/2012 |
| WO | 2013/039051 | 3/2013 |

OTHER PUBLICATIONS

Hisakado et al., "Large Electro-optic Kerr Effect in Polymer-Stabilized Liquid Crystalline Blue Phases", Advance Materials, 17(1), pp. 96-98, Jan. 2005.

Haseba et al., "Electro-optic effects of the optically isotropic state induced by the incorporative effects of a polymer network and the chirality of liquid crystal", Journal of the SID, 14(6), pp. 551-556, Jun. 2006.

International Search Report (Form PCT/ISA/210), mailed on Aug. 19, 2014, with English translation thereof, pp. 1-4.

* cited by examiner

LIQUID CRYSTAL MEDIUM, OPTICAL DEVICE AND LIQUID CRYSTAL COMPOUND

CROSS-REFERENCE TO RELATED APPLICATION

This application is a 371 application of an international PCT application serial no. PCT/JP2014/063568, filed on May 22, 2014, which claims the priority benefit of Japan application no. 2013-110788, filed on May 27, 2013. The entirety of each of the abovementioned patent applications is hereby incorporated by reference herein and made a part of this specification.

TECHNICAL FIELD

The present invention relates to a liquid crystal compound useful as a material for an optical device, a liquid crystal composition, and the optical device using the liquid crystal composition, for example.

BACKGROUND ART

A liquid crystal display device using a liquid crystal composition is widely utilized for a display of a watch, a calculator, a word processor or the like. The liquid crystal display devices utilize refractive index anisotropy, dielectric anisotropy or the like of a liquid crystal compound. As an operating mode in the liquid crystal display device, a mode mainly using at least one polarizer to display an image is known, such as a phase change (PC), twisted nematic (TN), super twisted nematic (STN), bistable twisted nematic (BTN), electrically controlled birefringence (ECB), optically compensated bend (OCB), in-plane switching (IPS), or vertical alignment (VA) mode. Further, a research has been recently conducted actively into a mode for developing electric birefringence by applying an electric field in an optically isotropic liquid crystal phase (Patent literature Nos. 1 to 17, Non-patent literature Nos. 1 to 3).

Further, a proposal has been made for a wavelength variable filter, a wavefront control device, a liquid crystal lens, an aberration correction device, an aperture control device, an optical head device, or the like utilizing the electric birefringence in a blue phase as one of the isotropic liquid crystal phases (Patent literature Nos. 10 to 12).

A classification based on a driving mode in the device includes a passive matrix (PM) and an active matrix (AM). The passive matrix (PM) is further classified into static, multiplex and so forth, and the AM is further classified into a thin film transistor (TFT), a metal insulator metal (MIM) and so forth according to a kind of a switching device.

Meanwhile, Patent literature No. 15 describes a composition that contains compound (R-3) described below and develops the optically isotropic liquid crystal phase is described in, and Patent literature No. 16 describes a composition that contains compounds (R-1) to (R-3) and develops the optically isotropic liquid crystal phase.

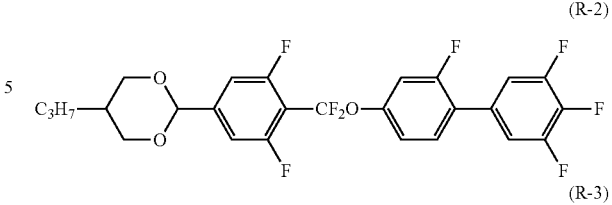
(R-1)

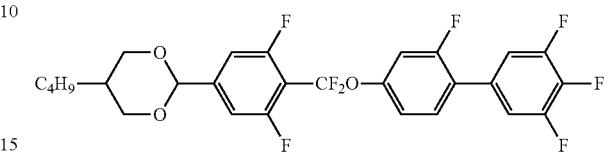
(R-2)

(R-3)
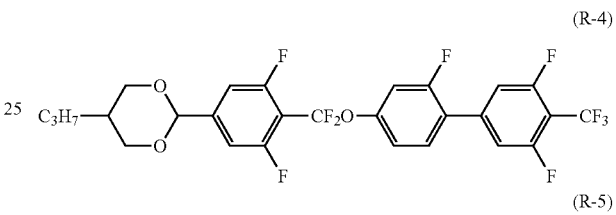

Moreover, Patent literature No. 17 describes compounds (R-4) and (R-5) described below.

(R-4)

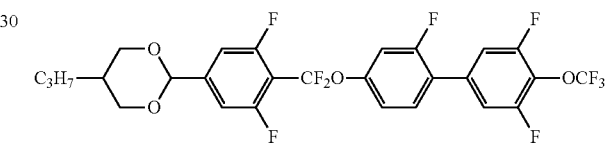

(R-5)

CITATION LIST

Patent Literature

Patent literature No. 1: JP 2003-327966 A.
Patent literature No. 2: WO 2005/90520 A.
Patent literature No. 3: JP 2005-336477 A.
Patent literature No. 4: JP 2006-89622 A.
Patent literature No. 5: JP 2006-299084 A.
Patent literature No. 6: JP 2006-506477 A.
Patent literature No. 7: JP 2006-506515 A.
Patent literature No. 8: WO 2006/063662 A.
Patent literature No. 9: JP 2006-225655 A.
Patent literature No. 10: JP 2005-157109 A.
Patent literature No. 11: WO 2005/80529 A.
Patent literature No. 12: JP 2006-127707 A.
Patent literature No. 13: WO 1998/023561 A.
Patent literature No. 14: WO 2010/058681 A.
Patent literature No. 15: WO 2010/134430 A.
Patent literature No. 16: WO 2011/162142 A.
Patent literature No. 17: WO 2012/100809 A.

Non-Patent Literature

Non-patent literature No. 1: Nature Materials, 1, 64 (2002).
Non-patent literature No. 2: Adv. Mater., 17, 96 (2005).

Non-patent literature No. 3: Journal of the SID, 14, 551 (2006).

SUMMARY OF INVENTION

Technical Problem

Under the situations described above, a liquid crystal medium that has stability to heat, light and so forth, a wide liquid crystal phase temperature range and a significantly large dielectric anisotropy, and develops an optically isotropic liquid crystal phase is required. Moreover, various kinds of optical devices that can be used in a wide temperature range and has a short response time, a large contrast ratio and a low drive voltage are required.

Solution to Problem

The invention provides a liquid crystal compound, a liquid crystal medium (a liquid crystal composition, a polymer/liquid crystal composite material), a mixture of a polymerizable monomer and the liquid crystal compound, an optical device including the liquid crystal medium, and the liquid crystal compound as described below, for example.

The invention provides the compound, the liquid crystal medium (the liquid crystal composition, the polymer/liquid crystal composite), and the optical device including the liquid crystal medium as described below.

Item 1. A liquid crystal composition that contains achiral component T containing at least one compound 1 represented by formula (1), and a chiral agent, and develops an optically isotropic liquid crystal phase:

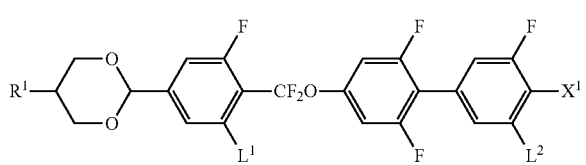
(1)

wherein, in formula (1), $R^1$ is hydrogen or alkyl having 1 to 20 carbons, at least one of —$CH_2$— in the alkyl may be replaced by —O—, —S—, —COO—, —OCO—, —CH=CH—, —CF=CF— or —C≡C—, at least one of hydrogen in the alkyl or in a group in which —$CH_2$— in the alkyl is replaced by —O—, —S—, —COO—, —OCO—, —CH=CH—, —CF=CF— or —C≡C— may be replaced by halogen or alkyl having 1 to 3 carbons; $L^1$ and $L^2$ are each independently fluorine or hydrogen, and $X^1$ is halogen, —$CF_3$, —$OCF_3$, —C≡N or —N=C=S.

Item 2. The liquid crystal composition according to item 1, wherein compound 1 is a compound represented by formula (1-1):

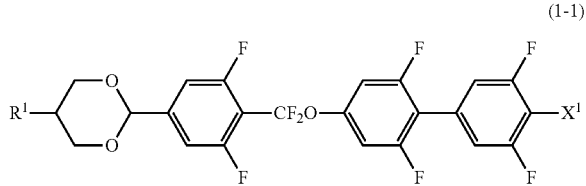
(1-1)

wherein, in formula (1-1), $R^1$ is hydrogen or alkyl having 1 to 20 carbons, at least one of —$CH_2$— in the alkyl may be replaced by —O—, —S—, —COO—, —OCO—, —CH=CH—, —CF=CF— or —C≡C—, at least one of hydrogen in the alkyl or in a group in which —$CH_2$— in the alkyl is replaced by —O—, —S—, —COO—, —OCO—, —CH=CH—, —CF=CF— or —C≡C— may be replaced by halogen or alkyl having 1 to 3 carbons; and $X^1$ is halogen, —$CF_3$, —$OCF_3$, —C≡N or —N=C=S.

Item 3. The liquid crystal composition according to item 1 or 2, wherein, in formula (1) or formula (1-1), $X^1$ is fluorine or —$CF_3$.

Item 4. The liquid crystal composition according to any one of items 1 to 3, further containing at least one compound selected from the group of compound 3 represented by formula (3) and compound 7 represented by formula (7):

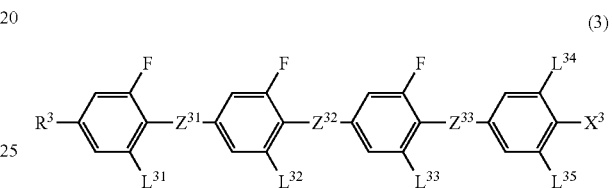
(3)

wherein, in formula (3), $R^3$ is hydrogen or alkyl having 1 to 20 carbons, at least one of —$CH_2$— in the alkyl may be replaced by —O—, —S—, —COO— or —OCO—, at least one of —$CH_2$—$CH_2$— in the alkyl or in a group in which at least one of —$CH_2$— in the alkyl is replaced by —O—, —S—, —COO— or —OCO— may be replaced by —CH=CH—, —CF=CF— or —C≡C—, at least one of hydrogen in the alkyl, in the group in which at least one of —$CH_2$— in the alkyl is replaced by —O—, —S—, —COO— or —OCO—, or in a group in which at least one of —$CH_2$—$CH_2$— in the group in which at least one of —$CH_2$— in the alkyl is replaced by —O—, —S—, —COO— or —OCO— may be replaced by fluorine or chlorine, in which, in $R^3$, neither —O— and —CH=CH— nor —CO— and —CH=CH— are adjacent;

$Z^{31}$, $Z^{32}$ and $Z^{33}$ are each independently a single bond, alkylene having 1 to 4 carbons, and at least one of —$CH_2$— in the alkylene may be replaced by —O—, —COO— or —$CF_2O$—;

$L^{31}$, $L^{32}$, $L^{33}$, $L^{34}$ and $L^{35}$ are each independently hydrogen or fluorine;

$X^3$ is hydrogen, halogen, —$SF_5$ or alkyl having 1 to 10 carbons, at least one of —$CH_2$— in the alkyl may be replaced by —O—, —S—, —COO— or —OCO—, at least one of —$CH_2$—$CH_2$— in the alkyl and in a group in which —$CH_2$— in the alkyl is replaced by —O—, —S—, —COO— or —OCO— may be replaced by —CH=CH—, —CF=CF— or —C≡C—, at least one of hydrogen in the alkyl, in the group in which —$CH_2$— in the alkyl is replaced by —O—, —S—, —COO— or —OCO—, and in a group in which at least one of —$CH_2$—$CH_2$— is replaced by —CH=CH— or —C≡C— may be replaced by fluorine or chlorine, in which, in $X^3$, neither —O— and —CH=CH— nor —CO— and —CH=CH— are adjacent;

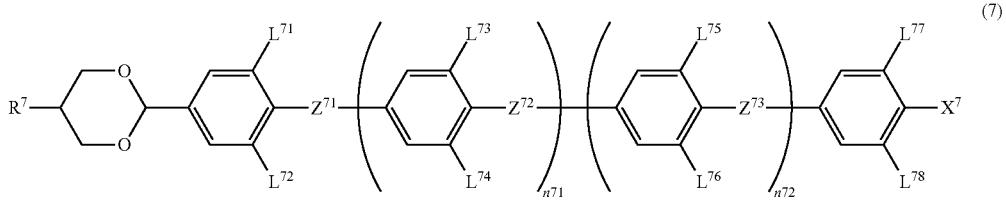

wherein, in formula (7), $R^7$ is alkyl having 1 to 20 carbons, at least one of —CH$_2$— in the alkyl may be replaced by —O—, —S—, —COO— or —OCO—, at least one of —CH$_2$—CH$_2$— in the alkyl may be replaced by —CH=CH—, —CF=CF— or —C≡C—, at least one of hydrogen in the alkyl, in a group in which at least one of —CH$_2$— in the alkyl is replaced by —O—, —S—, —COO— or —OCO—, or in a group in which at least one of —CH$_2$—CH$_2$— in the group in which at least one of —CH$_2$— in the alkyl is replaced by —O—, —S—, —COO— or —OCO— is replaced by —CH=CH— or —C≡C— may be replaced by fluorine or chlorine, in which, in $R^7$, neither —O— and —CH=CH— nor —CO— and —CH=CH— are adjacent;

$L^{71}$, $L^{72}$, $L^{73}$, $L^{74}$, $L^{75}$, $L^{76}$, $L^{77}$ and $L^{78}$ are each independently hydrogen or fluorine;

$Z^{71}$, $Z^{72}$ and $Z^{73}$ are each independently a single bond, —COO— or —CF$_2$O—, but at least one of $Z^{71}$, $Z^{72}$ and $Z^{73}$ is —COO— or —CF$_2$O—;

n71 and n72 are each independently 0 or 1, and satisfies an expression: n71≥n72;

in which, when both $L^{71}$ and $L^{72}$ are fluorine, $Z^{71}$ is —CF$_2$O— and n71 is 1, $L^{74}$ is hydrogen, $X^7$ is hydrogen, halogen, —SF$_5$ or alkyl having 1 to 10 carbons, at least one of —CH$_2$— in the alkyl may be replaced by —O—, —S—, —COO— or —OCO—, at least one of —CH$_2$—CH$_2$— in the alkyl and in a group in which —CH$_2$— in the alkyl is replaced by —O—, —S—, —COO— or —OCO— may be replaced by —CH=CH—, —CF=CF— or —C≡C—, at least one of hydrogen in the alkyl, in the group in which —CH$_2$— in the alkyl is replaced by —O—, —S—, —COO— or —OCO—, or in a group in which at least one of —CH$_2$—CH$_2$— in the alkyl is replaced by —CH=CH— or —C≡C— may be replaced by fluorine or chlorine, in which, in $X^7$, neither —O— and —CH=CH— nor —CO— and —CH=CH— are adjacent.

Item 5. The liquid crystal composition according to any one of items 1 to 4, containing at least one compound selected from the group represented by formulas (1) and (7) in an amount of 1 to 32% by weight based on the total weight of achiral component T.

Item 6. The liquid crystal composition according to items 4 or 5, wherein compound 3 is at least one selected from the group of compounds represented by formula (3-2) and formula (3-3):

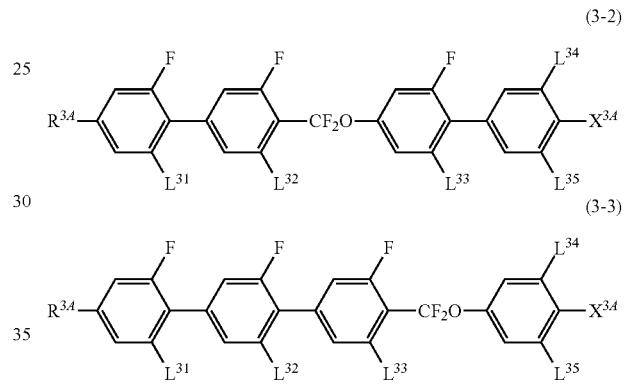

(wherein, $R^{3A}$ is each independently alkyl having 1 to 12 carbons, alkoxy having 1 to 12 carbons, alkenyl having 2 to 12 carbons, or alkenyl having 2 to 12 carbons in which at least one of hydrogen may be replaced by fluorine;

$L^{31}$, $L^{32}$, $L^{33}$, $L^{34}$ and $L^{35}$ are each independently hydrogen or fluorine; and $X^{3A}$ is fluorine, chlorine, —CF$_3$ or —OCF$_3$.)

Item 7. The liquid crystal composition according to item 4 or 5, wherein compound 7 is at least one selected from the group of compounds represented by formulas (7-1) to (7-8):

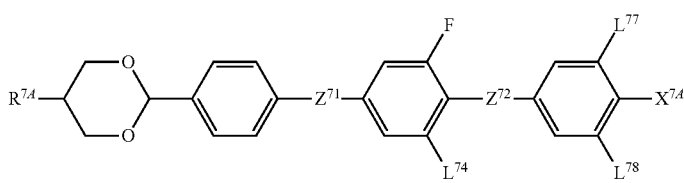

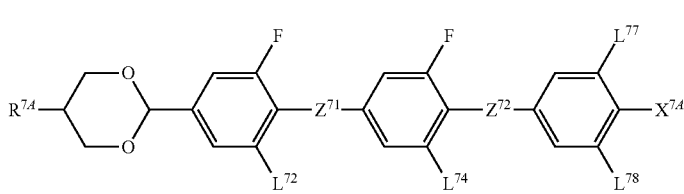

-continued

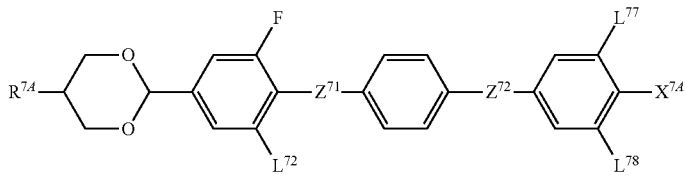
(7-3)

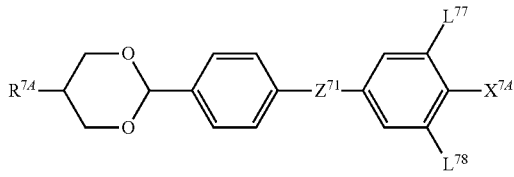
(7-4)

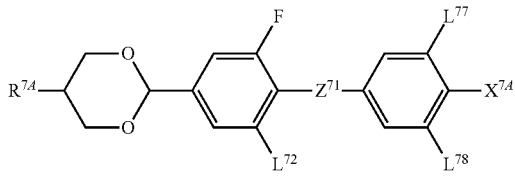
(7-5)

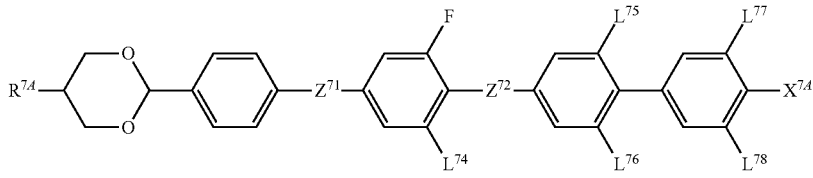
(7-6)

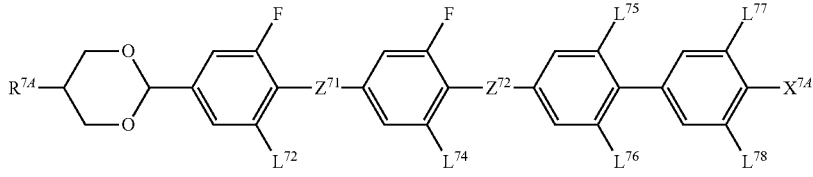
(7-7)

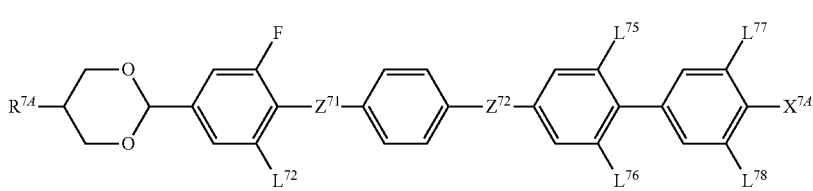
(7-8)

(wherein, $R^{74}$ is hydrogen, alkyl having 1 to 12 carbons, alkoxy having 1 to 11 carbons, alkenyl having 2 to 12 carbons, or alkenyl having 2 to 12 carbons in which at least one of hydrogen is replaced by fluorine;

$L^{72}$, $L^{74}$, $L^{75}$, $L^{76}$, $L^{77}$ and $L^{78}$ are each independently hydrogen or fluorine;

in formulas (7-1) to (7-3) and (7-6) to (7-8), $Z^{71}$ and $Z^{72}$ are each independently a single bond, —COO— or —CF$_2$O—, but at least one of $Z^{71}$ and $Z^{72}$ is —COO— or —CF$_2$O—, in which, in formula (7-3), when both $L^{71}$ and $L^{72}$ are fluorine, $Z^{71}$ is —CF$_2$O— and n71 is 1, $L^{74}$ is hydrogen, and in formulas (7-4) and (7-5), $Z^{71}$ is each independently —COO— or —CF$_2$O—, and $X^{74}$ is fluorine, chlorine, —CF$_3$ or —OCF$_3$.)

Item 8. The liquid crystal composition according to item 4 or 5, wherein compound 7 is at least one selected from the group of compounds represented by formulas (7-2-2-E), (7-2-5-E), (7-2-2-F) and (7-2-5-F):

-continued

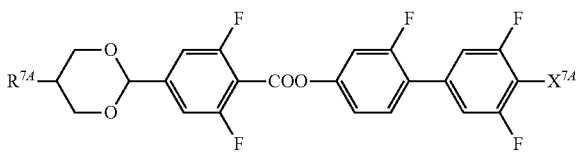
(7-2-5-E)

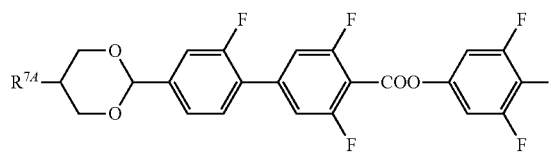
(7-2-2-E)

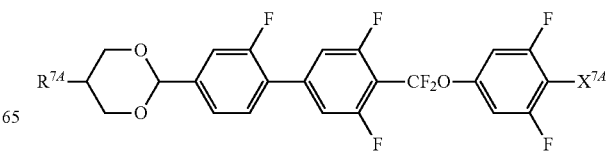
(7-2-2-F)

(7-2-5-F)

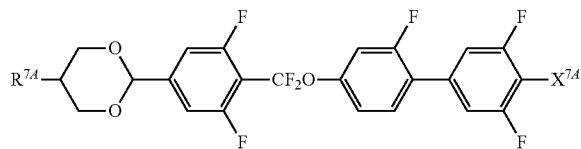

(wherein, $R^{7A}$ is alkyl having 1 to 12 carbons, alkoxy having 1 to 11 carbons, alkenyl having 2 to 12 carbons, or alkenyl having 2 to 12 carbons in which at least one of hydrogen is replaced by fluorine; and $X^{7A}$ is fluorine, chlorine, —CF₃ or —OCF₃.

Item 9. The liquid crystal composition according to any one of items 4 to 8, containing compound 1 in a total amount of 3% by weight to 20% by weight, compound 3 in a total amount of 20% by weight to 80% by weight and compound 7 in a total amount of 10% by weight to 27% by weight, based on the total weight of achiral component T.

Item 10. The liquid crystal composition according to any one of items 1 to 9, wherein achiral component T further contains at least one compound selected from the group of compounds of compound 4 represented by formula (4) and compound 2 represented by formula (2):

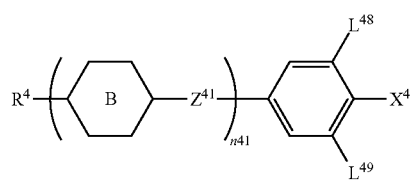

(4)

wherein, in formula (4), $R^4$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine;

ring B is each independently 1,4-cyclohexylene, 1,4-phenylene, 2-fluoro-1,4-phenylene, 3-fluoro-1,4-phenylene, 3,5-difluoro-1,4-phenylene, 3,5-dichloro-1,4-phenylene or pyrimidine 2,5-diyl;

$Z^{41}$ is each independently a single bond, ethylene, —COO—, —OCO—, —CF₂O— or —OCF₂—;

$L^{48}$ and $L^{49}$ are each independently hydrogen or fluorine;

$X^4$ is fluorine, chlorine, —CF₃ or —OCF₃; and n41 is 1, 2, 3 or 4, but when n41 is 3 or 4, at least one of $Z^{41}$ is —CF₂O— or —OCF₂—, and when n41 is 3, a case where all of rings B are 1,4-phenylene in which replacement by fluorine is caused is excluded;

wherein, in formula (2), $R^2$ is hydrogen or alkyl having 1 to 20 carbons, at least one of CH₂— in the alkyl may be replaced by —O—, —S—, —COO— or —OCO—, at least one of —CH₂—CH₂— in the alkyl may be replaced by —CHCH—, —CF═CF— or and at least one of hydrogen in the alkyl, in a group in which at least one of —CH₂— in the alkyl is replaced by —O—, —S—, —COO— or —OCO—, or in a group in which at least one of —CH₂—CH₂— in the group in which at least one of —CH₂— in the alkyl is replaced by —O—, —S—, —COO— or —OCO— is replaced by —CH═CH— or —C≡C— may be replaced by fluorine or chlorine, in which, in $R^2$, neither —O— and —CH═CH— nor —CO— and —CH═CH— are adjacent;

ring $A^{21}$, ring $A^{22}$, ring $A^{23}$, ring $A^{24}$ and ring $A^{25}$ are each independently 1,4-cyclohexylene, 1,3-dioxane 2,5-diyl, 1,4-phenylene, 1,4-phenylene in which one or two of hydrogen is replaced by fluorine, 1,4-phenylene in which two of hydrogen is replaced by fluorine and chlorine, respectively, pyridine-2,5-diyl and pyrimidine 2,5-diyl;

$Z^{21}$, $Z^{22}$, $Z^{23}$, $Z^{24}$, $Z^{25}$ and $R^{26}$ are each independently a single bond or alkylene having 1 to 4 carbons, and at least one of —CH₂— in the alkylene may be replaced by —O—, —COO— or —CF₂O—;

$L^{21}$, $L^{22}$ and $L^{23}$ are each independently hydrogen or fluorine;

$X^2$ is fluorine, chlorine, —CF₃, —CHF₂, —CH₂F, —OCF₃, —OCHF₂, —OCH₂F, —OCF₂CFHCF₃ or —CH═CHCF₃; and n21, n22, n23, n24 and n25 are each independently 0 or 1, and satisfies an expression: 2≤n21+n22+n23+24+n25≤3.

Item 11. The liquid crystal composition according to item 10, wherein compound 4 is at least one selected from the group of compounds represented by formula (4-1) to (4-9) and compound 2 is at least one selected from the group of compounds represented by formulas (2-1-1-2), (2-1-2-1), (2-1-3-1), (2-1-3-2), (2-1-4-2) and (2-1-4-3):

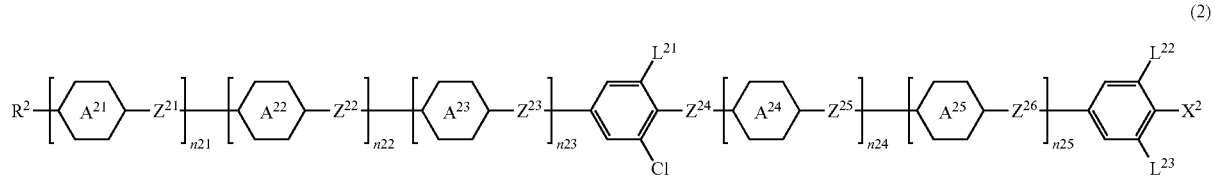

(2)

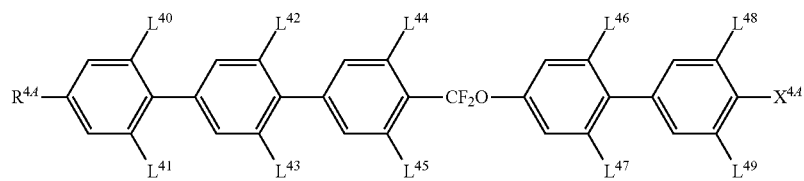
(4-1)
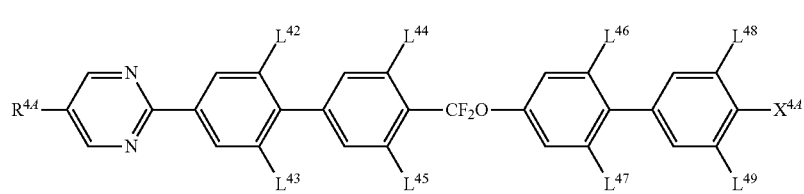
(4-2)
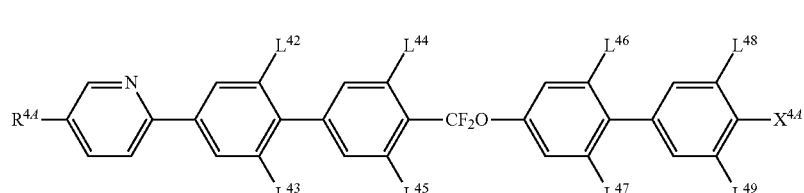
(4-3)
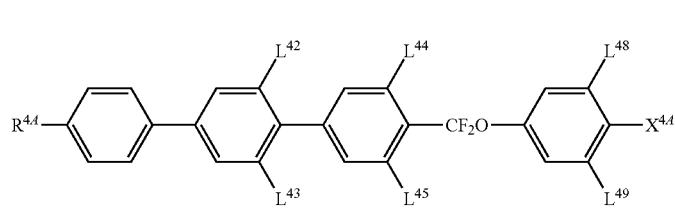
(4-4)
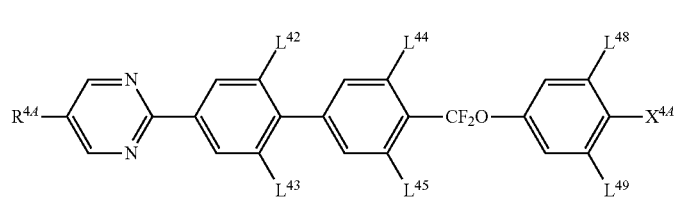
(4-5)
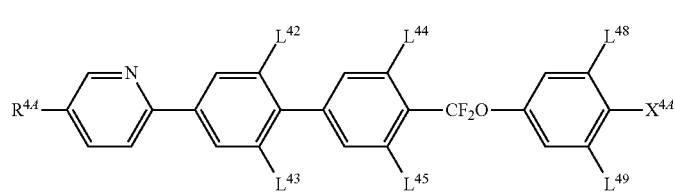
(4-6)
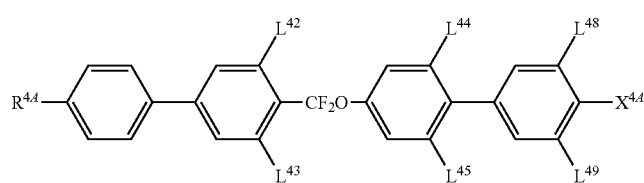
(4-7)
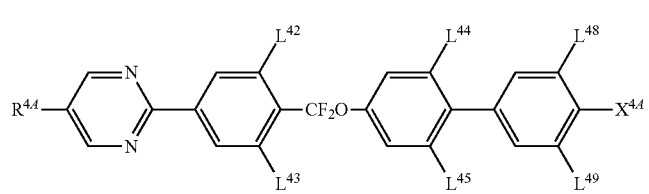
(4-8)

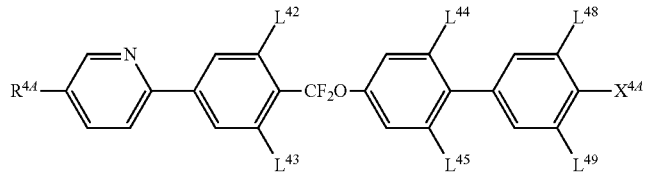

(4-9)

wherein, $R^{4A}$ is each independently alkyl having 1 to 12 carbons, alkoxy having 1 to 12 carbons, alkenyl having 2 to 12 carbons, or alkenyl having 2 to 12 carbons in which at least one of hydrogen is replaced by fluorine;

$X^{4A}$ is fluorine, chlorine, —$CF_3$ or —$OCF_3$; and $L^{40}$ to $L^{49}$ are each independently hydrogen or fluorine;

wherein, $R^{2A}$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine;

(F) is each independently hydrogen or fluorine; and $X^{2A}$ is fluorine, chlorine, —$CF_3$ or —$OCF_3$.

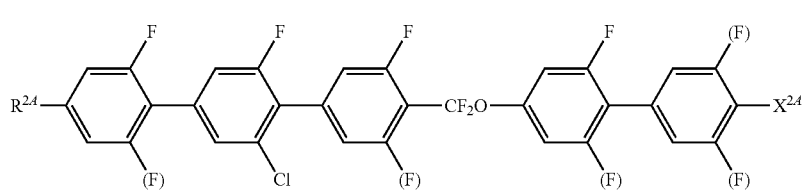

(2-1-1-2)

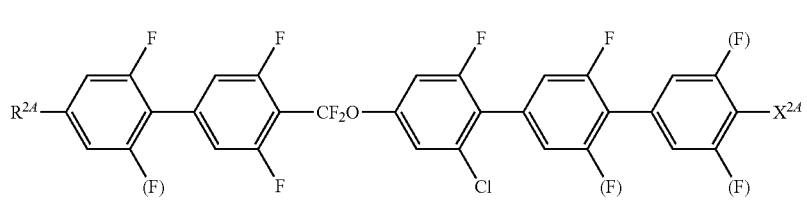

(2-1-2-1)

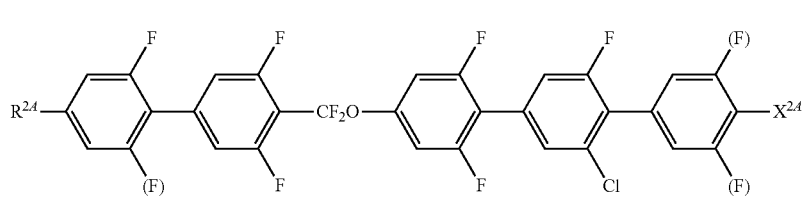

(2-1-3-1)

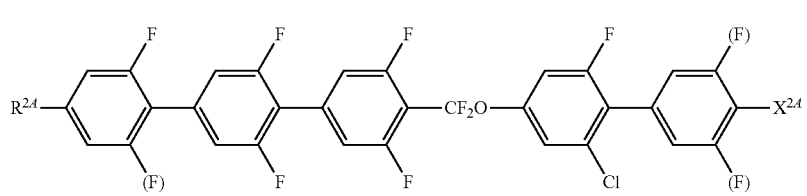

(2-1-3-2)

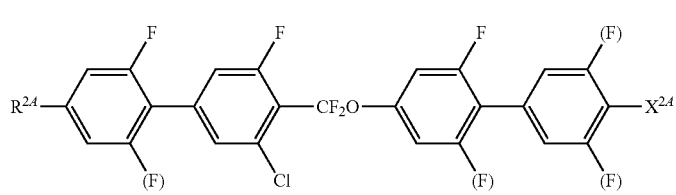

(2-1-4-2)

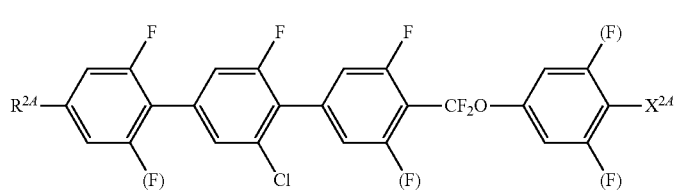

(2-1-4-3)

Item 12. The liquid crystal composition according to any one of items 1 to 11, wherein the chiral agent is at least one compound selected from the group of compounds represented by formulas (K1) to (K6):

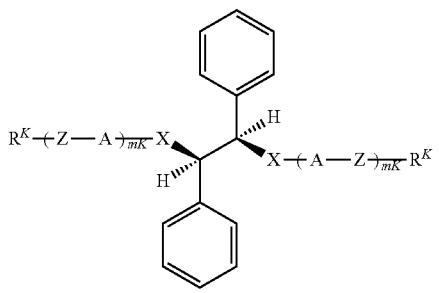
(K1)

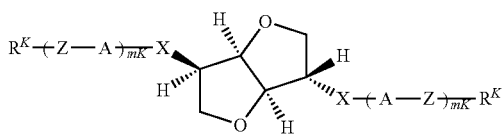
(K2)

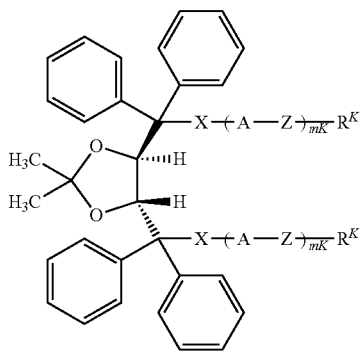
(K3)

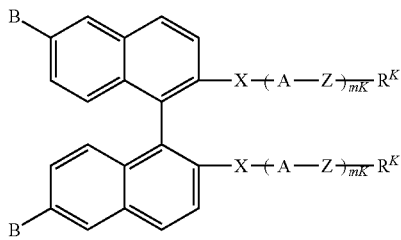
(K4)

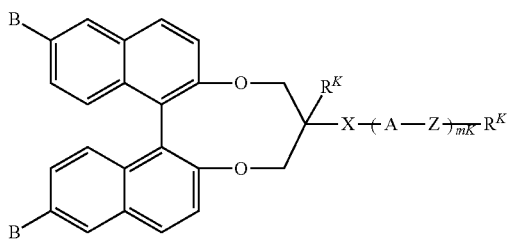
(K5)

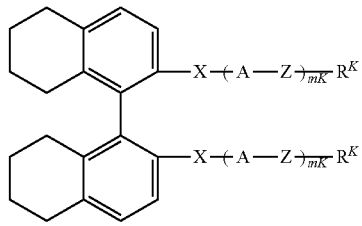
(K6)

(wherein, $R^K$ is each independently hydrogen, halogen, —C≡N, —N=C=O, —N=C=S or alkyl having 1 to 20 carbons, at least one of —CH$_2$— in the $R^K$ may be replaced by —O—, —S—, —COO— or —OCO—, at least one of —CH$_2$—CH$_2$— in the $R^K$ may be replaced by —CH=CH—, —CF=CF— or —C≡C—, and at least one of hydrogen in the alkyl, in a group in which at least one of —CH$_2$— in the $R^K$ is replaced by —O—, —S—, —COO— or —OCO—, or in a group in which at least one of —CH$_2$—CH$_2$— in the $R^K$ is replaced by —CH=CH— or —C≡C— may be replaced by fluorine or chlorine;

A is each independently a 6- to 8-membered aromatic ring, a 3- to 8-membered non-aromatic ring or a condensed ring having 9 or more carbons, at least one of hydrogen in the ring may be replaced by halogen, alkyl or haloalkyl having 1 to 3 carbons, —CH$_2$— in the ring may be replaced by —O—, —S— or —NH—, and —CH= may be replaced by —N=;

B is each independently hydrogen, halogen, alkyl having 1 to 3 carbons, haloalkyl having 1 to 3 carbons, a 6- to 8-membered aromatic ring, a 3- to 8-membered non-aromatic ring or a condensed ring having 9 or more carbons, at least one of hydrogen in the ring may be replaced by halogen, alkyl or haloalkyl having 1 to 3 carbons, —CH$_2$— in the ring may be replaced by —O—, —S— or —NH—, and —CH= may be replaced by —N=;

Z is each independently a single bond, alkylene having 1 to 8 carbons, at least one of —CH$_2$— in the alkylene may be replaced by —O—, —S—, —COO—, —OCO—, —CSO—, —OCS—, —N=N—, —CH=N— or —N=CH—, at least one of —CH$_2$—CH$_2$— in the alkylene may be replaced by —CH=CH—, —CF=CF— or —C≡C—, and in the alkylene, at least one of hydrogen in the group in which at least one of —CH$_2$— in the alkylene is replaced by —O—, —S—, —COO— or —OCO—, or in the group in which at least one of —CH$_2$—CH$_2$— in the alkylene is replaced by —CH=CH—, —CF=CF— or —C≡C— may be replaced by halogen, X is each independently a single bond, —COO—, —OCO—, —CH$_2$O—, —OCH$_2$—, —CF$_2$O—, —OCF$_2$— or —CH$_2$CH$_2$—; and mK is each independently an integer from 1 to 4.)

Item 13. The liquid crystal composition according to any one of items 1 to 12, wherein a chiral nematic phase is exhibited in any temperature from −20° C. to −70° C., and a helical pitch is 700 nanometers or less in at least part of the temperature range.

Item 14. A mixture, containing the liquid crystal composition according to any one of claims 1 to 13 and a polymerizable monomer.

Item 15. A polymer/liquid crystal composite material, obtained by polymerizing the mixture according to claim 14, and used in a device driven in an optically isotropic liquid crystal phase.

Item 16. An optical device having electrodes arranged on one or both of substrates, a liquid crystal medium arranged between the substrates, and an electric field applying means for applying an electric field to the liquid crystal medium through the electrode, wherein the liquid crystal medium is the liquid crystal composition according to any one of claims 1 to 13, or the polymer/liquid crystal composite material according to claim 15.

Item 17. Use of the liquid crystal composition according to any one of items 1 to 13 or the polymer/liquid crystal composite material according to claim 15 in an optical device.

"Liquid crystal compound" herein represents a compound having a mesogen, and is not limited to a compound having a liquid crystal phase. Specifically, "liquid crystal compound" is a generic term for a compound developing a liquid crystal phase such as a nematic phase and a smectic phase, and also a compound having no liquid crystal phase but being useful as a component of a liquid crystal composition.

"Liquid crystal medium" is a generic term for the liquid crystal composition and the polymer/liquid crystal composite.

"Achiral component" means an achiral mesogenic compound, and is a component containing neither an optically active compound nor a compound having a polymerizable functional group.

Accordingly, "achiral component" contains no chiral agent, no monomer, no polymerization initiator, no antioxidant, no ultraviolet light absorbent, no curing agent, no stabilizer or the like.

"Chiral agent" is an optically active compound and a component to be added for providing the liquid crystal composition with desired twisted alignment of molecules.

"Liquid crystal display device" is a generic term for a liquid crystal display panel and a liquid crystal display module.

Moreover, "optical device means various kinds of devices that perform a function of optical modulation, optical switching or the like by utilizing an electro-optic effect. Specific examples include an optical modulator used for a display device (liquid crystal display device), an optical communication system, optical information processing and various kinds of sensor systems. With regard to optical modulation that utilizes a change of a refractive index by applying voltage to an optically isotropic liquid crystal medium, a Kerr effect is known. The Kerr effect means a phenomenon in which a value of electric birefringence $\Delta n(E)$ is proportional to a square of electric field E, and an equation: $\Delta n(E)=K\lambda E^2$ holds in a material showing the Kerr effect (K: Kerr coefficient (Kerr constant), $\lambda$: wavelength). Here, the value of electric birefringence means a value of refractive index anisotropy induced when the electric field is applied to an isotropic medium.

"Liquid crystal compound," "liquid crystal composition" and "liquid crystal display device" may be occasionally abbreviated as "compound," "composition" and "device."

Moreover, a maximum temperature is a phase transition temperature between the liquid crystal phase and an isotropic phase, and may be occasionally abbreviated simply as "clearing point" or "maximum temperature." A minimum temperature of the liquid crystal phase may be occasionally abbreviated as "minimum temperature." A compound represented by formula (1) may be occasionally abbreviated as "compound 1." The abbreviation may occasionally apply to a compound represented by formula (2) or the like. In formulas (2) to (5), a symbol such as $A^1$, B or C surrounded by a hexagonal shape corresponds to ring $A^1$, ring B or ring C, respectively. An amount of compound expressed in terms of percentage is expressed in terms of weight percentage (% by weight) based on the total weight of the composition. A plurality of identical symbols such as ring $A^1$, $Y^1$ and B are described in identical formulas or different formulas, but the symbols may be identical or different.

Specific examples of "alkyl" herein include —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$, —$C_{12}H_{25}$, —$C_{13}H_{27}$, —$C_{14}H_{29}$ and —$C_{15}H_{31}$.

Specific examples of "alkoxy" herein include —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$, —$OC_9H_{19}$, —$OC_{10}H_{21}$, —$OC_{11}H_{23}$, —$OC_{12}H_{25}$, —$OC_{13}H_{27}$ and —$OC_{14}H_{29}$.

Specific examples of "alkoxyalkyl" herein include —$CH_2OCH_3$, —$CH_2OC_2H_5$, —$CH_2OC_3H_7$, —$(CH_2)_2$—$OCH_3$, —$(CH_2)_2$—$OC_2H_5$, —$(CH_2)_2$—$OC_3H_7$, —$(CH_2)_3$—$OCH_3$, —$(CH_2)_4$—$OCH_3$ and —$(CH_2)_5$—$OCH_3$.

Specific examples of "alkenyl" herein include —$CH=CH_2$, —$CH=CHCH_3$, —$CH_2CH=CH_2$, —$CH=CHC_2H_5$, —$CH_2CH=CHCH_3$, —$(CH_2)_2$—$CH=CH_2$, —$CH=CHC_3H_7$, —$CH_2CH=CHC_2H_5$, —$(CH_2)_2$—$CH=CHCH_3$ and —$(CH_2)_3$—$CH=CH_2$.

Specific examples of "alkenyloxy" herein include —$OCH_2CH=CH_2$, —$OCH_2CH=CHCH_3$ and —$OCH_2CH=CHC_2H_5$.

Specific examples of "alkynyl" herein include —$C{\equiv}CH$, —$C{\equiv}CCH_3$, —$CH_2C{\equiv}CH$, —$C{\equiv}CC_2H_5$, —$CH_2C{\equiv}CCH_3$, —$(CH_2)_2$—$C{\equiv}CH$, —$C{\equiv}CC_3H_7$, —$CH_2C{\equiv}CC_2H_5$, —$(CH_2)_2$—$C{\equiv}CCH_3$ and —$C{\equiv}C(CH_2)_5$.

Specific examples of "halogen" herein include fluorine, chlorine, bromine and iodine.

Advantageous Effects of Invention

A preferred liquid crystal composition, a preferred polymer/liquid crystal composite material or the like according to the invention shows stability to heat, light and so forth, a high maximum temperature of an optically isotropic liquid crystal phase, and a low minimum temperature thereof, and has a large dielectric anisotropy. The polymer/liquid crystal composite material having a preferred aspect of the invention shows a high maximum temperature or a low minimum temperature of the optically isotropic liquid crystal phase, and a low minimum temperature thereof, and has a low driving voltage and a short response time in the device to be driven in the optically isotropic liquid crystal phase.

Moreover, the optical device to be driven in the optically isotropic liquid crystal phase in a preferred aspect of the invention can be used in a wide temperature range, can be driven at a low voltage, can achieve high transmittance or a large contrast ratio and has a high-speed electro-optic response.

DESCRIPTION OF EMBODIMENTS

Figure 1:
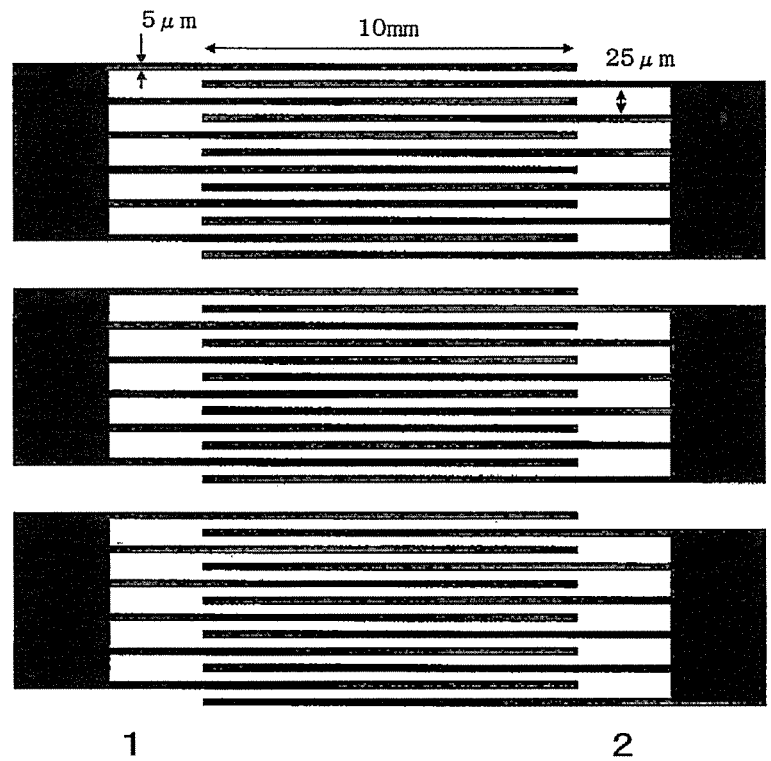
FIG. 1 shows a comb-shaped electrode substrate used in Examples.

A liquid crystal composition having an optically isotropic liquid crystal phase according to the invention contains achiral component T and a chiral agent, and the achiral component T contains a compound represented by formula (1) as a first component. A first aspect of the liquid crystal composition according to the invention is a composition containing the first component and any other component whose component name is not particularly shown herein. First, the compound represented by formula (1) will be described. Moreover, the liquid crystal composition according to the invention may further contain, in addition to the component described above, a solvent, a monomer, a polymerization initiator, a curing agent, a stabilizer (an antioxidant, an ultraviolet light absorbent) or the like.

1-1 Compound 1

In formula (1), $R^1$ is hydrogen or alkyl having 1 to 20 carbons, at least one of —$CH_2$— in the alkyl may be replaced by —O—, —S—, —COO—, —OCO—, —CH=CH—, —CF=CF— or —C≡C—, and at least one of hydrogen in the alkyl and in a group in which —$CH_2$— in the alkyl is replaced by —O—, —S—, —COO—, —OCO—, —CH=CH—, —CF=CF— or —C≡C— may be replaced by halogen or alkyl having 1 to 3 carbons.

Specific examples of the group in which at least one of —$CH_2$— in $CH_3(CH_2)_3$— is replaced by —O—, —S— or —CH=CH— include $CH_3(CH_2)_2O$—, $CH_3$—O—$(CH_2)_2$—, $CH_3$—O—$CH_2$—O—, $CH_3(CH_2)_2S$—, $CH_3$—S—$(CH_2)_2$—, $CH_3$—S—$CH_2$—S—, $CH_2$—CH—$(CH_2)_3$—, $CH_3$—CH=CH—$(CH_2)_2$—, $CH_3$—CH=CH—$CH_2O$— and $CH_3CH_2C$=C—. Specific examples of the group in which at least one of hydrogen in $CH_3(CH_2)_3$— or in a group in which at least one of —$CH_2$— in $CH_3(CH_2)_3$— is replaced by —O—, —C≡C— or —CH=CH— is replaced by halogen include $ClCH_2(CH_2)_3$—, $CF_2$=CH—$(CH_2)_3$—, $CH_2F(CH_2)_2O$— and $CH_2FCH_2C$≡C—.

A preferred configuration of —CH=CH— in $R^1$ depends on a position of a double bond. A trans configuration is preferred in alkenyl having a double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ and —C$_2$H$_4$CH=CHC$_2$H$_5$. A cis configuration is preferred in alkenyl having a double bond in an even-numbered position, such as —CH$_2$CH=CHCH$_3$, —CH$_2$CH=CHC$_2$H$_5$ and —CH$_2$CH=CHC$_3$H$_7$. An alkenyl compound having the preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327. Moreover, as the position of alkenyl group, a position is preferred in which no conjugation with a benzene ring is formed.

Alkyl in $R^1$ may have a straight chain or a branched chain. Specific examples of the alkyl include —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$, —C$_{14}$H$_{29}$ and —C$_{15}$H$_{31}$.

Alkoxy in $R^1$ may have a straight chain or a branched chain. Specific examples of the alkoxy include —OCH$_3$, —OC$_2$H$_5$, —OC$_3$H$_7$, —OC$_4$H$_9$, —OC$_5$H$_{11}$, —OC$_6$H$_{13}$, —OC$_7$H$_{15}$, —OC$_8$H$_{17}$, —OC$_9$H$_{19}$, —OC$_{10}$H$_{21}$, —OC$_{11}$H$_{23}$, —OC$_{12}$H$_{25}$, —OC$_{13}$H$_{27}$ and —OC$_{14}$H$_{29}$.

Alkoxyalkyl in $R^1$ may have a straight chain or a branched chain. Specific examples of the alkoxyalkyl include —CH$_2$OCH$_3$, —CH$_2$OC$_2$H$_5$, —CH$_2$OC$_3$H$_7$, —(CH$_2$)$_2$—OCH$_3$, —(CH$_2$)$_2$—OC$_2$H$_5$, —(CH$_2$)$_2$—OC$_3$H$_7$, —(CH$_2$)$_3$—OCH$_3$, —(CH$_2$)$_4$—OCH$_3$ and —(CH$_2$)$_5$—OCH$_3$.

Alkenyl in $R^1$ may have a straight chain or a branched chain. Specific examples of the alkenyl include —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$ and —(CH$_2$)$_3$—CH=CH$_2$.

Alkenyloxy in $R^1$ may have a straight chain or a branched chain. Specific examples of the alkenyloxy include —OCH$_2$CH=CH$_2$, —OCH$_2$CH=CHCH$_3$ and —OCH$_2$CH=CHC$_2$H$_5$.

Alkynyl in $R^1$ may have a straight chain or a branched chain. Specific examples of the alkynyl include —C≡CH, —C≡CCH$_3$, —CH$_2$C≡CH, —C≡CC$_2$H$_5$, —CH$_2$C≡CCH$_3$, —(CH$_2$)$_2$—C≡CH, —C≡CC$_3$H$_7$, —CH$_2$C≡CC$_2$H$_5$, —(CH$_2$)$_2$—C≡CCH$_3$ and —C≡C(CH$_2$)$_5$.

$R^1$ preferably has a structure represented by (CHN-1) to (CHN-6). The structure is further preferably represented by (CHN-1) or (CHN-2).

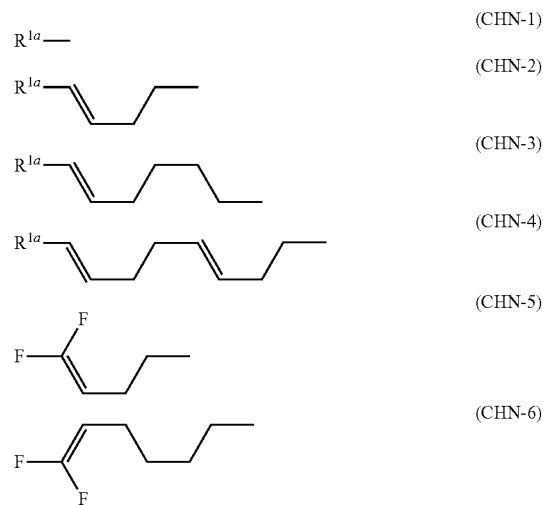

(in the formula, $R^{1a}$ is hydrogen or alkyl having 1 to 20 carbons.)

In formula (1), $X^1$ is halogen, —CF$_3$, —OCF$_3$, —C≡N or —N=C=S.

Specific preferred examples of $X^1$ include fluorine and —CF$_3$.

Compound 1 is preferably a compound of formula (1-1).

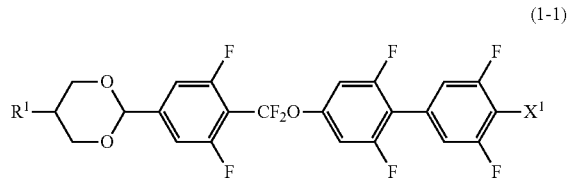

In formula (1-1), R' is hydrogen or alkyl having 1 to 20 carbons, at least one of —CH$_2$— in the alkyl may be replaced by —O—, —S—, —COO—, —OCO—, —CH=CH—, —CF=CF— or —C≡C—, at least one of hydrogen in the alkyl or in a group in which —CH$_2$— in the alkyl is replaced by —O—, —S—, —COO—, —OCO—, —CH=CH—, —CF=CF— or —C≡C— may be replaced by halogen or alkyl having 1 to 3 carbons; and $X^1$ is halogen, —CF$_3$, —OCF$_3$, —C≡N or —N=C=S.

Compound 1 is further preferably a compound represented by formulas (1-1-1) to (1-1-2).

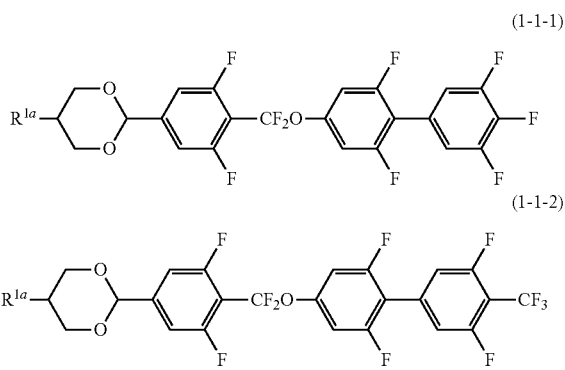

(in the formula, $R^{1a}$ is alkyl having 1 to 10 carbons.)

1-2 Properties of Compound 1

Compound (1) is significantly physically and chemically stable under conditions in which the device is ordinarily used, and has a large dielectric anisotropy and a relatively large refractive index anisotropy, and has relatively good compatibility with other compounds. A composition containing the compound is stable under the conditions in which the device is ordinarily used. Accordingly, compound 1 can reduce the driving voltage even by using a small amount. Moreover, a composition having a short response time can be prepared by mixing compound 1 with a compound that increases the driving voltage and shortens the response time.

1-3 Synthesis of Compound 1

Compound 1 can be prepared by suitably combining techniques in synthetic organic chemistry. A plurality of methods for preparing compound 1 are provided, and compound 1 can be appropriately prepared from commercially available reagents. Upon preparing compound 1, methods for introducing an objective terminal group, ring and bonding group into a starting material are described in Organic Syntheses (John Wiley & Sons, Inc.), Organic Reactions (John Wiley & Sons, Inc.), Comprehensive Organic Synthesis (Pergamon Press), New Experimental Chemistry Course (Shin Jikken Kagaku Koza in Japanese) (Maruzen Co., Ltd.), or the like. For example, compound 1 can be prepared by correspondingly applying the method described in JP 2959526 B.

2-1 Liquid Crystal Composition

The liquid crystal composition according to the invention is a composition that contains compound 1 represented by formula (1) and develops the optically isotropic liquid crystal phase. Moreover, the optically isotropic liquid crystal composition may contain, in addition to achiral component T containing compound 1, the chiral agent and may further contain an antioxidant, an ultraviolet light absorbent, a stabilizer or the like.

Achiral component T includes a case of being formed of one compound as compound 1, and also a case of containing a plurality of compounds represented by formula (1) as compound 1. Further, the achiral component contains at least one compound selected from the group of compounds 2 to 7, when necessary. Achiral component T preferably contains, in addition to compound 1, compounds 2, 3, 5 and 7, and further preferably contains compounds 3 and 7, and can further contain compounds 4 and 6 according to required properties. Compounds 1 to 7 are liquid crystal compounds.

Compound 1 simultaneously has a relatively high clearing point, a large dielectric anisotropy and a relatively good compatibility at a low temperature, and therefore achiral component T containing compound 1 also has a wide liquid crystal phase temperature range or develops a large dielectric anisotropy. Therefore, the optically isotropic liquid crystal composition containing achiral component T is also useful as the composition to be used in the optical device.

The composition preferably contains compound 1 in a total amount of preferably 1% by weight to 30% by weight, further preferably 3% by weight to 20% by weight, and particularly preferably 5% by weight to 15% by weight, based on the total weight of achiral component T.

In order to develop the large dielectric anisotropy, a compound selected from the group represented by compounds 3 and 7 is preferably further added. The composition develops a significantly large dielectric anisotropy, and therefore is significantly effective in achieving voltage reduction in the optical device.

2-2-1 Compound 2

The achiral component according to the invention may further contain, in addition to compound 1, at least one compound 2 represented by formula (2). More specifically, in achiral component T, the invention includes a case where the achiral component is formed of one compound as compound 2, and also a case where the achiral component contains a plurality of compounds represented by formula (2) as compound 2.

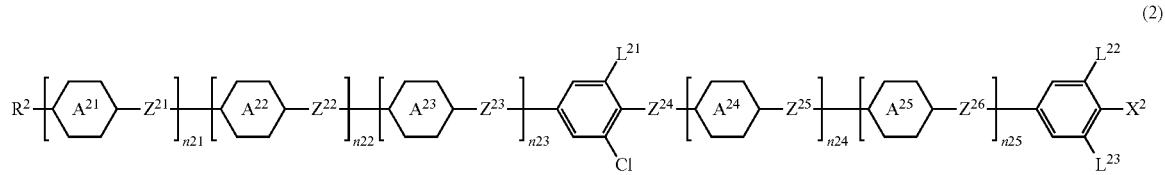

$R^2$ in formula (2) is preferably alkyl having 1 to 12 carbons, alkoxy having 1 to 12 carbons, alkenyl having 2 to 12 carbons, or alkenyl having 2 to 12 carbons in which at least one of hydrogen is replaced by fluorine.

In view of stability and the large dielectric anisotropy of the compound, ring $A^{21}$, ring $A^{22}$, ring $A^{23}$, ring $A^{24}$ and ring $A^{25}$ in formula (2) are preferably 1,4-phenylene or 1,4-phenylene in which one or two of hydrogen is replaced by fluorine.

$Z^{21}$, $Z^{22}$, $Z^{23}$, $Z^{24}$, $Z^{25}$ and $Z^{26}$ in formula (2) are independently a single bond or alkylene having 1 to 4 carbons, and at least one of —$CH_2$— in the alkylene may be replaced by —O—, —COO— or —$CF_2O$—. $Z^{21}$, $Z^{22}$, $Z^{23}$, $Z^{24}$, $Z^{25}$ and $Z^{26}$ in formula (2) are all single bonds or at least one group is preferably —COO— or —$CF_2O$—, and when compatibility with other liquid crystal compounds is considered to be important, at least one group is preferably —$CF_2O$—. In formula (2), an equation: n24=1 is particularly preferably satisfied and $Z^{25}$ is particularly preferably —$CF_2O$—.

$X^2$ in formula (2) is fluorine, chlorine, —$CF_3$, —$CHF_2$, —$CH_2F$, —$OCF_3$, —$OCHF_2$, —$OCH_2F$, —$OCF_2CFHCF_3$ or —CH=$CHCF_3$, and is preferably fluorine, chlorine, —$CF_3$ and —$OCF_3$.

In compound 2, a compound represented by formula (2-1) is preferably used.

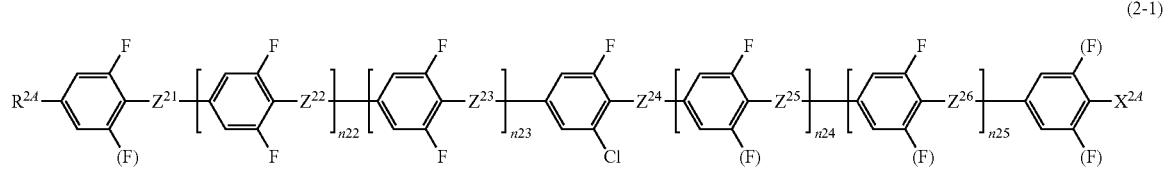

(2-1)

(in the formula, $R^{24}$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine;

$Z^{21}$, $Z^{22}$, $Z^{23}$, $Z^{24}$, $Z^{25}$ and $Z^{26}$ are each independently a single bond or alkylene having 1 to 4 carbons, and in the alkylene, at least one of —$CH_2$— may be replaced by —O—, —COO— or —$CF_2O$—;

n22, n23, n24 and n25 in formula (2-1) are independently 0 or 1, and a sum: n22+n23+n24+n25 is an integer from 1 to 2.

$X^{24}$ is fluorine, chlorine, —$CF_3$ and —$OCF_3$; and (F) each independently represents hydrogen or fluorine.)

With regard to a preferred configuration of —CH=CH— in the alkenyl in $R^{24}$ and $Z^{21}$ to $Z^{26}$ in formula (2) and formula (2-1), the preferred configuration of —CH=CH— in $R^1$ in formula (1) is correspondingly applied thereto.

$Z^{21}$, $Z^{22}$, $Z^{23}$, $Z^{24}$, $Z^{25}$ and $Z^{26}$ are each independently a single bond or —$CF_2O$—, and when compatibility with other liquid crystal compounds is considered to be important, at least one of $Z^{21}$, $Z^{22}$, $Z^{23}$, $Z^{24}$, $Z^{25}$ and $Z^{26}$ is preferably —$CF_2O$—.

In formula (2-1), an equation: n24=1 is particularly preferably satisfied, and $Z^{25}$ is particularly preferably —$CF_2O$—.

In compound 2, compounds represented by formulas (2-1-1) to (2-1-5) are further preferably used.

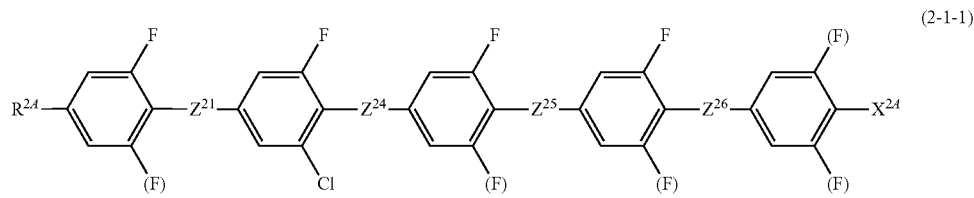

(2-1-1)

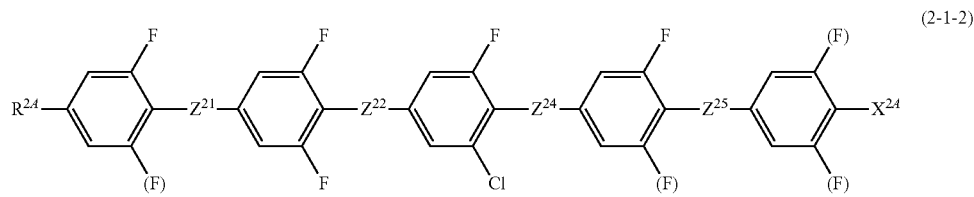

(2-1-2)

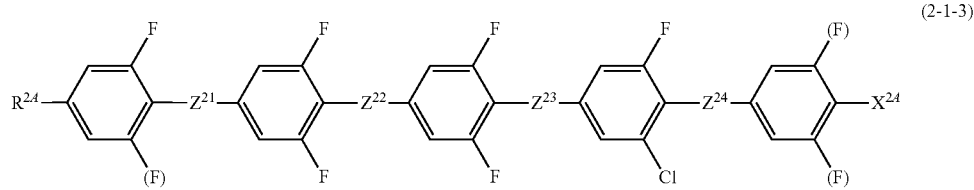

(2-1-3)

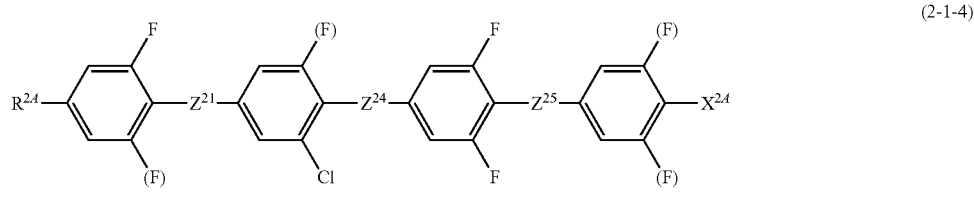

(2-1-4)

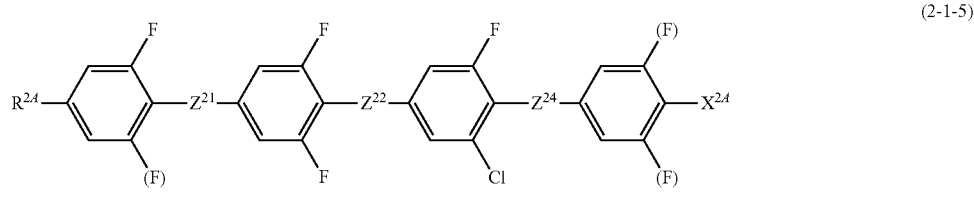

(2-1-5)

(in the formulas, $R^{2A}$, $Z^{21}$ to $Z^{26}$, $X^{2A}$ and (F) are defined in a manner identical with the definitions in formula (2-1).)
When the compounds represented by formulas (2-1-1) to (2-1-5) are used as compound 2, compounds represented by formulas (2-1-1-1) to (2-1-1-3), (2-1-2-1) to (2-1-2-3), (2-1-3-1) to (2-1-3-3), (2-1-4-1) to (2-1-4-3) and (2-1-5-1) to (2-1-5-3) described below are preferably used, and compounds represented by formulas (2-1-1-1), (2-1-1-2), (2-1-2-1), (2-1-2-2), (2-1-3-1), (2-1-3-2), (2-1-4-2), (2-1-4-3) and (2-1-5-3) are further preferably used.
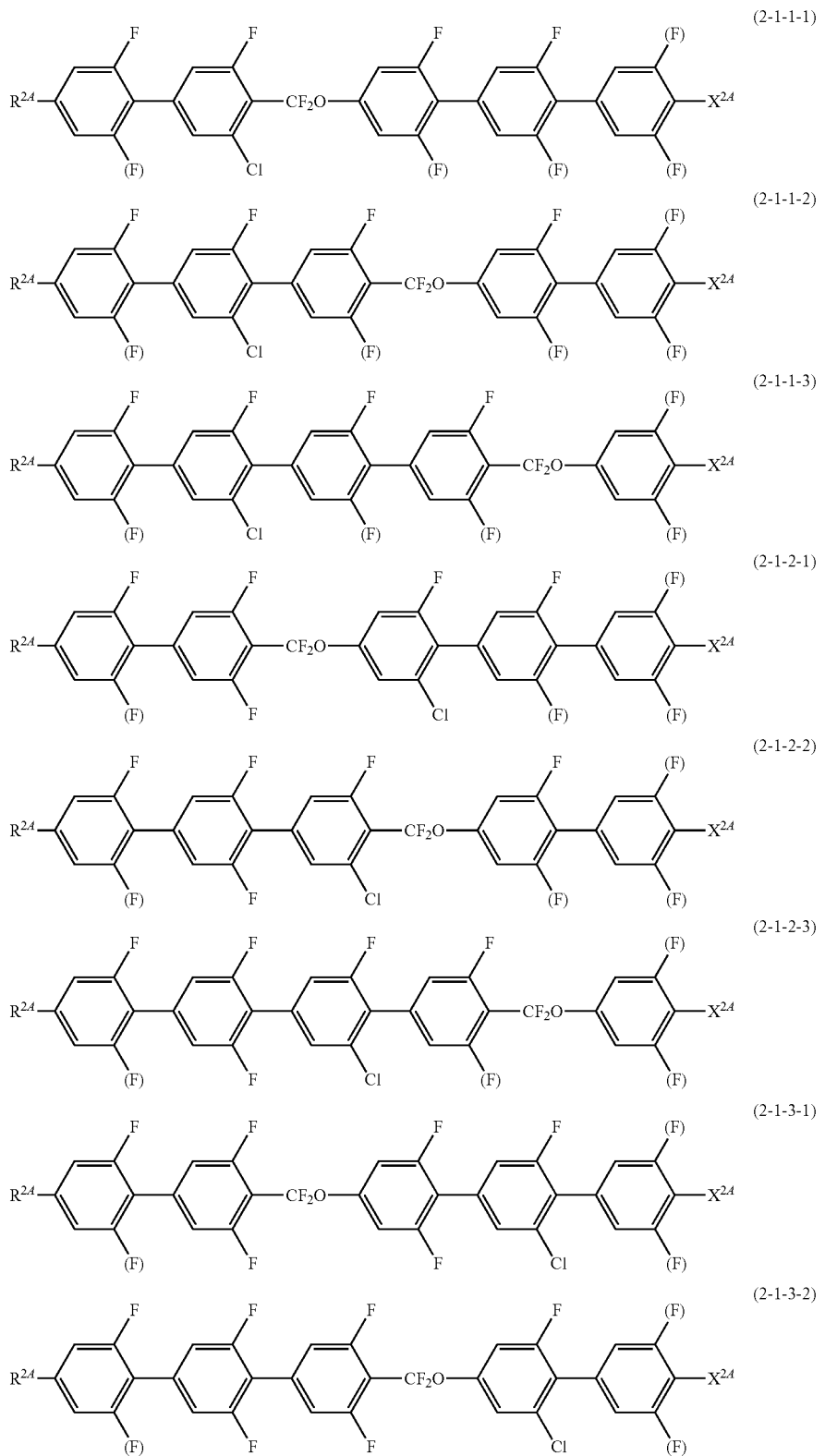

-continued

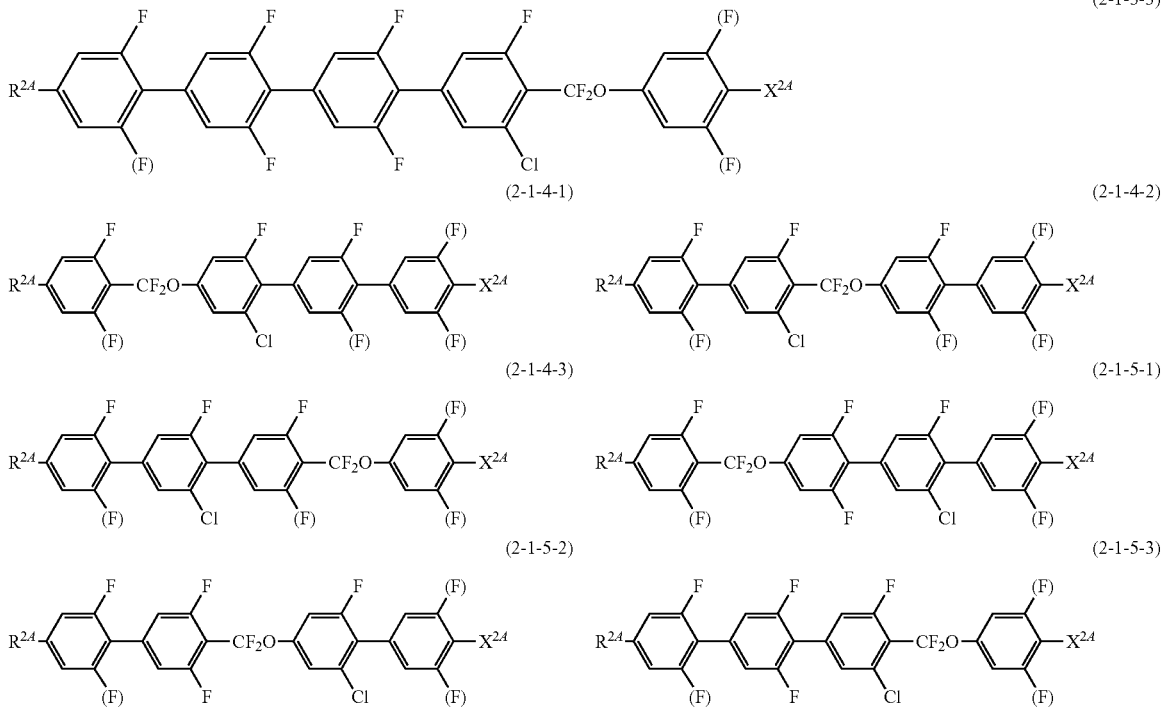

(in the formulas described above, $R^{2A}$, (F) and $X^{2A}$ are defined in a manner identical with the definitions in formula (2-1).)

Among the compounds, compound 2 is preferably compounds represented by formulas (2-1-1-2), (2-1-2-1), (2-1-3-1), (2-1-3-2), (2-1-4-2) or (2-1-4-3).

Compound 2 has good compatibility, a large dielectric anisotropy and a large refractive index anisotropy.

The composition preferably contains compound 2 in a total amount of preferably 0.5% by weight to 70% by weight, further preferably 5% by weight to 60% by weight, and particularly preferably 10% by weight to 50% by weight, based on the total weight of achiral component T.

2-2-2 Properties of Compound 2

Compound 2 has a chlorobenzene ring. Compound 2 is significantly physically and chemically stable under conditions in which the device is ordinarily used, and has good compatibility with other liquid crystal compounds. Further, compound 2 is hard to develop a smectic phase. A composition containing the compound is stable under the conditions in which the device is ordinarily used. Accordingly, a temperature range of a cholesteric phase in the composition can be extended, and the composition can be used in the form of a display device in a wide temperature range. Further, the compound has a large dielectric anisotropy and refractive index anisotropy, and therefore reduces driving voltage of the composition driven in the cholesteric phase. Therefore, the compound is useful as a component for increasing reflectivity.

Physical properties such as a clearing point, refractive index anisotropy and dielectric anisotropy can be arbitrarily adjusted by suitably selecting a combination of n22 to n25, left-terminal group $R^{2A}$, a group on a rightmost benzene ring and substitution positions thereof ((F) and $X^{2A}$), or bonding groups $Z^{22}$ to $Z^{26}$ in formula (2). An effect of the combination of n22, n23, n24 and n25, and kinds of left-terminal group $R^{2A}$, right-terminal group $X^{2A}$ bonding groups $Z^{21}$ to $Z^{26}$ and (F) on the properties of compound 2 are described below.

In general, in formula (2), a composition satisfying an equation: n22+n23+n24+n25=2 has a high clearing point, and a compound satisfying an equation: n22+n23+n24+n25=1 has a low clearing point.

When $R^{2A}$ in formula (2) is alkenyl, with regard to a preferred configuration, the preferred configuration of —CH=CH— in $R^1$ in formula (1) is correspondingly applied thereto.

Bonding groups $Z^{21}$ to $Z^{26}$ in formula (2) are a single bond or —CF$_2$O—, and therefore compound 2 is relatively chemically stable and relatively hard to cause deterioration. Further, when the bonding group is a single bond, viscosity is small. Moreover, when the bonding group is —CF$_2$O—, dielectric anisotropy is large.

When right-terminal group $X^2$ in formula (2) is fluorine, chlorine or —OCF$_3$, compatibility with other liquid crystal compounds at a low temperature is excellent, and when the group is —CF$_3$, an effect on reducing the driving voltage is large.

When (F) in formula (2) is hydrogen, a melting point is low, and when (F) is fluorine, the dielectric anisotropy is large.

A compound having objective physical properties can be obtained by suitably selecting kinds of ring structure, the terminal group, the bonding group or the like in formula (2).

2-3-1 Compound 3

The achiral component according to the invention may further contain, in addition to compound 1, at least one compound 3 represented by formula (3). More specifically, in achiral component T, the invention includes a case where the achiral component is formed of one compound as compound 3, and also a case where the achiral component contains a plurality of compounds represented by formula (3) as compound 3. Moreover, for example, the liquid crystal composition according to the invention may contain, in addition to compound 1 and compound 3, at least one compound selected from the group of compounds 2 and 4 to 7.

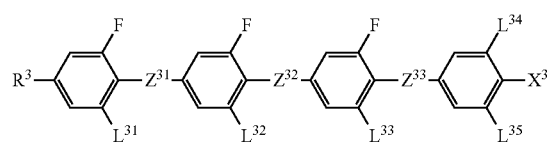
(3)

In formula (3), with regard to a preferred configuration of —CH=CH— in the alkenyl in $R^3$, the preferred configuration of —CH=CH— in $R^1$ in formula (1) is correspondingly applied thereto.

In formula (3), $Z^{31}$, $Z^{32}$ and $Z^{33}$ are independently a single bond, —COO— or —CF$_2$O—, but at least one of $Z^{31}$, $Z^{32}$ and $Z^{33}$ is —CF$_2$O—. Preferred examples of $Z^{31}$, $Z^{32}$ and $Z^{33}$ are a single bond and —CF$_2$O—.

In formula (3), $L^{31}$, $L^{32}$, $L^{33}$, $L^{34}$ and $L^{35}$ are each independently hydrogen or fluorine. When $Z^{32}$ is —COO— or —CF$_2$O—, $L^{32}$, $L^{34}$ and $L^{35}$ are preferably fluorine, and when $Z^{33}$ is —COO— or —CF$_2$O—, $L^{33}$, $L^{34}$ and $L^{35}$ are preferably fluorine.

Specific examples of alkyl in which at least one of hydrogen in $X^3$ in formula (3) is replaced by halogen include —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F and —(CF$_2$)$_5$—F.

Specific examples of alkoxy in which at least one of hydrogen is replaced by halogen include —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F and —O—(CF$_2$)$_5$—F.

Specific examples of alkenyl in which at least one of hydrogen is replaced by halogen include —CH=CHF, —CH=CF$_2$, —CF=CHF, —CH=CHCH$_2$F, —CH=CHCF$_3$, —(CH$_2$)$_2$—CH=CF$_2$, —CH$_2$CH=CHCF$_3$, —CH=CHCF$_3$ and —CH=CHCF$_2$CF$_3$.

In formula (3), $X^3$ is preferably fluorine, chlorine, —CF$_3$, —CHF$_2$, —OCF$_3$ and —OCHF$_2$, and further preferably fluorine, chlorine, —CF$_3$ and —OCF$_3$.

In compound 3, compounds represented by formulas (3-1) to (3-3) are preferably used, and compounds represented by formulas (3-2) and (3-3) are further preferably used. In the compound represented by formula (3-2), compounds represented by formulas (3-2) to (3-2H) are further preferably used, compounds represented by formulas (3-2A) to (3-2D) are especially preferably used, and compounds represented by formulas (3-2A) and (3-2C) are most preferably used. In the compound represented by formula (3-3), compounds represented by formulas (3-3A) to (3-3D) are further preferably used, compounds represented by formulas (3-3A) and (3-3B) are especially preferably used, and compounds represented by formula (3-3A) are most preferably used.

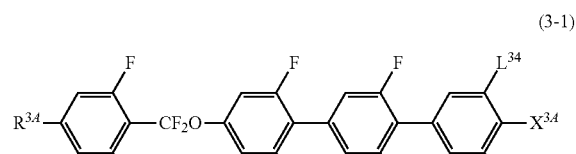
(3-1)

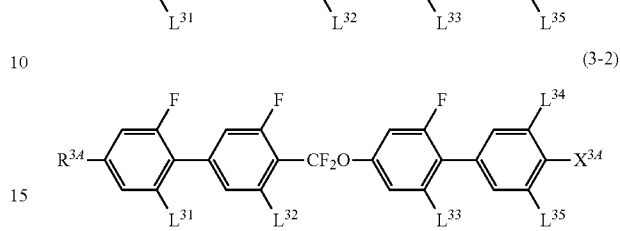
(3-2)

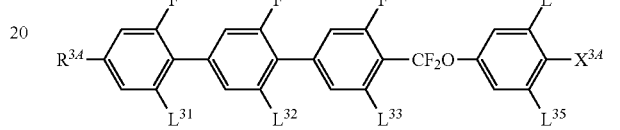
(3-3)

(in the formula, $R^{3A}$ is each independently alkyl having 1 to 12 carbons, alkoxy having 1 to 12 carbons, alkenyl having 2 to 12 carbons, or alkenyl having 2 to 12 carbons in which at least one of hydrogen may be replaced by fluorine;

$L^{31}$ to $L^{35}$ are each independently hydrogen or fluorine; and $X^{3A}$ is fluorine, chlorine, —CF$_3$ or —OCF$_3$.)

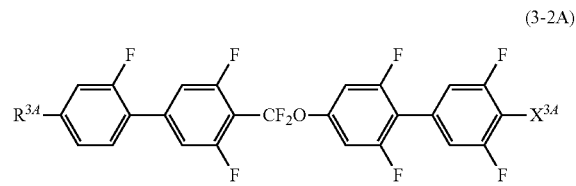
(3-2A)

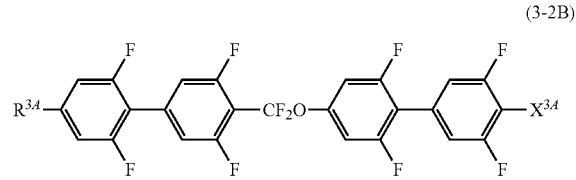
(3-2B)

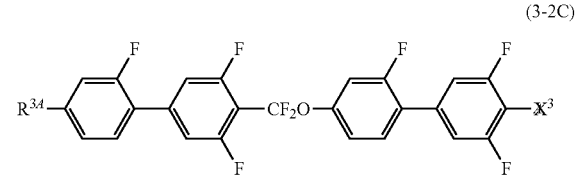
(3-2C)

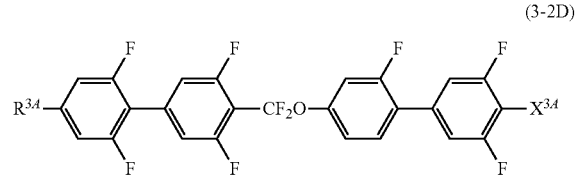
(3-2D)

-continued

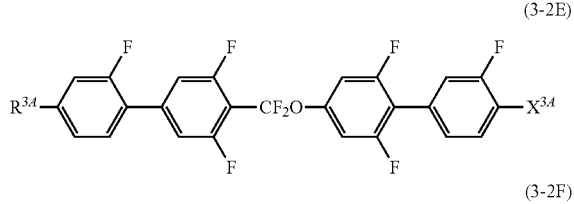
(3-2E)

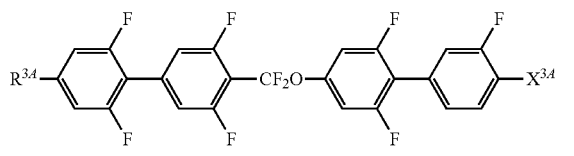
(3-2F)

(3-2G)

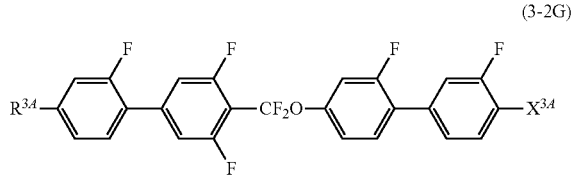
(3-2H)

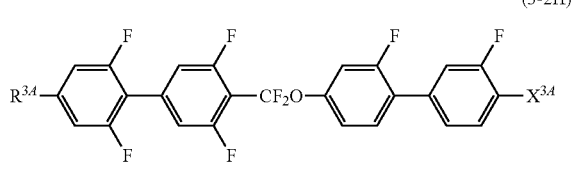
(3-3A)

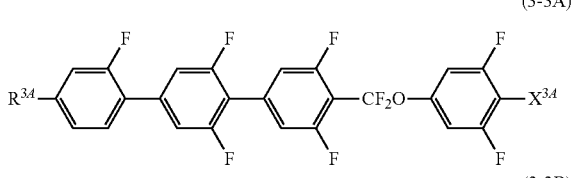
(3-3B)

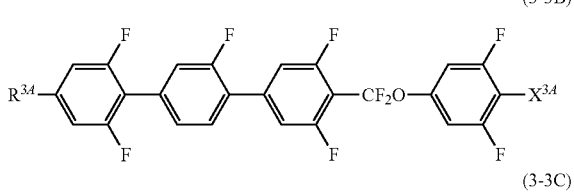
(3-3C)

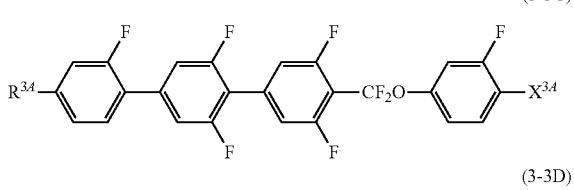
(3-3D)

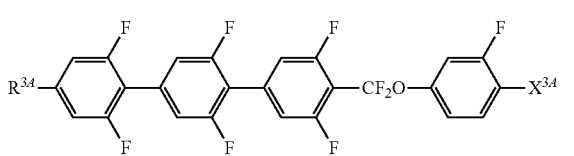

(in the formula described above, $R^{34}$ is independently alkyl having 1 to 12 carbons, alkoxy having 1 to 12 carbons, alkenyl having 2 to 12 carbons, or alkenyl having 2 to 12 carbons in which at least one of hydrogen may be replaced by fluorine; and $X^{34}$ is fluorine, chlorine, —$CF_3$ or —$OCF_3$.)

Compound 3 has a relatively high clearing point, a large dielectric anisotropy and a large refractive index anisotropy. The composition preferably contains compound 3 in a total amount of preferably 0.5% by weight to 70% by weight, further preferably 5% by weight to 60% by weight, and still further preferably 10% by weight to 50% by weight, based on the total weight of achiral component T.

2-3-2 Properties of Compound 3

Compound 3 has four benzene rings and at least one of —$CF_2O$— linking group. Compound 3 is significantly physically and chemically stable under conditions in which the device is ordinarily used, and has good compatibility with other liquid crystal compounds. A composition containing the compound is stable under the conditions in which the device is ordinarily used. Accordingly, a temperature range of the cholesteric phase in the composition can be extended, and the composition can be used in the form of a display device in a wide temperature range. Further, the compound has a large dielectric anisotropy and refractive index anisotropy, and therefore reduces driving voltage of the composition driven in the cholesteric phase. Therefore, the compound is useful as a component for increasing reflectivity.

Physical properties such as a clearing point, refractive index anisotropy and dielectric anisotropy can be arbitrarily adjusted by suitably selecting left-terminal group R3, groups on the benzene ring ($L^{31}$ to $L^{35}$ and $X^3$) or bonding groups $Z^{31}$ to $Z^{33}$. An effect of kinds of left-terminal group $R^3$, groups on the benzene ring ($L^{31}$ to $L^{35}$ and $X^3$) or bonding groups $Z^{31}$ to $Z^{33}$ on the properties of compound 3 are described below.

When $R^3$ in formula (3) is alkenyl, with regard to a preferred configuration of —CH═CH— in the alkenyl, the preferred configuration of —CH═CH— in $R^1$ in formula (1) is correspondingly applied thereto.

When bonding groups $Z^{31}$, $Z^{32}$ and $Z^{33}$ in formula (3) are a single bond or —$CF_2O$—, viscosity is small. When bonding groups $Z^{31}$, $Z^{32}$ and $Z^{33}$ are —$CF_2O$—, dielectric anisotropy is large. When bonding groups $Z^{31}$, $Z^{32}$ and $Z^{33}$ in formula (3) are a single bond or —$CF_2O$—, the compound is relatively chemically stable and relatively hard to cause deterioration.

When right-terminal group $X^3$ in formula (3) is fluorine, chlorine, —$SF_5$, —$CF_3$, —$CHF_2$, —$CH_2F$, —$OCF_3$, —$OCHF_2$ or —$OCH_2F$, the dielectric anisotropy is large. When $X^3$ is fluorine, —$OCF_3$ or —$CF_3$, the compound is chemically stable.

In formula (3), when the number of fluorine in $L^{31}$ to $L^{35}$ is large, the dielectric anisotropy is large. When $L^{31}$ is hydrogen, compatibility with other liquid crystals is excellent. When both $L^{34}$ and $L^{35}$ are fluorine, the dielectric anisotropy is particularly large.

As described above, the compound having objective physical properties can be obtained by suitably selecting kinds of the terminal group, the bonding group or the like.

2-4-1 Compound 4

The achiral component according to the invention may further contain, in addition to compound 1, at least one compound 4 represented by formula (4). More specifically, in achiral component T, the invention includes a case where the achiral component is formed of one compound as compound 4, and also a case where the achiral component contains a plurality of compounds represented by formula (4) as compound 4. Moreover, for example, the liquid crystal composition according to the invention may contain, in addition to compound 1 and compound 4, at least one compound selected from the group of compounds 2, 3 and 5 to 7.

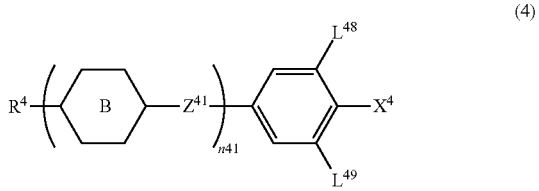

(4)

$R^4$ in formula (4) is alkyl having 1 to 12 carbons, alkoxy having 1 to 12 carbons, alkenyl having 2 to 12 carbons or alkenyl having 2 to 12 carbons in which at least one of hydrogen is replaced by fluorine. Preferred $R^4$ in formula (4) is alkyl having 1 to 12 carbons in order to improve stability to ultraviolet light or stability to heat. In view of reducing viscosity, $R^4$ in formula (4) is preferably alkenyl having 2 to 12 carbons, and in view of improving the stability to ultraviolet light or the stability to heat, is preferably alkyl having 1 to 12 carbons.

Preferred alkyl in $R^4$ in formula (4) is methyl, ethyl, propyl, butyl, pentyl, hexyl, heptyl or octyl, and further preferred alkyl is ethyl, propyl, butyl, pentyl or heptyl in order to reduce viscosity.

Preferred alkoxy in $R^4$ in formula (4) is methoxy, ethoxy, propoxy, butoxy, pentyloxy, hexyloxy or heptyloxy, and further preferred alkoxy is methoxy or ethoxy in order to reduce viscosity.

Preferred alkenyl in $R^4$ in formula (4) is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl, and further preferred alkenyl is vinyl, 1-propenyl, 3-butenyl or 3-pentenyl in order to reduce the viscosity.

With regard to a preferred configuration of —CH═CH— in the alkenyl in $R^4$ in formula (4), the preferred configuration of —CH═CH— in $R^1$ in formula (1) is correspondingly applied thereto. Trans is preferred in alkenyl such as 1-propenyl, 1-butenyl, 1-pentenyl, 1-hexenyl, 3-pentenyl and 3-hexenyl in order to reduce the viscosity. Cis is preferred in alkenyl such as 2-butenyl, 2-pentenyl and 2-hexenyl. In the alkenyl, straight-chain alkenyl is preferred to branched-chain alkenyl.

In $R^4$ in formula (4), specific preferred examples of alkenyl in which at least one of hydrogen is replaced by fluorine include 2,2-difluorovinyl, 3,3-difluoro-2-propenyl, 4,4-difluoro-3-butenyl, 5,5-difluoro-4-pentenyl and 6,6-difluoro-5-hexenyl, and 2,2-difluorovinyl and 4,4-difluoro-3-butenyl are preferred in order to reduce the viscosity of the liquid crystal composition.

The alkyl in $R^4$ in formula (4) includes no cyclic alkyl. The alkoxy includes no cyclic alkoxy. The alkenyl includes no cyclic alkenyl. The alkenyl in which at least one of hydrogen is replaced by fluorine includes no cyclic alkenyl in which at least one of hydrogen is replaced by fluorine.

Then, n41 in formula (4) is 1, 2, 3 or 4, in which, when n41 is 3 or 4, at least one of $Z^{41}$ is —CF$_2$O— or —OCF$_2$—, and when n41 is 3, a case where all of ring B is 1,4-phenylene replaced by fluorine is excluded.

Ring B in formula (4) is independently 1,4-cyclohexylene, 1,4-phenylene, 2-fluoro-1,4-phenylene, 3-fluoro-1,4-phenylene, 3,5-difluoro-1,4-phenylene, 3,5-dichloro-1,4-phenylene or pyrimidine 2,5-diyl, and when n41 is 2 or more, at least two of ring B may be identical or different. Ring B in formula (4) is preferably 1,4-phenylene or 3-fluoro-1,4-phenylene in order to improve optical anisotropy, and 1,4-cyclohexylene in order to reduce the viscosity.

$Z^{41}$ in formula (4) is independently a single bond, ethylene, —COO—, —OCO—, —CF$_2$O— or —OCF$_2$—, in which, when n41 is 3 or 4, one of $Z^{12}$ is —CF$_2$O—. When n41 is 2 or more, at least two of $Z^{12}$ may be identical or different. $Z^{41}$ in formula (4) is preferably a single bond in order to reduce the viscosity. $Z^{41}$ in formula (4) is preferably —CF$_2$O— in order to improve the dielectric anisotropy and achieve good compatibility.

$L^{48}$ and $L^{49}$ in formula (4) are independently hydrogen or fluorine, both $L^{48}$ and $L^{49}$ are preferably fluorine in order to improve the dielectric anisotropy, and both $L^{48}$ and $L^{49}$ are preferably hydrogen in order to raise the clearing point.

$X^4$ in formula (4) is fluorine, chlorine, —CF$_3$ or —OCF$_3$. $X^4$ is preferably —CF$_3$ in order to improve the dielectric anisotropy, preferably fluorine in order to achieve good compatibility and preferably chlorine in order to improve the refractive index anisotropy.

In compound 4, compounds represented by formula (4-1) to (4-9) are preferably used.

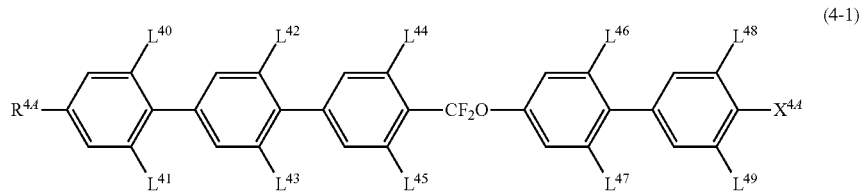

(4-1)

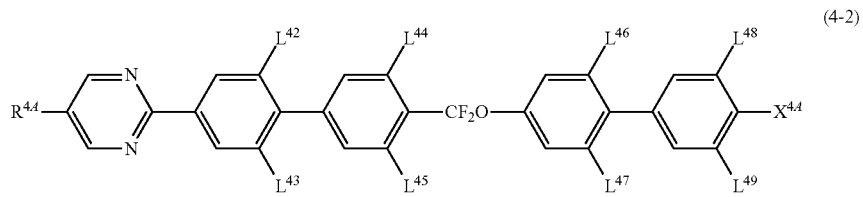

(4-2)

-continued

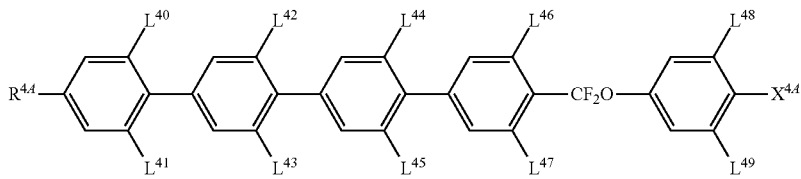
(4-3)

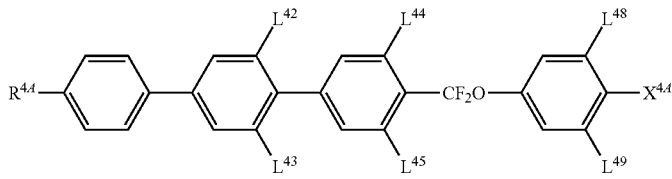
(4-4)

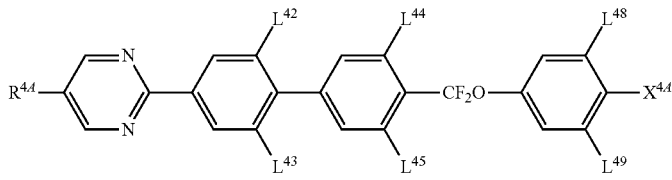
(4-5)

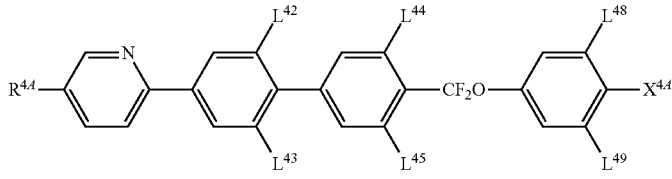
(4-6)

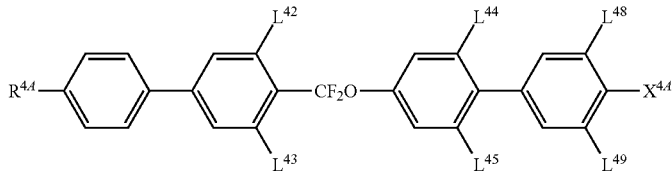
(4-7)

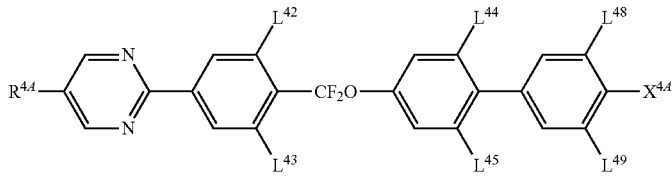
(4-8)

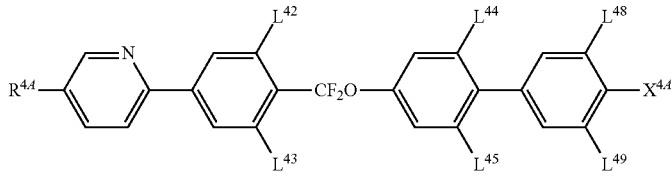
(4-9)

In formulas (4-1) to (4-9) described above, $R^{4A}$ is independently alkyl having 1 to 12 carbons, alkoxy having 1 to 12 carbons, alkenyl having 2 to 12 carbons, or alkenyl having 2 to 12 carbons in which at least one of hydrogen is replaced by fluorine, $X^{4A}$ is fluorine, chlorine, —$CF_3$ or —$OCF_3$, and $L^{40}$ to $L^{49}$ are independently hydrogen or fluorine.

Compounds represented by formulas (4-1) to (4-3) have a high clearing point and excellent compatibility as a compound having five rings. Compounds represented by formulas (4-4) to (4-6) have a high clearing point, large Δn, and compounds represented by formulas (4-7) to (4-9) have excellent compatibility. In addition, in $L^{40}$ to $L^{49}$, accordingly as the number of fluorine is larger, the dielectric anisotropy is larger.

Compound 4 is suitable for preparing a composition having a large dielectric anisotropy or good compatibility at a low temperature. The composition preferably contains compound 4 in a total amount of preferably 5% by weight to 40% by weight, further preferably 5% by weight to 30% by weight, and particularly preferably 5% by weight to 20% by weight, based on the total weight of achiral component T.

2-5-1 Compound 5

The achiral component according to the invention may further contain, in addition to compound 1, at least one compound 5 represented by formula (5). More specifically, in achiral component T, the invention includes a case where the achiral component is formed of one compound as compound 5, and also a case where the achiral component contains a plurality of compounds represented by formula (5) as compound 5. Moreover, for example, the liquid crystal composition according to the invention may contain, in addition to compound 1 and compound 5, at least one compound selected from the group of compounds 2 to 4, 6 and 7.

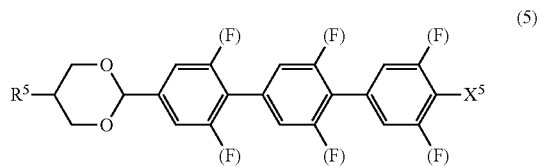

(in formula(5), $R^5$ is hydrogen or alkyl having 1 to 20 carbons, at least one of —$CH_2$— in the alkyl may be replaced by —O—, —S—, —COO— or —OCO—, at least one of —$CH_2$—$CH_2$— in the alkyl may be replaced by —CH=CH—, —CF=CF— or —C≡C—, and at least one of hydrogen in the alkyl may be replaced by fluorine or chlorine, in which, in $R^5$, neither —O— and —CH=CH— nor —CO— and —CH=CH— are adjacent;

(F) is independently hydrogen or fluorine; and $X^5$ is hydrogen, halogen, —$SF_5$ or alkyl having 1 to 10 carbons, at least one of —$CH_2$— in the alkyl may be replaced by —O—, —S—, —COO— or —OCO—, at least one of —$CH_2$—$CH_2$— in the alkyl and in a group in which —$CH_2$— in the alkyl is replaced by —O—, —S—, —COO— or —OCO— may be replaced by —CH=CH—, —CF=CF— or and at least one of hydrogen in the alkyl, in the group in which —$CH_2$— in the alkyl is replaced by —O—, —S—, —COO— or —OCO—, or in a group in which at least one of —$CH_2$—$CH_2$— in the alkyl is replaced by —CH=CH— or —C≡C— may be replaced by fluorine or chlorine, in which, in $X^5$, neither —O— nor —CH=CH— is adjacent, and neither —CO— nor —CH=CH— is adjacent.)

With regard to a preferred configuration of —CH=CH— in the alkenyl in $R^5$ in formula (5), the preferred configuration of —CH=CH— in $R^1$ in formula (1) is correspondingly applied thereto.

In $R^5$ and $X^5$ in formula (5), specific examples of alkyl in which at least one of hydrogen is replaced by fluorine include —$CHF_2$, —$CF_3$, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$ and —$CHFCF_2CF_3$.

In $R^5$ and $X^5$ in formula (5), specific examples of alkoxy in which at least one of hydrogen is replaced by fluorine include —$OCHF_2$, —$OCF_3$, —$OCF_2CH_2F$, —$OCF_2CHF_2$, —$OCH_2CF_3$, —O—$(CF_2)_3$—F, —$OCF_2CHFCF_3$ and —$OCHFCF_2CF_3$.

In $R^5$ and $X^5$ in formula (5), specific examples of alkenyl in which at least one of hydrogen is replaced by fluorine include —CH=$CF_2$, —CF=CHF, —CH=$CHCH_2F$, —CH=$CHCF_3$, —$(CH_2)_2$—CH=$CF_2$, —$CH_2$CH=$CHCF_3$ and —CH=$CHCF_2CF_3$.

Specific examples of $X^5$ in formula (5) include fluorine, chlorine, —$CF_3$, —$CHF_2$, —$OCF_3$ and —$OCHF_2$, and preferably fluorine, chlorine, —$CF_3$ and —$OCF_3$. When $X^5$ in formula (5) is chlorine or fluorine, a melting point of compound 5 is relatively low, and compatibility with other liquid crystal compounds is particularly excellent. When $X^5$ in formula (5) is —$CF_3$, —$CHF_2$, —$OCF_3$ and —$OCHF_2$, compound 5 exhibits a relatively large dielectric anisotropy. When $X^5$ in formula (5) is fluorine, chlorine, —$SF_5$, —$CF_3$, —$OCF_3$ or —CH=CH—$CF_3$, dielectric anisotropy of compound 5 is relatively large, and when $X^5$ is fluorine, —$CF_3$ or —$OCF_3$, the compound is relatively chemically stabilized.

In compound 5, compounds represented by formulas (5-1) to (5-4) are preferably used, and compounds represented by formulas (5-1) to (5-3) are further preferably used. Among the compounds, compounds represented by formulas (5-1-1), (5-1-2), (5-2-1) to (5-2-4), (5-3-1) and (5-3-2) are particularly preferred, and compounds represented by formulas (5-2-2) and (5-3-2) are most preferred.

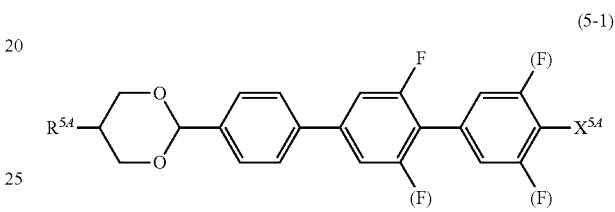

(5-1)

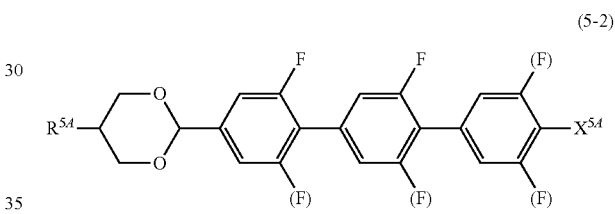

(5-2)

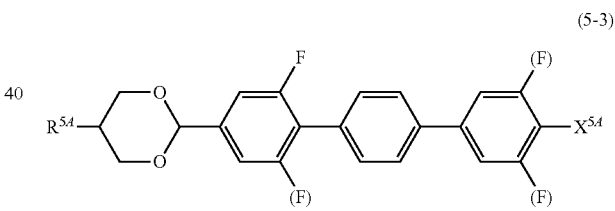

(5-3)

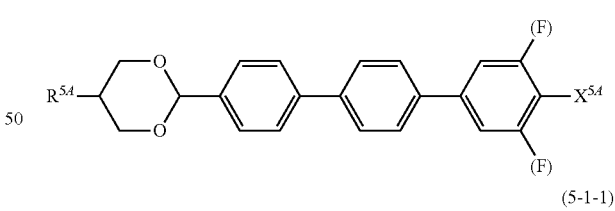

(5-4)

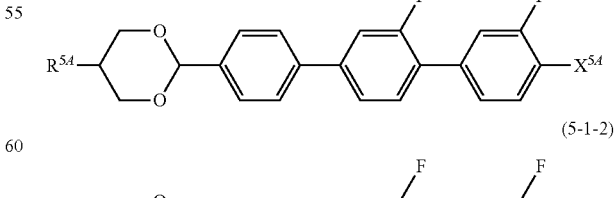

(5-1-1)

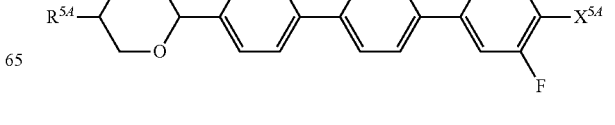

(5-1-2)

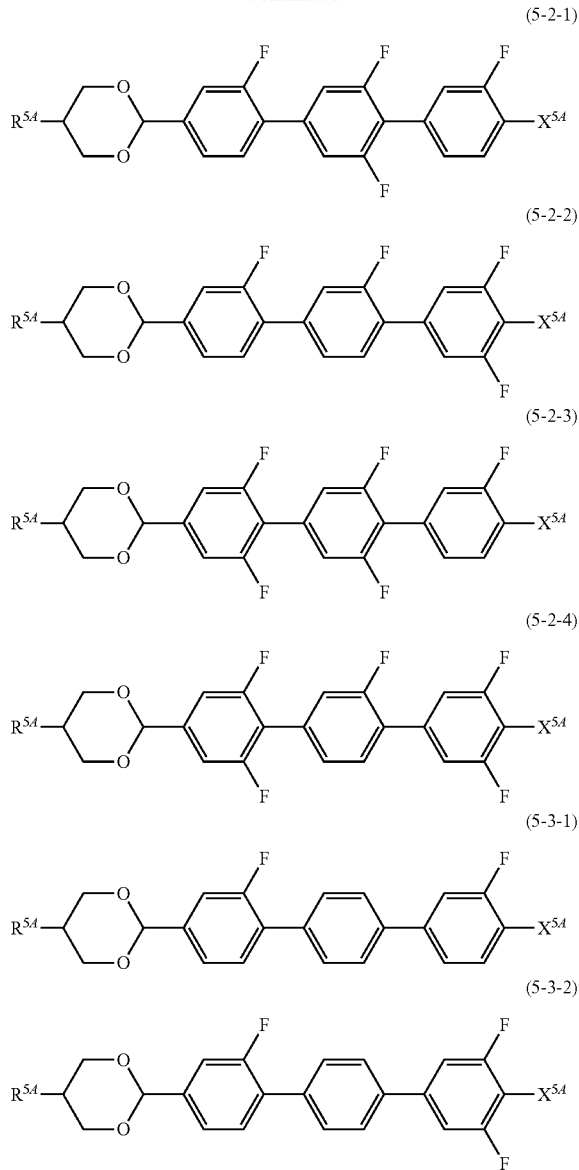

(in the formulas, $R^{5a}$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine;

(F) is each independently hydrogen or fluorine; and $X^{5A}$ is fluorine, chlorine, —$CF_3$ or —$OCF_3$.)

Compound 5 is suitable for preparing a composition having a large dielectric anisotropy.

In order to raise the clearing point, the composition preferably contains compound 5 in a total amount of 1.0% by weight or more based on the total weight of achiral component T. Moreover, in order to decrease a minimum temperature of the liquid crystal phase, the composition preferably contains compound 5 in a total amount of 1% to 50% by weight based on the total weight of achiral component T. Further, the composition contains compound 5 in an amount of preferably 1% to 25% by weight, and further preferably 1% to 15% by weight, based on the total weight of achiral component T.

2-5-2 Properties of Compound 5

Compound 5 has a dioxane ring and three benzene rings. Compound 5 is significantly physically and chemically stable under conditions in which the device is ordinarily used, and has a relatively good compatibility with other liquid crystal compounds even though the clearing point is high. A composition containing compound 5 is stable under the conditions in which the device is ordinarily used. Accordingly, a temperature range of the optically isotropic liquid crystal phase can be extended in the composition containing compound 5, and the composition can be used in the form of a display device in a wide temperature range. Moreover, compound 5 is useful as a component for decreasing the driving voltage of the composition to be driven in the optically isotropic liquid crystal phase. Moreover, if a blue phase is developed by the composition in a preferred aspect containing the chiral agent and compound 5, a uniform blue phase without coexistence of an N*phase or an isotropic phase is formed. Thus, the composition in the preferred aspect containing compound 5 easily develops the uniform blue phase. Moreover, if compound 5 is used, the clearing point of the liquid crystal composition tents to be increased.

2-5-3 Synthesis of Compound 5

Next, synthesis of compound 5 is described. Compound 5 can be prepared by suitably combining techniques in synthetic organic chemistry. Methods for introducing an objective terminal group, ring and bonding group into a starting material are described in Organic Syntheses (John Wiley & Sons, Inc.), Organic Reactions (John Wiley & Sons, Inc.), Comprehensive Organic Synthesis (Pergamon Press), New Experimental Chemistry Course (Shin Jikken Kagaku Koza in Japanese) (Maruzen Co., Ltd.), or the like.

For example, the compound represented by formula (5) according to the present application can also be prepared even by correspondingly applying the method described in JP 2959526 B thereto.

2-6-1 Compound 6

The achiral component according to the invention may further contain, in addition to compound 1, at least one compound 6 represented by formula (6). More specifically, in achiral component T, the invention includes a case where the achiral component is formed of one compound as compound 6, and also a case where the achiral component contains a plurality of compounds represented by formula (6) as compound 6. Moreover, for example, the liquid crystal composition according to the invention may contain, in addition to compound 1 and compound 6, at least one compound selected from the group of compounds 2 to 5, and 7. Compound 6 has a small absolute value of dielectric anisotropy, and is a compound close to neutrality.

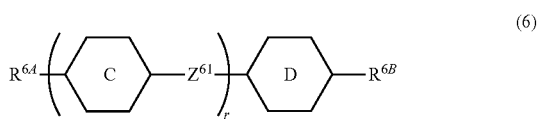

(6)

Then, r in formula (6) is 1, 2 or 3. A compound in which r is 1 in formula (6) is effective mainly in adjusting the viscosity or a refractive index anisotropy value, and a compound in which r is 2 or 3 in formula (6) is effective in extending the temperature range of the optically isotropic liquid crystal phase, such as raising the clearing point, or in adjusting the refractive index anisotropy value.

When a content of the compound represented by formula (6) is increased, the driving voltage of the liquid crystal composition increases and the viscosity decreases. Therefore, as long as a desired value of the viscosity of the liquid crystal composition is satisfied, the content is desirably as small as possible from a viewpoint of driving voltage. As a content of compound 6 in achiral component T, the composition preferably contains compound 6 in an amount of preferably 0% by weight to 40% by weight, further preferably 1% by weight to 40% by weight, and particularly preferably 1% by weight to 20% by weight, based on the total weight of the achiral component T.

$R^{6A}$ and $R^{6B}$ in formula (6) are each independently alkyl having 1 to 12 carbons, alkoxy having 1 to 12 carbons, alkenyl having 2 to 12 carbons or alkenyl having 2 to 12 carbons in which at least one of hydrogen is replaced by fluorine. In order to reduce the viscosity of compound 6, $R^{6A}$ and $R^{6B}$ in formula (6) are preferably alkenyl having 2 to 12 carbons. In order to improve stability to ultraviolet light or heat, $R^{6A}$ and $R^{6B}$ in formula (6) are preferably alkyl having 1 to 12 carbons.

In $R^{6A}$ and $R^{6B}$ in formula (6), alkyl is preferably methyl, ethyl, propyl, butyl, pentyl, hexyl, heptyl or octyl, and preferably ethyl, propyl, butyl, pentyl or heptyl in order to reduce the viscosity.

In $R^{6A}$ and $R^{6B}$ in formula (6), alkoxy is preferably methoxy, ethoxy, propoxy, butoxy, pentyloxy, hexyloxy or heptyloxy, and preferably methoxy or ethoxy in order to reduce the viscosity.

In $R^{6A}$ and $R^{6B}$ in formula (6), with regard to a preferred configuration of —CH=CH— in the alkenyl, the preferred configuration of —CH=CH— in $R^1$ in formula (1) is correspondingly applied thereto.

In $R^{6A}$ and $R^{6B}$ in formula (6), alkenyl in which at least one of hydrogen is replaced by fluorine is preferably 2,2-difluorovinyl, 3,3-difluoro-2-propenyl, 4,4-difluoro-3-butenyl, 5,5-difluoro-4-pentenyl and 6,6-difluoro-5-hexenyl. In order to reduce the viscosity of the composition containing compound 6, $R^{6A}$ and $R^{6B}$ are preferably 2,2-difluorovinyl and 4,4-difluoro-3-butenyl.

Ring C and ring D in formula (6) are independently 1,4-cyclohexylene, 1,4-phenylene, 2-fluoro-1,4-phenylene, 3-fluoro-1,4-phenylene or 2,5-difluoro-1,4-phenylene, and when r is 2 or more, at least two of ring C may be identical or different. In order to improve the optical anisotropy of compound 6, ring C and ring D are preferably 1,4-phenylene or 3-fluoro-1,4-phenylene. In order to reduce the viscosity of compound 6, ring C and ring D are preferably 1,4-cyclohexylene.

$Z^{61}$ in formula (6) is each independently a single bond, ethylene, —COO— or —OCO—, and when r is 2 or more, at least two of $Z^{13}$ may be identical or different. Preferred $Z^{61}$ is a single bond in order to reduce the viscosity.

In compound 6, compounds represented by formulas (6-1) to (6-13) are preferably used.

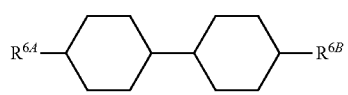

(6-1)

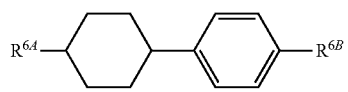

(6-2)

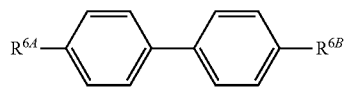

(6-3)

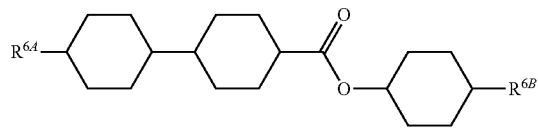

(6-4)

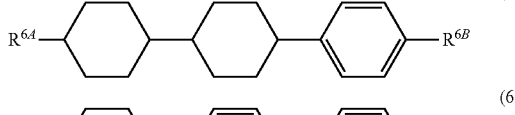

(6-5)

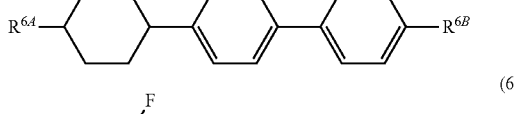

(6-6)

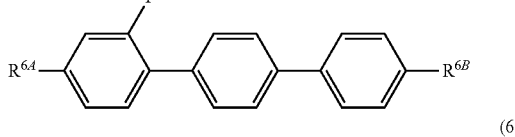

(6-7)

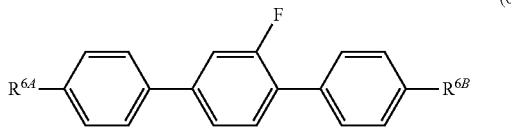

(6-8)

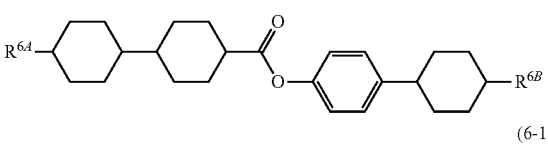

(6-9)

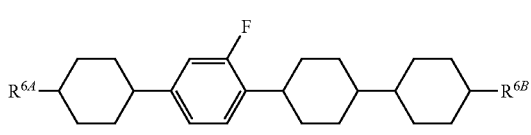

(6-10)

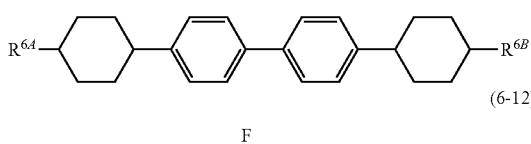

(6-11)

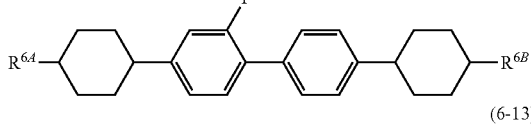

(6-12)

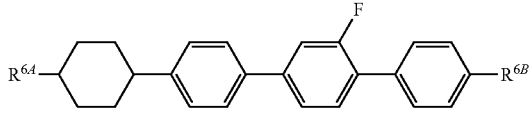

(6-13)

Among the compounds, compounds represented by (6-1) to (6-3) have a relatively low viscosity, compounds represented by (6-4) to (6-8) have a relatively high clearing point and compounds represented by (6-9) to (6-13) have a relatively high clearing point.

Compound 6 is used in order to reduce the viscosity or to raise the clearing point, when necessary. However, compound 6 raises the driving voltage, and therefore when the driving voltage is considered to be important, compound 6 is preferably not used or is used in a small amount. The composition contains compound 6 in a total amount of preferably 0% by weight to 30% by weight, further preferably 0% by weight to 20% by weight and particularly preferably 0% by weight to 10% by weight.

2-7-1 Compound 7

The achiral component according to the invention may further contain, in addition to compound 1, at least one compound 7 represented by formula (7). More specifically, in achiral component T, the invention includes a case where the achiral component is formed of one compound as compound 7, and also a case where the achiral component contains a plurality of compounds represented by formula (7) as compound 7. Moreover, for example, the liquid crystal composition according to the invention may contain, in addition to compound 1 and compound 7, at least one compound selected from the group of compounds 2 to 6.

compounds represented by formulas (7-2-1) to (7-2-5) are still further preferably used, and compounds represented by formulas (7-2-2-E), (7-2-5-E), (7-2-2-F) and (7-2-5-F) are particularly preferably used.

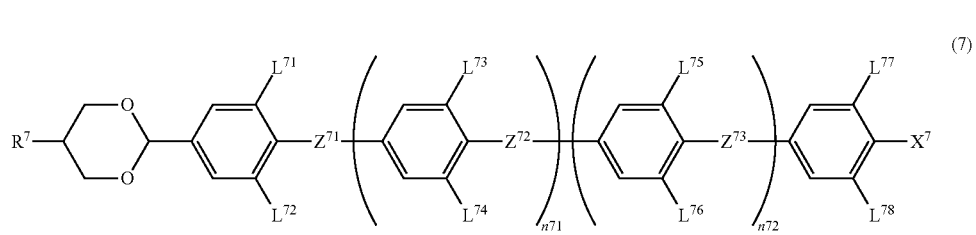

(7-1-1)

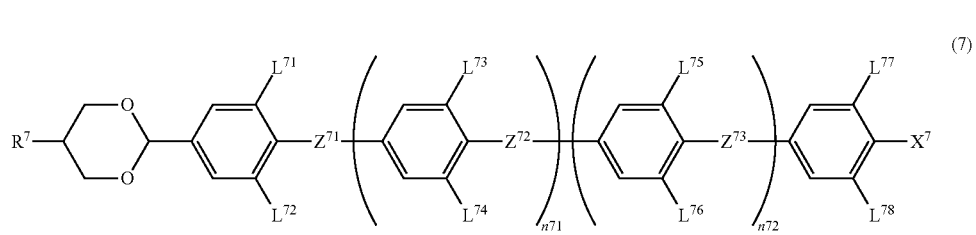

(7)

With regard to a preferred configuration of —CH═CH— in the alkenyl in $R^7$ and $X^7$ in formula (7), the preferred configuration of —CH═CH— in $R^1$ in formula (1) is correspondingly applied thereto.

Specific examples of alkyl in which at least one of hydrogen is replaced by fluorine in $X^7$ in formula (7) include —CHF$_2$, —CF$_3$, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$ and —CHFCF$_2$CF$_3$.

Specific examples of alkoxy in which at least one of hydrogen is replaced by fluorine in $X^7$ in formula (7) include —OCHF$_2$, —OCF$_3$, —OCF$_2$CH$_2$F, —OCF$_2$CHF$_2$, —OCH$_2$CF$_3$, —O—(CF$_2$)$_3$—F, —OCF$_2$CHFCF$_3$ and —OCHFCF$_2$CF$_3$.

Specific examples of alkenyl in which at least one of hydrogen is replaced by fluorine in $X^7$ in formula (7) include —CH═CF$_2$, —CF═CHF, —CH═CHCH$_2$F, —CH═CHCF$_3$, —(CH$_2$)$_2$—CH═CF$_2$, —CH$_2$CH═CHCF$_3$ and —CH═CHCF$_2$CF$_3$.

In formula (7), specific examples of $X^7$ include fluorine, chlorine, —CF$_3$, —CHF$_2$, —OCF$_3$ and —OCHF$_2$, and further preferably fluorine, chlorine, —CF$_3$ and —OCF$_3$.

When $X^7$ in formula (7) is chlorine or fluorine, a melting point of compound 7 is relatively low, and compatibility with other liquid crystal compounds is particularly excellent. When $X^7$ in formula (7) is —CF$_3$, —SF$_5$, —CHF$_2$, —OCF$_3$ and —OCHF$_2$, compound 7 exhibits a relatively large dielectric anisotropy.

When $X^7$ is fluorine, —CF$_3$ or —OCF$_3$, the compound is chemically stable.

In compound 7, compounds represented by formulas (7-1) to (7-8) are preferably used, compounds represented by formulas (7-1-1), (7-1-2), (7-2-1) to (7-2-5), (7-3-1), (7-3-2), (7-4-1), (7-5-1) and (7-5-2) are further preferably used, -continued

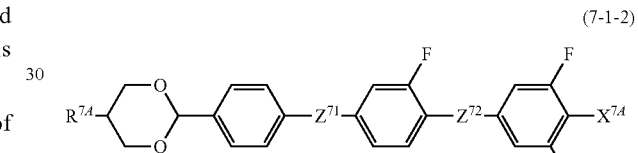

(7-1-2)

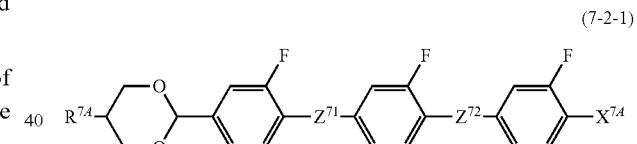

(7-2-1)

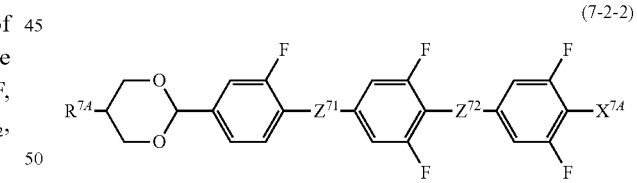

(7-2-2)

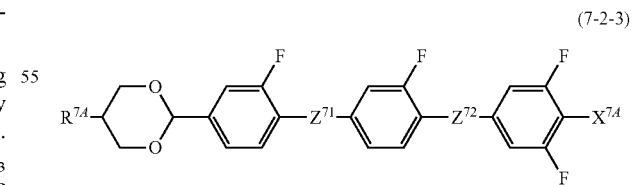

(7-2-3)

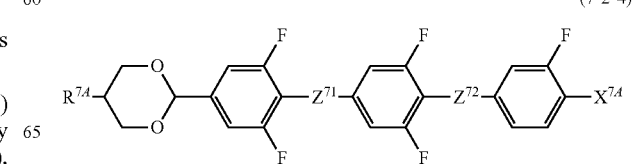

(7-2-4)

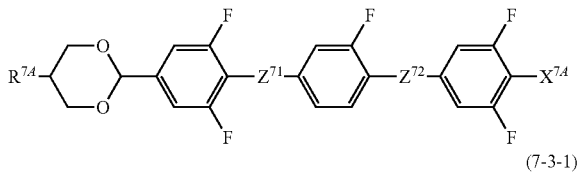
(7-2-5)

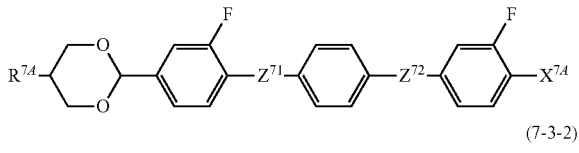
(7-3-1)

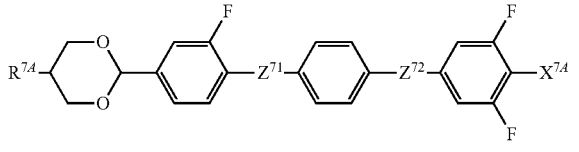
(7-3-2)

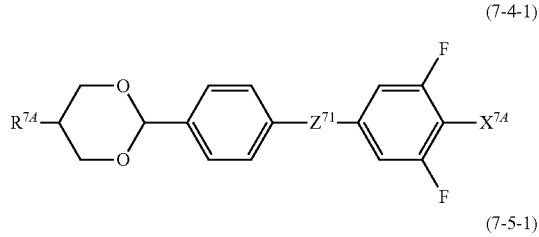
(7-4-1)

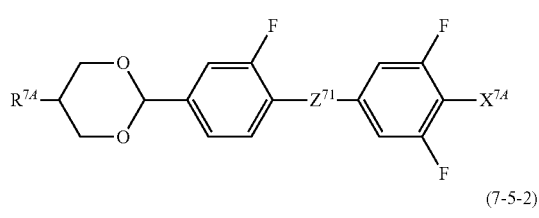
(7-5-1)

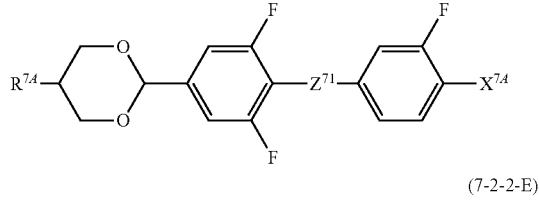
(7-5-2)

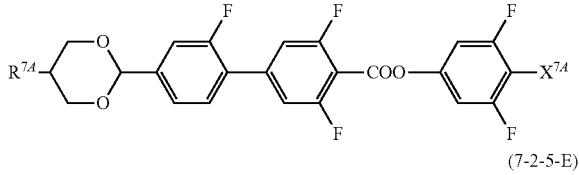
(7-2-2-E)

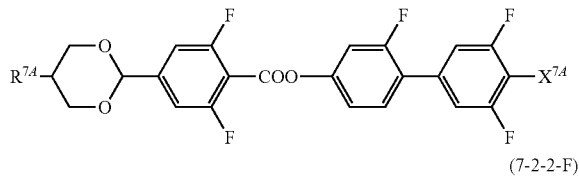
(7-2-5-E)

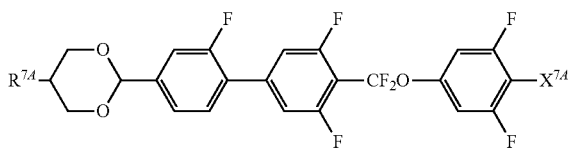
(7-2-2-F)

(7-2-5-F)

In the formulas, $R^{7A}$ is alkyl having 2 to 12 carbons, alkoxy having 1 to 11 carbons, alkenyl having 2 to 12 carbons, or alkenyl having 2 to 12 carbons in which at least one of hydrogen is replaced by fluorine;

in formulas (7-1-1), (7-1-2), (7-2-1) to (7-2-5), (7-3-1) and (7-3-2), $Z^{71}$ and $Z^{72}$ are each independently a single bond, —COO or —CF$_2$O—, but at least one is —COO or —CF$_2$O—, and in formulas (7-4-1), (7-5-1) and (7-5-2), Z71 is —COO or —CF$_2$O—; and $X^{7A}$ is fluorine, chlorine, —CF$_3$ or —OCF$_3$.

Compound 7 is suitable for preparing a composition having a large dielectric anisotropy, and can reduce the driving voltage of the device according to the invention. The composition contains compound 7 in a total amount of preferably 5% by weight to 80% by weight, further preferably 20% by weight to 75% by weight, and particularly preferably 30% by weight to 70% by weight, based on the total weight of the achiral component T.

2-7-2 Properties of Compound 7

Compound 7 has a dioxane ring and three benzene rings, and at least one of —CF$_2$O—. Compound 7 is significantly physically and chemically stable under conditions in which the device is ordinarily used, and has a relatively good compatibility with other liquid crystal compounds even though the clearing point is high. A composition containing compound 7 is stable under the conditions in which the device is ordinarily used. Accordingly, a temperature range of the optically isotropic liquid crystal phase can be extended in the composition containing compound 7, and the composition can be used in the form of a display device in a wide temperature range. Further, compound 7 is useful as a component for decreasing the driving voltage of the composition to be driven in the optically isotropic liquid crystal phase. Moreover, if a blue phase is developed by the composition containing the chiral agent and compound 7, a uniform blue phase without coexistence of an N*phase or an isotropic phase is easily formed. More specifically, compound 7 is a compound that easily develops the uniform blue phase. Moreover, compound 7 develops a significantly large dielectric anisotropy.

2-7-3 Synthesis of Compound 7

Compound 7 can be prepared by suitably combining techniques in synthetic organic chemistry. Methods for introducing an objective terminal group, ring and bonding group into a starting material are described in Organic Syntheses (John Wiley & Sons, Inc.), Organic Reactions (John Wiley & Sons, Inc.), Comprehensive Organic Synthesis (Pergamon Press), New Experimental Chemistry Course (Shin Jikken Kagaku Koza in Japanese) (Maruzen Co., Ltd.), or the like.

Optically Isotropic Liquid Crystal Composition

A liquid crystal composition according to the invention contains achiral component T and the chiral agent to include an aspect of the composition that develops the optically isotropic liquid crystal phase (optically isotropic liquid crystal composition).

Achiral component T contained in the optically isotropic liquid crystal composition according to the invention contains compound 1, and when necessary, at least one compound selected from the group of compounds 2 to 7. Achiral component T preferably contains, in addition to compound 1, compounds 2, 3, 5 and 7, and particularly preferably contains compounds 3 and 7, and can further contain compounds 4 and 6 according to desired properties.

Compound 1 simultaneously has a relatively high clearing point, a relatively large dielectric anisotropy and a relatively good compatibility at low temperature, and therefore the liquid crystal composition that uses compound 1 and develops the optical isotropy also develops the high clearing point, a wide liquid crystal phase temperature range or a large dielectric anisotropy, and therefore is useful as the composition used in the optical device. The optically isotropic liquid crystal composition containing compound 1 simultaneously develops the high clearing point and a low driving voltage.

Further, in order to develop the large dielectric anisotropy, further addition of compounds represented by compounds 3 and 7 is preferred. The composition develops a significantly large dielectric anisotropy, and therefore is significantly effective in achieving voltage reduction of the optical device.

Chiral Agent

The chiral agent contained in the optically isotropic liquid crystal composition according to the invention or the like is an optically active compound, and is preferably formed of a compound selected from compounds having no radically polymerizable group.

As the chiral agent used for the liquid crystal composition according to the invention, a compound having large helical twisting power is preferred. The compound having large helical twisting power can minimize an amount of addition necessary for obtaining a desired pitch, and therefore a rise in the driving voltage can be suppressed, and is advantageous in practical use. Specifically, compounds represented by formulas (K1) to (K6) are preferred. In addition, in (K4) to (K6), a binaphthyl group or an octahydronaphthyl group is an optically active moiety, and a chirality of the chiral agent is not required.

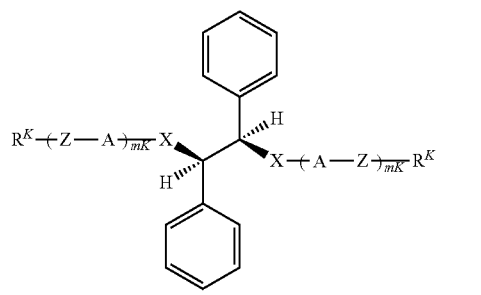
(K1)

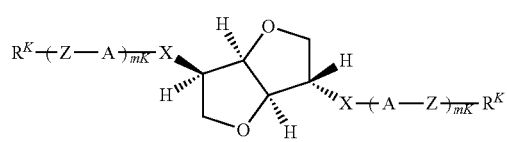
(K2)

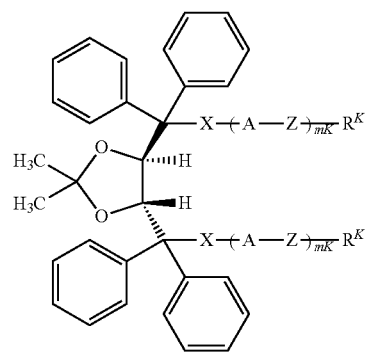
(K3)

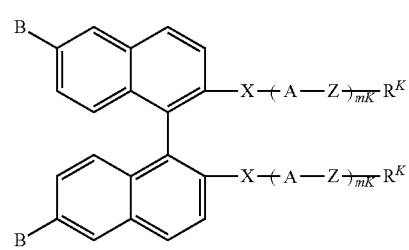
(K4)

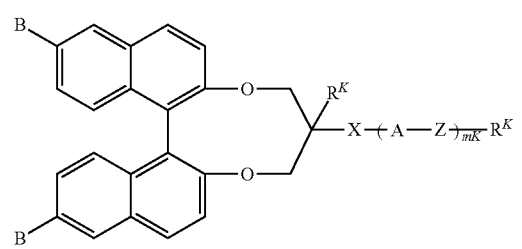
(K5)

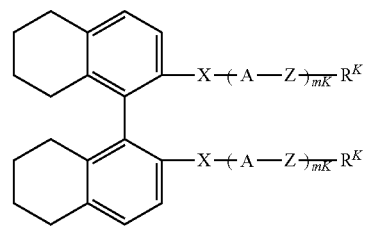
(K6)

Among the compounds, formulas (K4-1) to (K4-6) included in formula (K4), formulas (K5-1) to (K5-3) included in formula (K5) and formulas (K6-1) to (K6-6) included in formula (K6) are preferred, and formula (K4-5), formulas (K5-1) to (K5-3) and formulas (K6-5) to (K6-6) are further preferred as the chiral agent to be added to the liquid crystal composition.

(K4-1)
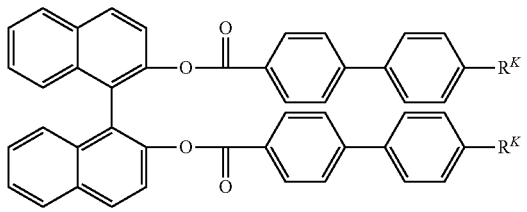
(K4-2)
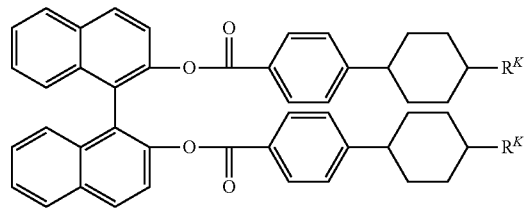
(K4-3)
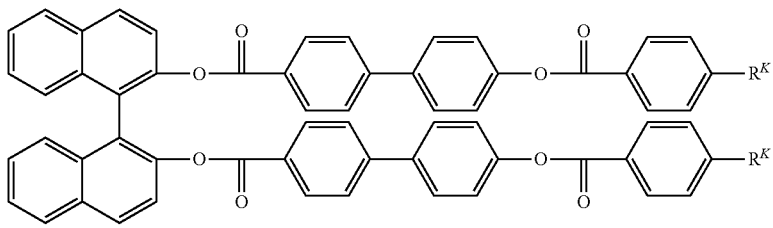
(K4-4)
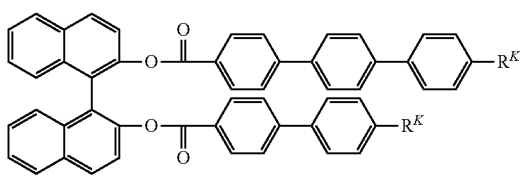
(K4-5)
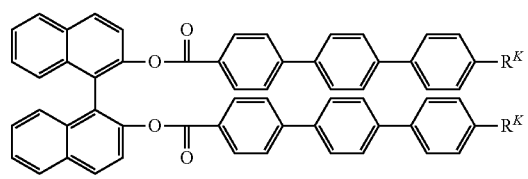
(K4-6)
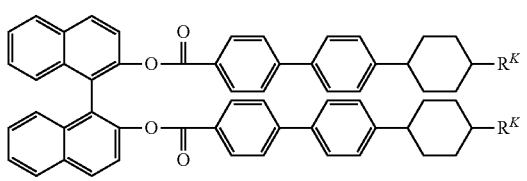
(K5-1)
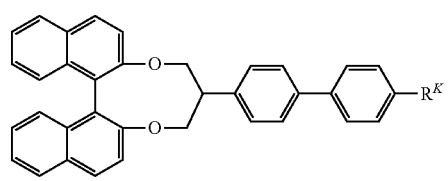
(K5-2)
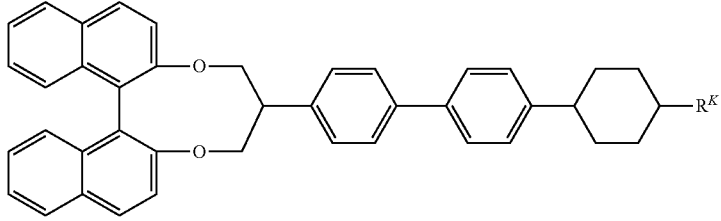
(K5-3)
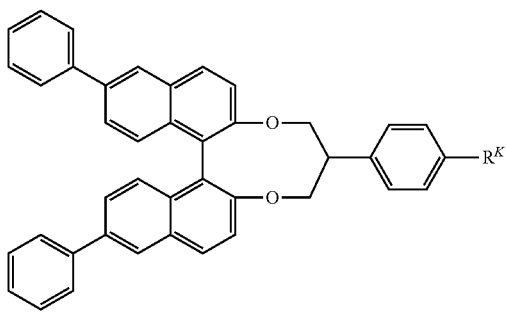
(K6-1)
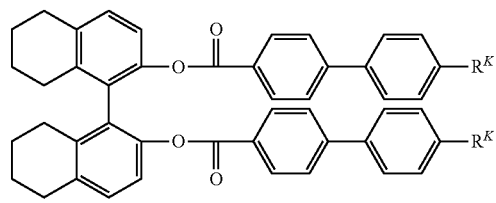
(K6-2)
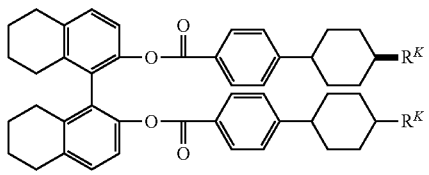
(K6-3)
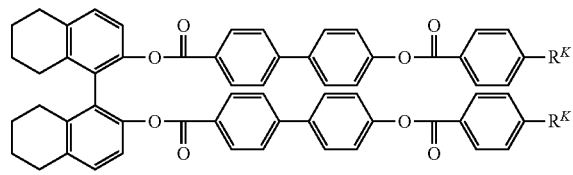

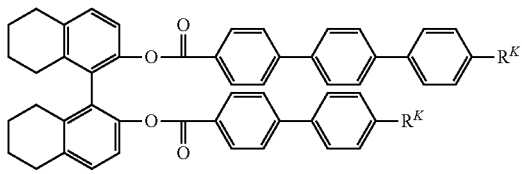
(K6-4)

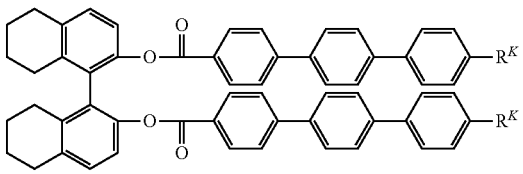
(K6-5)

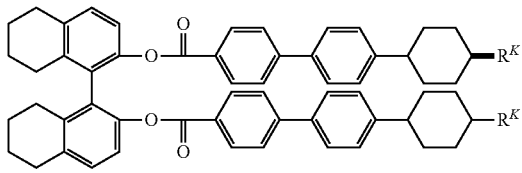
(K6-6)

(In the formulas, $R^K$ is independently alkyl having 3 to 10 carbons or alkoxy having 3 to 10 carbons, and at least one of —CH2-CH2- in the alkyl or alkoxy may be replaced by —CH=CH—.)

Depending on properties required for the liquid crystal composition, the chiral agent having relatively modest helical twisting power is preferably used. Specific examples of the chiral agent having relatively modest helical twisting power include compounds represented by formulas (Op-1) to (Op-13) below.

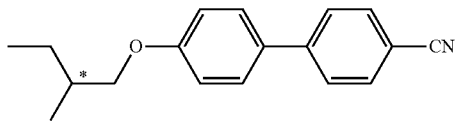
(Op-1)

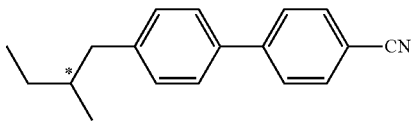
(Op-2)

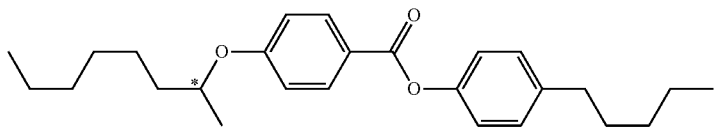
(Op-3)

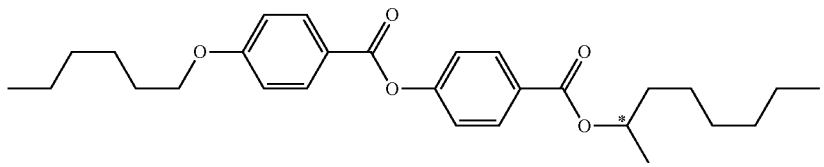
(Op-4)

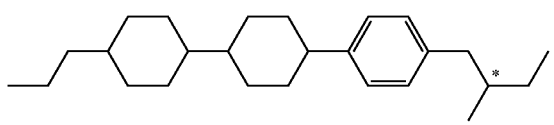
(Op-5)

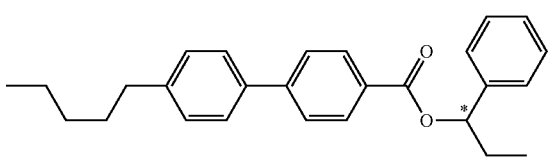
(Op-6)

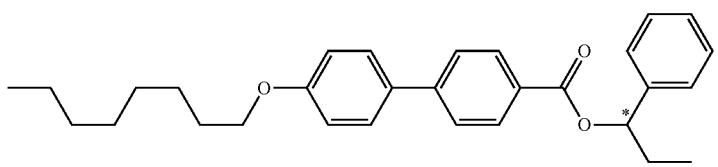
(Op-7)

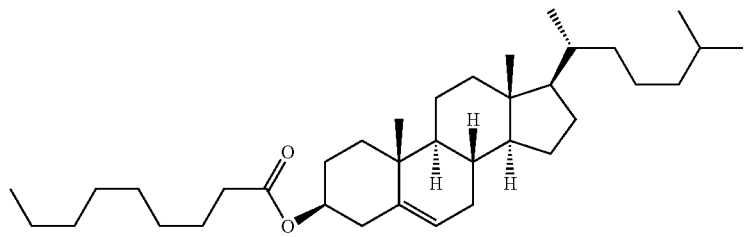

(Op-8)

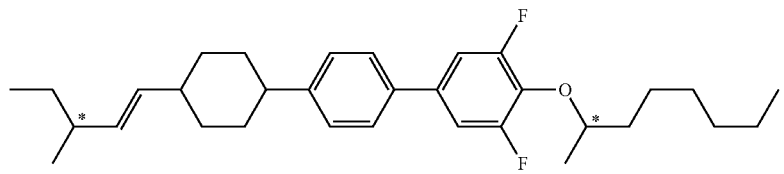

(Op-9)

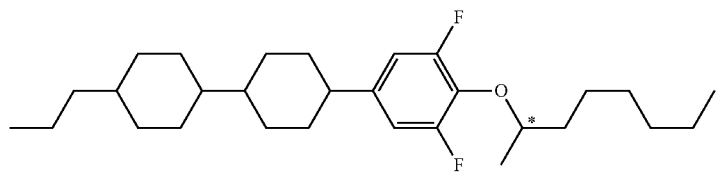

(Op-10)

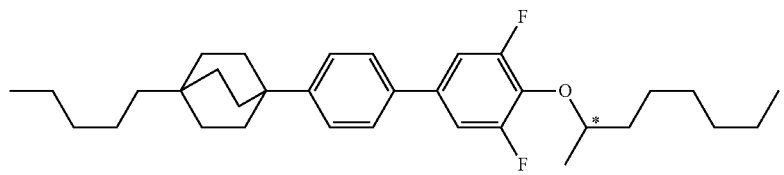

(Op-11)

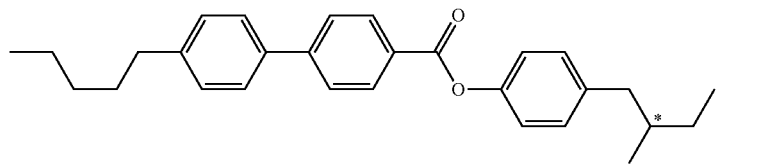

(Op-12)

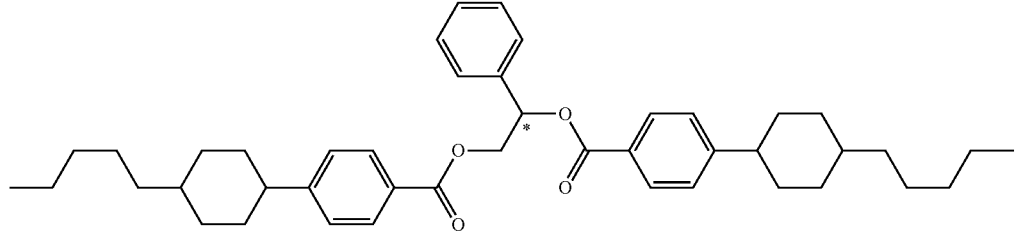

(Op-13)

As the chiral agent contained in the liquid crystal composition, one compound may be used, or a plurality of compounds may be used.

In order to facilitate development of the optically isotropic liquid crystal phase, the liquid crystal composition preferably contains the chiral agent in a total amount of preferably 1% to 40% by weight, further preferably 3% to 25% by weight, and particularly preferably 3% to 15% by weight, based on the total weight of the liquid crystal composition according to the invention.

Optically Isotropic Liquid Crystal Phase

An expression "liquid crystal composition has optical isotropy" herein means that the liquid crystal composition exhibits the optical isotropy macroscopically because alignment of liquid crystal molecules is isotropic, in which liquid crystal order is microscopically present. "Pitch based on the liquid crystal order of the liquid crystal composition microscopically (hereinafter, occasionally referred to as a pitch)" is preferably 700 nanometers or less, further preferably 500 nanometers or less, and most preferably 350 nanometers or less.

"Non-liquid crystal isotropic phase" herein means a generally defined isotropic phase, more specifically, a disordered phase, and an isotropic phase in which, even if an area in which a local order parameter is not zero is produced, the area is caused by a fluctuation. For example, the isotropic phase developed on a side of a higher temperature of the nematic phase corresponds to the non-liquid crystal isotropic phase herein. A similar definition is applied to chiral liquid crystals herein.

"Optically isotropic liquid crystal phase" herein presents a phase that develops the optically isotropic liquid crystal phase, and not by the fluctuation. One example includes a phase that develops a platelet texture (blue phase in a narrow sense).

Unless otherwise noted, the nematic phase herein means the nematic phase including no chiral nematic phase in the narrow sense.

In the optically isotropic liquid crystal composition according to the invention, the platelet texture typical to the blue phase is occasionally not observed under observation by means of a polarizing microscope, although the liquid crystal composition has the optically isotropic liquid crystal phase. Then, the phase that develops the platelet texture is herein referred to as the blue phase, and the optically isotropic liquid crystal phase including the blue phase is referred to as the optically isotropic liquid crystal phase. More specifically, the blue phase is included in the optically isotropic liquid crystal phase.

In general, the blue phases are classified into three kinds, namely, blue phase I, blue phase II and blue phase III, and all of the three kinds of blue phases are optically active, and isotropic. In the blue phase of blue phase I or blue phase II, two or more kinds of diffracted light resulting from Bragg reflection from different lattice planes are observed. The blue phase is generally observed between the non-liquid crystal isotropic phase and a chiral nematic phase.

"State in which the optically isotropic liquid crystal phase does not show diffracted light having two or more colors" means that the optically isotropic liquid crystal phase has almost monochrome in everywhere in which the platelet texture to be observed in blue phase I and blue phase II is not observed. In the optically isotropic liquid crystal phase that shows no diffracted light having two or more colors, uniformity of contrast in the plane is unnecessary.

The optically isotropic liquid crystal phase that shows no diffracted light having two or more colors has advantages in which intensity of reflected light by Bragg reflection is suppressed, or reflection is shifted to a side of a lower wavelength.

Moreover, in a liquid crystal medium that reflects visible light, color may occasionally become a problem when the liquid crystal material is utilized in the form of the display device. However, in the liquid crystals that show no diffracted light having two or more colors, the reflection wavelength is shifted to the side of the lower wavelength. Therefore, reflection of visible light is allowed to disappear by a pitch longer than a pitch of the blue phase in a narrow sense (phase that develops the platelet texture).

In the liquid crystal composition containing achiral component T and the chiral agent according to the invention, the chiral agent is added preferably at a concentration to be 700 nanometers or less in the pitch. In addition, the composition that develops the nematic phase contains compound 1, and when necessary, other components.

Moreover, the optically isotropic liquid crystal composition according to the invention can also be obtained by adding the chiral agent to the composition having the chiral nematic phase and no optically isotropic liquid crystal phase. In addition, the composition having the chiral nematic phase and no optically isotropic liquid crystal phase contains compound 1, the optically active compound, and when necessary, other components. On the above occasion, in order to allow no development of the optically isotropic liquid crystal phase, the chiral agent is added preferably at a concentration to be 700 nanometers in the pitch. Here, as the chiral agent to be added, the compounds represented by formulas (K1) to (K5) being the compounds having large helical twisting power can be used, and compounds represented by formulas (K2-1) to (K2-8), formulas (K4-1) to (K4-6), formulas (K5-1) to (K5-3) or formulas (K6-1) to (K6-6) are further preferably used.

Moreover, the chiral agent to be added may be a compound the helical twisting power of which is modest. Specific examples of such compounds include compounds to be added to the liquid crystal composition for a device (TN mode, STN mode or the like) driven in the nematic phase, specifically, compounds represented by formulas (Op-1) to (Op-13).

The temperature range in which the liquid crystal composition of a preferred aspect according to the invention develops the optically isotropic liquid crystal phase can be extended by adding the chiral agent to the liquid crystal composition in which the temperature range of coexisting the nematic phase or the chiral nematic phase and the isotropic phase is wide to develop optically isotropic liquid crystal phase. For example, a liquid crystal compound having a high clearing point and a liquid crystal compound having a low clearing point are mixed to prepare a liquid crystal composition in which the temperature range of coexisting the nematic phase and the isotropic phase is wide in a wide temperature range, and the chiral agent is added thereto, and thus the composition that develops the optically isotropic liquid crystal phase in the wide temperature range can be prepared.

As the liquid crystal composition having the wide temperature range in which the nematic phase or the chiral nematic phase and the isotropic phase coexist, a liquid crystal composition having a difference between the maximum temperature and the minimum temperature in which the chiral nematic phase and the non-liquid crystal isotropic phase coexist is 3 to 150° C. is preferred, and a liquid crystal composition having a difference in the range of 5 to 150° C. is further preferred. A liquid crystal compound having a difference between the maximum temperature and the minimum temperature in which the nematic phase and the non-liquid crystal isotropic phase coexist is 3 to 150° C. is also preferred.

If an electric field is applied to the liquid crystal medium according to the invention in the optically isotropic liquid crystal phase, electric birefringence is caused, but the birefringence does not necessarily result from the Kerr effect.

The electric birefringence in the optically isotropic liquid crystal phase becomes larger as the pitch becomes longer. Therefore, the electric birefringence can be increased by adjusting a kind and a content of the chiral agent to set a long pitch, as long as a demand for other optical characteristics (transmittance, a diffraction wavelength or the like) is satisfied.

Any Other Component

The liquid crystal composition according to the invention may further contain a solvent, a monomer, a macromolecular substance, a polymerization initiator, an antioxidant, an ultraviolet light absorbent, a curing agent, a stabilizer, a dichroic dye, a photochromic compound or the like within the range in which the characteristics of the composition are not significantly influenced.

Specific examples of the dichroic dye to be used in the liquid crystal composition according to the invention include a merocyanine type, a styryl type, an azo type, an azomethine type, an azoxy type, a quinophthalone type, an anthraquinone type and a tetrazine type.

Optically Isotropic Polymer/Liquid Crystal Composite Material

1 Polymer/Liquid Crystal Composite Material

The polymer/liquid crystal composite material according to the invention is a composite material containing the liquid crystal composition and the polymer to exhibit optical isotropy, and can be used in the optical device driven in the optically isotropic liquid crystal phase. The liquid crystal composition contained in the polymer/liquid crystal composite material according to the invention is the liquid crystal composition according to the invention.

"Polymer/liquid crystal composite material" according to the invention is not particularly limited, as long as the composite material contains both the liquid crystal material and the polymer compound, but may be in a state in which the polymer and the liquid crystal material cause phase separation in a state in which the polymer is not partially or wholly dissolved into the liquid crystal material.

The optically isotropic polymer/liquid crystal composite material according to a preferred aspect of the invention can develop the optically isotropic liquid crystal phase in a wide temperature range. Moreover, the polymer/liquid crystal composite material according to a preferred aspect of the invention has a significantly high response speed. Moreover, the polymer/liquid crystal composite material according to a preferred aspect of the invention can be preferably used for the optical device such as the display device, based on the effects.

2 Polymer Compound

The composite material according to the invention can be manufactured by mixing the optically isotropic liquid crystal composition and the polymer obtained by allowing polymerization in advance, but is preferably manufactured by mixing a low molecular weight monomer, macro monomer, oligomer or the like (hereinafter, collectively referred to as "monomer or the like") to be the polymer material, and the liquid crystal composition CLC, and then performing a polymerization reaction in the mixture. The mixture containing the monomer or the like and the liquid crystal composition is referred to as "polymerizable monomer/liquid crystal mixture" herein. "Polymerizable monomer/liquid crystal mixture" may contain, when necessary, a polymerization initiator, a curing agent, a catalyst, a stabilizer, a dichroic dye or a photochromic compound or the like as described later in the range in which advantageous effects of the invention are not adversely affected. For example, the polymerizable monomer/liquid crystal mixture according to the invention may contain, when necessary, 0.1 to 20 parts by weight of the polymerization initiator based on 100 parts by weight of the polymerizable monomer. "Polymerizable monomer/liquid crystal mixture" is essentially the liquid crystal medium when the mixture is polymerized in the blue phase, but when the mixture is polymerized in the isotropic phase, the mixture is not necessary the liquid crystal medium.

A polymerization temperature preferably includes temperature at which the polymer/liquid crystal composite material exhibits high transparency and isotropy. The polymerization temperature further preferably includes temperature at which the mixture of the monomer and the liquid crystal material develops the isotropic phase or the blue phase, and polymerization is terminated in the isotropic phase or the optically isotropic liquid crystal phase. More specifically, the polymerization temperature preferably includes temperature at which, after polymerization, the polymer/liquid crystal composite material does not substantially scatter light on a side of a wavelength longer than a wavelength of visible light, and develops an optically isotropic state.

As a raw material of the polymer that constitutes the composite material according to the invention, a low molecular weight monomer, macro monomer or oligomer can be used, for example. The raw material monomer of the polymer herein is used in the meaning including the low molecular weight monomer, macro monomer or oligomer. Moreover, the polymer obtained preferably has a three-dimensional crosslinking structure, and therefore a polyfunctional monomer having two or more polymerizable functional groups is preferably used as the raw material monomer of the polymer. The polymerizable functional group is not particularly limited. Specific examples include an acrylic group, a methacrylic group, a glycidyl group, an epoxy group, an oxetanyl group and a vinyl group, but preferably an acrylic group and a methacrylic group from a viewpoint of a rate of polymerization. Among the raw material monomers of the polymer, incorporation of a monomer having two or more polymerizable functional groups in the range of 10% by weight or more into the monomer is preferred because transparency and isotropy with a high level are easily developed in the composite material according to the invention.

In order to obtain a preferred composite material, the polymer has preferably a mesogen moiety, and a raw material monomer having the mesogen moiety can be partially or wholly used as the raw material monomer of the polymer.

2-1 Monofunctional or Bifunctional Monomer Having Mesogen Moiety

A monofunctional or bifunctional monomer having the mesogen moiety is not particularly limited structurally, but specific examples include a compound represented by formula (M1) or formula (M2) below.

(M1)

(M2)

In formula (M1), $R^a$ is hydrogen, halogen, —C≡N, —N=C=O, —N=C=S or alkyl having 1 to 20 carbons, and at least one of —CH$_2$— in the alkyl may be replaced by —O—, —S—, —CO—, —COO— or —OCO—, at least one of —CH$_2$—CH$_2$— in the alkyl may be replaced by —CH=CH—, —CF=CF— or —C≡C—, and at least one of hydrogen in the alkyl, in a group in which at least one of —CH$_2$— in the alkyl is replaced by —O—, —S—, —COO— or —OCO—, or in a group in which at least one of —CH$_2$—CH$_2$— in the alkyl is replaced by —CH=CH— or —C≡C— may be replaced by halogen or —C≡N. $R^b$ is each independently a polymerizable group represented by formula (M3-1) to formula (M3-7).

(M3-1)

(M3-2)

(M3-3)

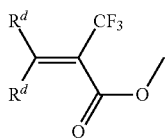

(M3-4)

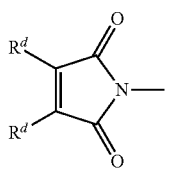

(M3-5)

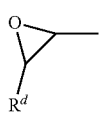

(M3-6)

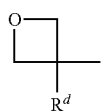

(M3-7)

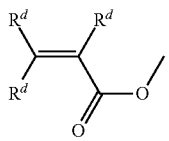

Preferred $R^a$ is hydrogen, halogen, —C≡N, —CF$_3$, —CF$_2$H, —CFH$_2$, —OCF$_3$, —OCF$_2$H, alkyl having 1 to 20 carbons, alkoxy having 1 to 19 carbons, alkenyl having 2 to 21 carbons, and alkynyl having 2 to 21 carbons. Particularly preferred $R^a$ is —C≡N, alkyl having 1 to 20 carbons and alkoxy having 1 to 19 carbons.

In formula (M2), $R^b$ is each independently a polymerizable group represented by formula (M3-1) to formula (M3-7).

Here, $R^d$ in formulas (M3-1) to (M3-7) is each independently hydrogen, halogen or alkyl having 1 to 5 carbons, and at least one of hydrogen in the alkyl may be replaced by halogen. Preferred $R^d$ is hydrogen, halogen and methyl. Particularly preferred $R^d$ is hydrogen, fluorine and methyl.

Moreover, a monomer represented by formula (M3-2), formula (M3-3), formula (M3-4) or formula (M3-7) is preferably polymerized according to radical polymerization. A monomer represented by formula (M3-1), formula (M3-5) or formula (M3-6) is preferably polymerized according to cationic polymerization. All progress in the form of living polymerization, and therefore if a small amount of radicals or cation active species is generated in a reaction system, polymerization starts. A polymerization initiator can be used for the purpose of accelerating generation of the active species. For example, light or heat can be used for generation of the active species.

In formulas (M1) and (M2), $A^M$ is each independently an aromatic or non-aromatic five-membered ring or six-membered ring, or a condensed ring having 9 or more carbons, and —CH$_2$— in the rings may be replaced by —O—, —S—, —NH— or —NCH$_3$—, —CH= in the rings may be replaced by —N=, and a hydrogen atom on the rings may be replaced by halogen, and alkyl or alkyl halide each having 1 to 5 carbons. Specific examples of preferred $A^M$ include 1,4-cyclohexylene, 1,4-cyclohexenylene, 1,4-phenylene, naphthalene-2,6-diyl, tetrahydronaphthalene-2,6-diyl, fluorene-2,7-diyl or bicyclo[2.2.2]octane-1,4-diyl, at least one of —CH$_2$— in the rings may be replaced by —O—, at least one of —CH= may be replaced by —N=, and at least one of hydrogen in the rings may be replaced by halogen, alkyl having 1 to 5 carbons or alkyl halide having 1 to 5 carbons.

In consideration of stability of the compound, —CH$_2$—O—CH$_2$—O— in which oxygen and oxygen are not adjacent is preferred to —CH$_2$—O—O—CH$_2$— in which oxygen and oxygen are adjacent. A same rule is applied also to sulfur.

Among the groups, particularly preferred $A^M$ is 1,4-cyclohexylene, 1,4-cyclohexenylene, 1,4-phenylene, 2-fluoro-1,4-phenylene, 2,3-difluoro-1,4-phenylene, 2,5-difluoro-1,4-phenylene, 2,6-difluoro-1,4-phenylene, 2-methyl-1,4-phenylene, 2-trifluoromethyl-1,4-phenylene, 2,3-bis(trifluoromethyl)-1,4-phenylene, naphthalene-2,6-diyl, tetrahydronaphthalene-2,6-diyl, fluorene-2,7-diyl, 9-methylfluorene-2,7-diyl, 1,3-dioxane-2,5-diyl, pyridine-2,5-diyl and pyrimidine-2,5-diyl. In addition, with regard to a configuration of 1,4-cyclohexylene and 1,3-dioxane-2,5-diyl described above, trans is preferred to cis.

Then, 2-fluoro-1,4-phenylene is structurally identical with 3-fluoro-1,4-phenylene, and specific examples are not shown for the latter. A same rule is also applied to a relationship between 2,5-difluoro-1,4-phenylene and 3,6-difluoro-1,4-phenylene, or the like.

In formulas (M1) and (M2), Y is each independently a single bond or alkylene having 1 to 20 carbons. In the alkylene, at least one of —CH$_2$— may be replaced by —O— or —S—, and at least one of —CH$_2$—CH$_2$— in the alkylene may be replaced by —CH=CH—, —COO— or —OCO—. Preferred Y is a single bond, —(CH$_2$)$_{m2}$—, —O(CH$_2$)$_{m2}$— and —(CH$_2$)$_{m2}$O—(in the formulas, m2 is an integer from 1 to 20.). Particularly preferred Y is a single bond, —(CH$_2$)$_{m2}$—, —O(CH$_2$)$_{m2}$— and —(CH$_2$)$_{m2}$O— (in the formulas, m2 is an integer from 1 to 10). In consideration of stability of the compound, —Y—$R^a$ and —Y—$R^b$ preferably have neither —O—O—, nor —O—S—, nor —S—O— nor —S—S— in the groups.

In formulas (M1) and (M2), $Z^M$ is each independently a single bond, —(CH$_2$)$_{m3}$—, —O(CH$_2$)$_{m3}$—, —(CH$_2$)$_{m3}$O—, —O(CH$_2$)$_{m3}$O—, —CH=CH—, —C≡C—, —COO—, —OCO—, —(CF$_2$)$_2$—, —(CH$_2$)$_2$—COO—, —OCO—(CH$_2$)$_2$—, —CH=CH—COO—, —OCO—CH=CH—, —C≡C—COO—, —OCO—C≡C—, —CH=CH—(CH$_2$)$_2$—, —(CH$_2$)$_2$—CH=CH—, —CF=CF—, —C≡C—CH=CH—, —CH=CH—C≡C—, —OCF$_2$—(CH$_2$)$_2$—, —(CH$_2$)$_2$—CF$_2$O—, —OCF$_2$— or —CF$_2$O— (in the formulas, m3 is an integer from 1 to 20).

Preferred $Z^M$ is a single bond, —(CH$_2$)$_{m3}$—, —O(CH$_2$)$_{m3}$—, —(CH$_2$)$_{m3}$O—, —CH=CH—, —C≡C—, —COO—, —OCO—, —(CH$_2$)$_2$—COO—, —OCO—(CH$_2$)$_2$—, —CH=CH—COO—, —OCO—CH=CH—, —OCF$_2$— and —CF$_2$O—.

In formulas (M1) and (M2), m1 is an integer from 1 to 6. Preferred m1 is an integer from 1 to 3. When m1 is 1, the monomer is a bicyclic compound having two rings such as a six-membered ring. When m1 is 2 and 3, the monomers are a tricyclic compound and a tetracyclic compound, respectively. For example, two of $A^M$ when m1 is 1 may be identical or different. For example, three of $A^M$ (or two of $Z^M$) when m1 is 2 may also be identical or different. When m1 is 3 to 6, a same rule is applied thereto. A same rule is also applied to $R^a$, $R^b$, $R^d$, $Z^M$, $A^M$ and Y.

Even if compound (M1) represented by formula (M1) and compound (M2) represented by formula (M2) contain an isotope such as $^2$H (deuterium) and $^{13}$C in an amount higher than an amount of natural abundance, compound (M1) and compound (M2) have similar characteristics, and therefore such compound (M1) and compound (M2) can be preferably used.

Further preferred examples of compound (M1) and compound (M2) include compounds (M1-1) to (M1-41) and compounds (M2-1) to (M2-27) as represented by formulas (M1-1) to (M1-41) and (M2-1) to (M2-27), respectively. In the compounds, $R^a$, $R^b$, $R^d$, $Z^M$, $A^M$, Y and p are defined in a manner identical with the definitions in formulas (M1) and (M2) as described in the aspect of the invention.

A partial structure as described below in compounds (M1-1) to (M1-41) and (M2-1) to (M2-27) will be described. Partial structure (a1) represents 1,4-phenylene in which at least one of hydrogen is replaced by fluorine. Partial structure (a2) represents 1,4-phenylene in which at least one of hydrogen may be replaced by fluorine. Partial structure (a3) represents 1,4-phenylene in which at least one of hydrogen may be replaced by either fluorine or methyl. Partial structure (a4) represents fluorene in which hydrogen in 9-position may be replaced by methyl.

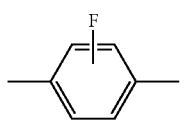
(a1)

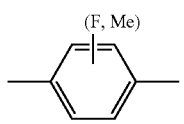
(a3)

(a2)

(a4)

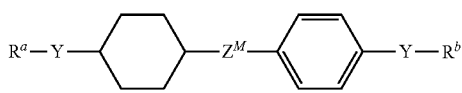
(M1-1)

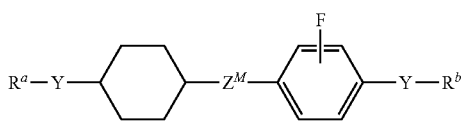
(M1-2)

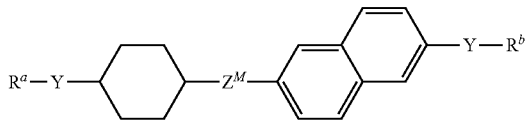
(M1-3)

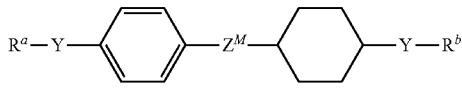
(M1-4)

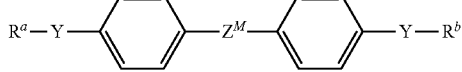
(M1-5)

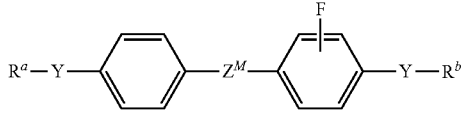
(M1-6)

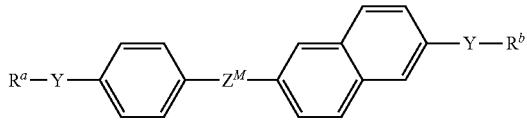
(M1-7)

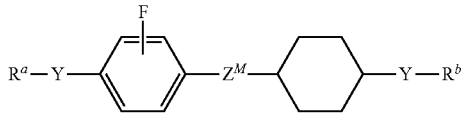
(M1-8)

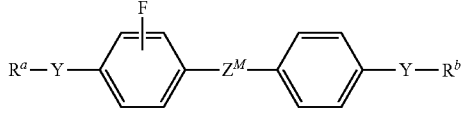
(M1-9)

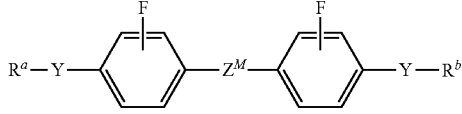
(M1-10)

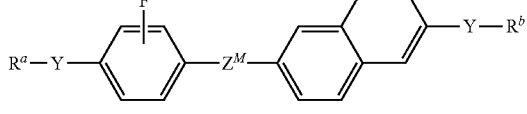
(M1-11)

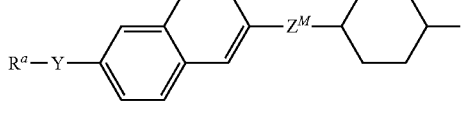
(M1-12)

-continued
(M1-13)
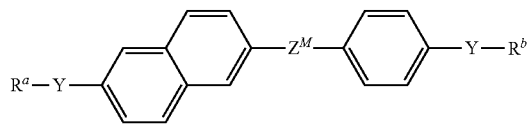
(M1-14)
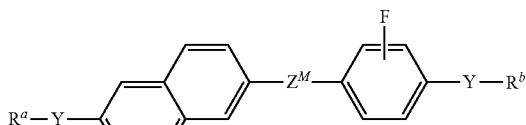
(M1-15)
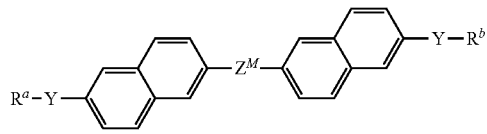
(M1-16)
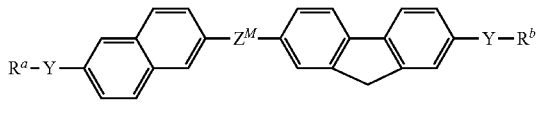
(M1-17)
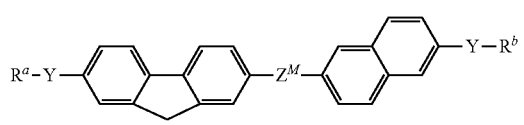
(M1-18)
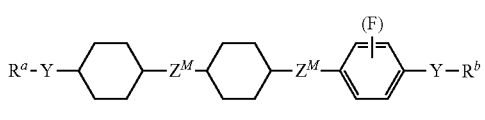
(M1-19)
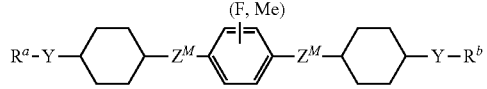
(M1-20)
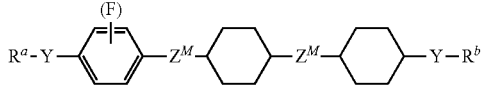
(M1-21)
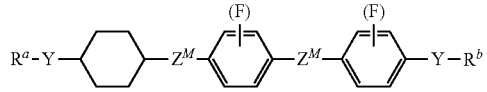
(M1-22)
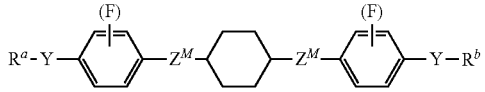
(M1-23)
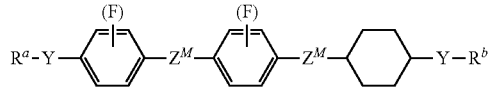
(M1-24)
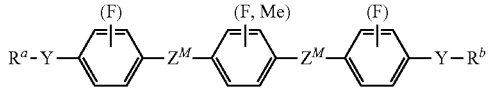
(M1-25)
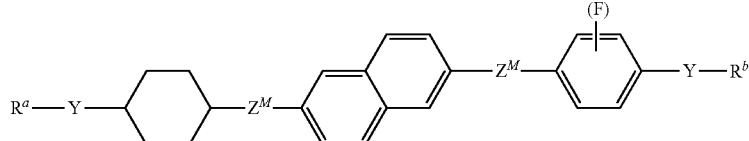
(M1-26)
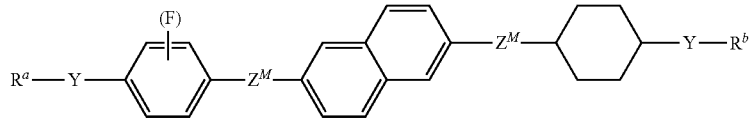
(M1-27)
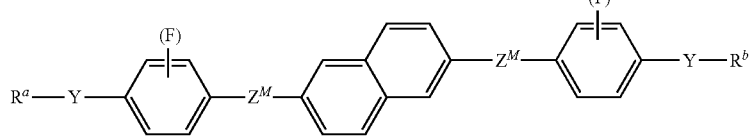
(M1-28)
(M1-29)
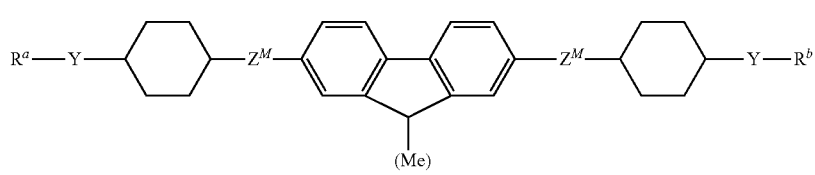

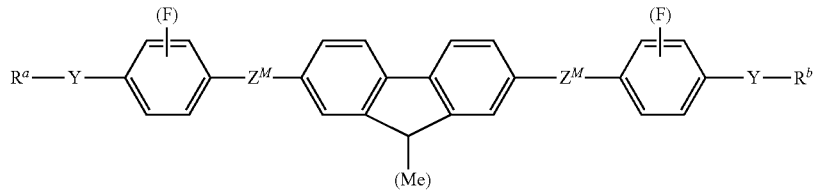
(M1-30)
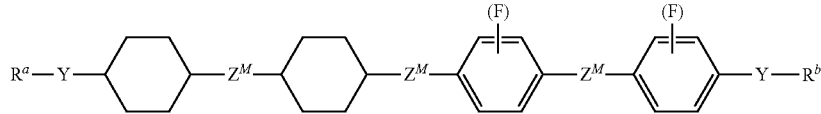
(M1-31)
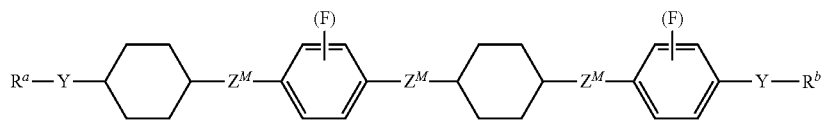
(M1-32)
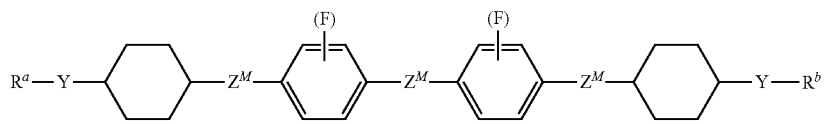
(M1-33)
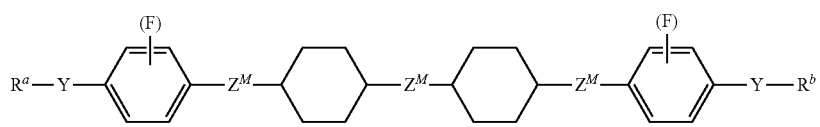
(M1-34)
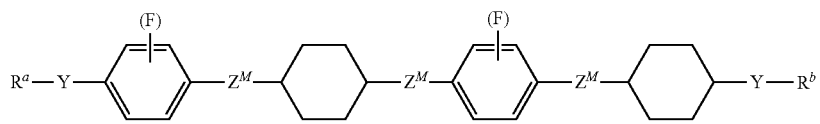
(M1-35)
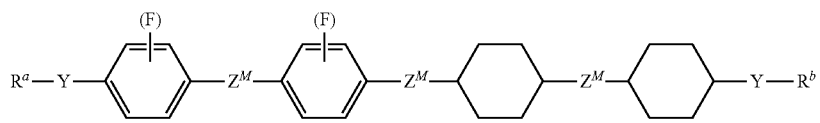
(M1-36)
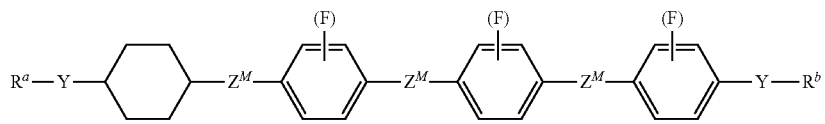
(M1-37)
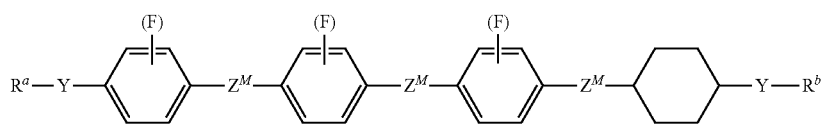
(M1-38)
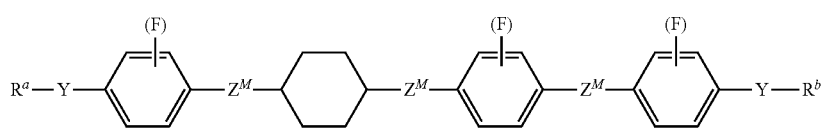
(M1-39)
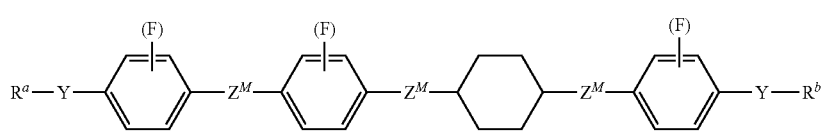
(M1-40)

-continued
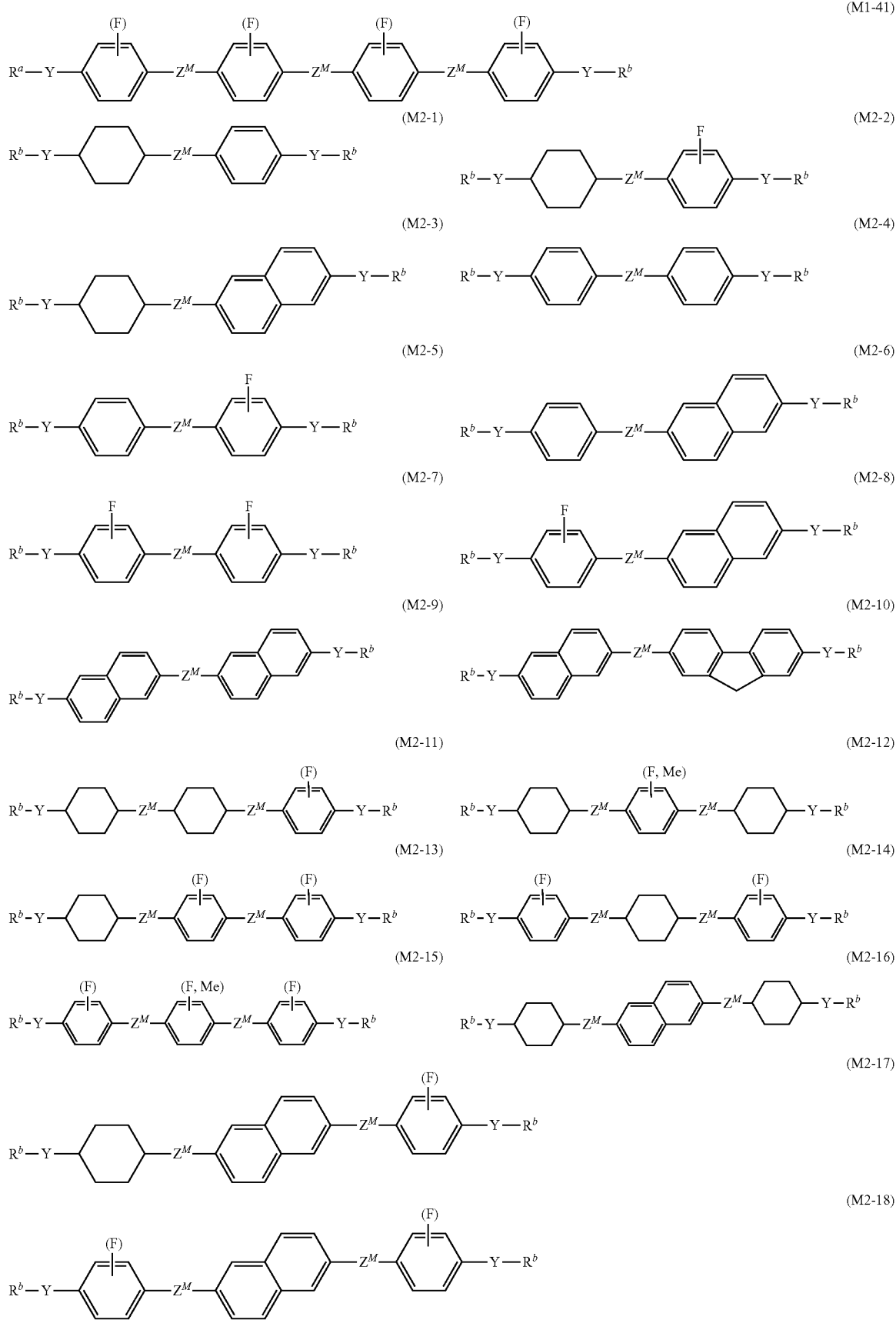

(M2-19)
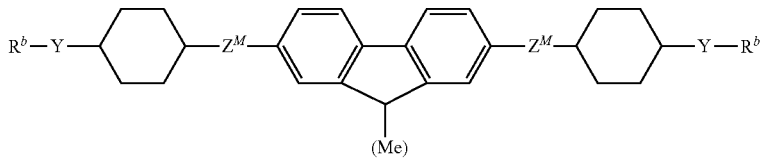

(M2-20)
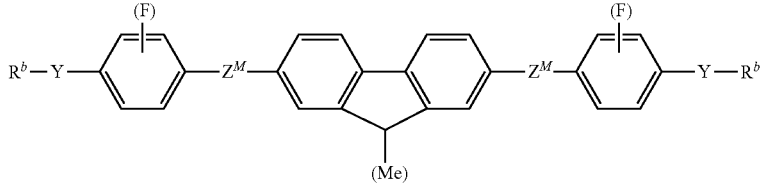

(M2-21)
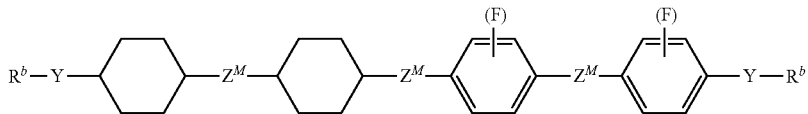

(M2-22)
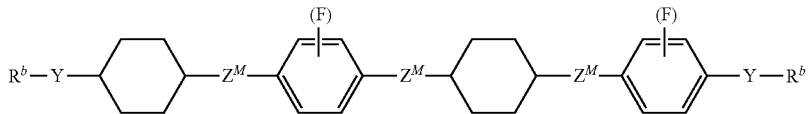

(M2-23)
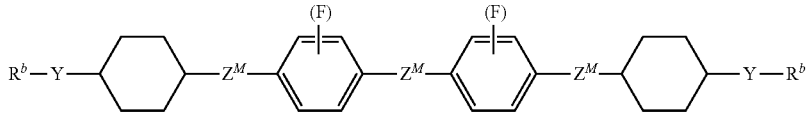

(M2-24)
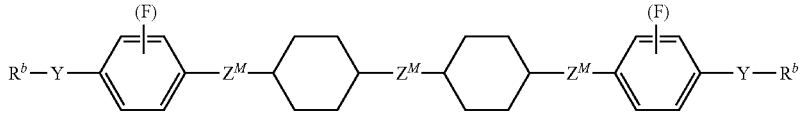

(M2-25)
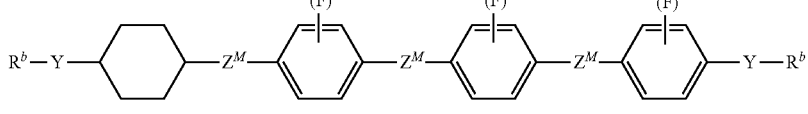

(M2-26)
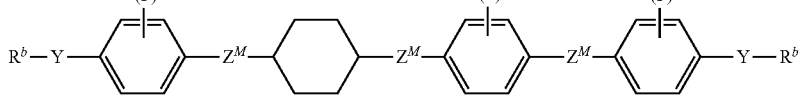

(M2-27)
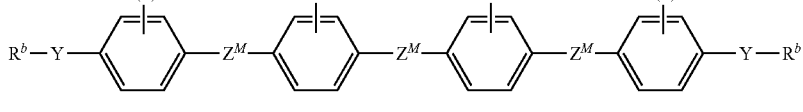

A polymerizable compound other than the monomer having no mesogen moiety, and monomer (M1) and (M2) both having the mesogen moiety as described above can be used when necessary.

For the purpose of optimizing the optical isotropy of the polymer/liquid crystal composite material according to the invention, a monomer having a mesogen moiety and three or more polymerizable functional groups can also be used. As the monomer having the mesogen moiety and three or more polymerizable functional groups, a publicly known compound can be preferably used. Specific examples of the compounds are represented by formulas (M4-1) to (M4-3), and further specific examples of the compounds are described in JP 2000-327632 A, JP 2004-182949 A and JP 2004-59772 A. However, in formulas (M4-1) to (M4-3), $R^b$, $Z^M$, Y and (F) are defined in a manner identical with the definitions as described above.

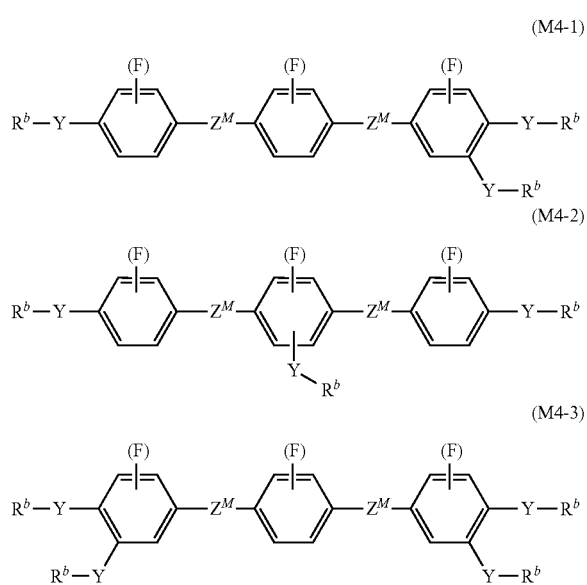

2-2 Monomer Having Polymerizable Functional Group and No Mesogen Moiety

Specific examples of monomers having a polymerizable functional group and no mesogen moiety include straight-chain or branched acrylate having 1 to 30 carbons, straight-chain or branched diacrylate having 1 to 30 carbons, or as a monomer having three or more functional groups, glycerol propoxylate (1PO/OH) triacrylate, pentaerythritol propoxylate triacrylate, pentaerythritol triacrylate, trimethylolpropane ethoxylated triacrylate, trimethylolpropane propoxylate triacrylate, trimethylolpropane triacrylate, di(trimethylolpropane)tetraacrylate, pentaerythritol tetraacrylate, di(pentaerythritol)pentaacrylate, di(pentaerythritol)hexaacrylate and trimethylolpropane triacrylate, but are not limited thereto.

2-3 Polymerization Initiator

The polymerization reaction in manufacturing the polymer that constitutes the composite material according to the invention is not particularly limited. For example, photoradical polymerization, thermal radical polymerization, photocationic polymerization or the like is performed.

Specific examples of a photoradical polymerization initiator that can be used in the photoradical polymerization include DAROCUR 1173 and 4265 (both being trade names, BASF Japan Ltd.) and IRGACURE 184, 369, 500, 651, 784, 819, 907, 1300, 1700, 1800, 1850 and 2959 (all being trade names, BASF Japan Ltd.).

Specific examples of a preferred initiator for thermal radical polymerization by heat, in which the initiator can be used in the thermal radical polymerization, include benzoyl peroxide, diisopropyl peroxydicarbonate, t-butyl peroxy-2-ethylhexanoate, t-butyl peroxypivalate, t-butyl peroxydiisobutyrate, lauroyl peroxide, dimethyl-2,2'-azobisisobutyrate (MAIB), di-t-butyl peroxide (DTBPO), azobisisobutyronitrile (AIBN) and azobiscyclohexanecarbonitrile (ACN).

Specific examples of a photocationic polymerization initiator that can be used in the photocationic polymerization include diaryliodonium salt (hereinafter, referred to as "DAS") and a triarylsulfonium salt (hereinafter, referred to as "TAS")

Specific examples of DAS include diphenyliodonium tetrafluoroborate, diphenyliodonium hexafluorophosphonate, diphenyliodonium hexafluoroarsenate, diphenyliodonium trifluoromethanesulfonate, diphenyliodonium trifluoroacetate, diphenyliodonium p-toluenesulfonate, diphenyliodonium tetra(pentafluorophenyl)borate, 4-methoxyphenyphenyliodonium tetrafluoroborate, 4-methoxyphenyphenyliodonium hexafluorophosphonate, 4-methoxyphenyphenyliodonium hexafluoroarsenate, 4-methoxyphenyphenyliodonium trifluoromethanesulfonate, 4-methoxyphenylphenyliodonium trifluoroacetate and 4-methoxyphenyphenyliodonium p-toluenesulfonate.

An improvement in sensitivity can be achieved by adding a photosensitizer such as thioxanthone, phenothiazine, chlorothioxanthone, xanthone, anthracene, diphenylanthracene and rubrene to DAS.

Specific examples of TAS include triphenylsulfonium tetrafluoroborate, triphenylsulfonium hexafluorophosphonate, triphenylsulfonium hexafluoroarsenate, triphenylsulfonium trifluoromethanesulfonate, triphenylsulfonium trifluoroacetate, triphenylsulfonium-p-toluenesulfonate, triphenylsulfonium tetra(pentafluorophenyl)borate, 4-methoxyphenydiphenylsulfonium tetrafluoroborate, 4-methoxyphenydiphenylsulfonium hexafluorophosphonate, 4-methoxyphenydiphenylsulfonium hexafluoroarsenate, 4-methoxyphenyldiphenylsulfonium trifluoromethanesulfonate, 4-methoxyphenyldiphenylsulfonium trifluoroacetate and 4-methoxyphenydiphenylsulfonium-p-toluenesulfonate.

Specific examples of trade names of the photocationic polymerization initiator include Cyracure UVI-6990, Cyracure UVI-6974 and Cyracure UVI-6992 (each being a trade name, UCC), Adekaoptomer SP-150, SP-152, SP-170 and SP-172 (each being a trade name, ADEKA Corporation) and Rhodorsil Photoinitiator 2074 (trade name, Rhodia Japan, Ltd.), IRGACURE 250 (a trade name, BASF Japan Ltd.) and UV-9380C (a trade name, GE Toshiba Silicones Co., Ltd.).

2-4 Curing Agent or the Like

In manufacturing the polymer that constitutes the composite material according to the invention, in addition to the monomer or the like and the polymerization initiator, one kind or two or more kinds of other preferred components, for example, the curing agent, the catalyst and the stabilizer, may be added.

As the curing agent, a publicly known latent curing agent that has been used as a curing agent for an epoxy resin so far can be ordinarily used. Specific examples of the latent curing agent for the epoxy resin include an amine curing agent, a novolak resin curing agent, an imidazole curing agent and an acid anhydride curing agent. Specific examples of the amine curing agent include aliphatic polyamine such as diethylenetriamine, triethylenetetramine, tetraethylenepentamine, m-xylenediamine, trimethylhexamethylenediamine, 2-methylpentamethylenediamine and diethylaminopropylamine, alicyclic polyamine such as isophoronediamine, 1,3-bisaminomethylcyclohexane, bis(4-aminocyclohexyl)methane, norbornenediamine, 1,2-diaminocyclohexane and laromine, and aromatic polyamine such as diaminodiphenylmethane, diaminodiphenylethane and metaphenylenediamine.

Specific examples of the novolak resin curing agent include a phenol novolak resin and a bisphenol novolak resin. Specific examples of the imidazole curing agent include 2-methylimidazole, 2-ethylhexylimidazole, 2-phenylimidazole and 1-cyanoethyl-2-phenylimidazolium-trimellitate.

Specific examples of the acid anhydride curing agent include tetrahydrophthalic anhydride, hexahydrophthalic anhydride, methyltetrahydrophthalic anhydride, methylhexahydrophthalic anhydride, methylcyclohexenetetracarboxylic dianhydride, phthalic anhydride, trimellitic anhydride, pyromellitic anhydride and benzophenonetetracarboxylic dianhydride.

Moreover, a curing accelerator for accelerating a curing reaction between a polymerizable compound having a glycidyl group, an epoxy group and an oxetanyl group and the curing agent may be further used. Specific examples of the curing accelerator include tertiary amines such as benzyldimethyl amine, tris(dimethylaminomethyl)phenol and dimethylcyclohexylamine, imidazoles such as 1-cyanoethyl-2-ethyl-4-methylimidazole and 2-ethyl-4-methylimidazole, an organic phosphorus compound such as triphenyl phosphine, quaternary phosphonium salts such as tetraphenylphosphonium bromide, diazabicycloalkenes such as 1,8-diazabicyclo[5.4.0]undecene-7 and an organic acid salt thereof, quaternary ammonium salts such as tetraethylammonium bromide and tetrabutylammonium bromide, and a boron compound such as boron trifluoride and triphenyl borate. The curing accelerators can be used alone or by mixing a plurality of kinds.

In order to prevent unwanted polymerization during storage, for example, the stabilizer is preferably added. As the stabilizer, all the compounds known by those skilled in the art can be used. Typified examples of the stabilizer include 4-ethoxyphenol, hydroquinone and butylated hydroxytoluene (BHT).

3 Composition of Polymer/Liquid Crystal Composite Material

A content of the liquid crystal composition in the polymer/liquid crystal composite material according to the invention is preferably as high as possible, as long as the composite material can develop the optically isotropic liquid crystal phase. The reason is that a value of electric birefringence of the composite material according to the invention becomes larger as the content of the liquid crystal composition is higher.

In the polymer/liquid crystal composite material according to the invention, the content of the liquid crystal composition is preferably 60 to 99% by weight, further preferably 60 to 98% by weight, and particularly preferably 80 to 97% by weight, based on the composite material. Moreover, in the polymer/liquid crystal composite material according to the invention, a content of the polymer is preferably 1 to 40% by weight, further preferably 2 to 40% by weight, and particularly preferably 3 to 20% by weight, based on the composite material.

4 Optical Device

The optical device according to the invention refers to the optical device including the liquid crystal composition or the polymer/liquid crystal composite material (hereinafter, the liquid crystal composition and the polymer/liquid crystal composite material according to the invention may be occasionally referred to generically as the liquid crystal medium) and to be driven in the optically isotropic liquid crystal phase.

The liquid crystal medium is optically isotropic during no application of the electric field, but when the electric field is applied, the optical anisotropy is caused in the liquid crystal medium to allow optical modulation by the electric field.

Specific examples of structure of the liquid crystal display device include, as shown in FIG. 1, the structure in which electrode 1 extended from a left side and electrode 2 extended from a right side are alternately arranged in electrodes of a comb-shaped electrode substrate. When a potential difference exists between electrode 1 and electrode 2, on the comb-shaped electrode substrate as shown in FIG. 1, if attention is paid to one electrode, a state in which electric fields in two directions, namely an upward direction and a downward direction on the diagram, can be provided.

The liquid crystal composition according to the invention can be used in the optical device. The liquid crystal composition according to the invention exhibits the low driving voltage and the short response time, and therefore the optical device in a preferred aspect of the invention can achieve low-voltage driving and a fast response.

EXAMPLES

The invention is described in greater detail by way of Examples, but the invention is not limited by the Examples. In addition, unless otherwise noted, "%" means "% by weight." Moreover, a compound obtained was identified by a nuclear magnetic resonance spectrum to be obtained by 1H-NMR analysis, a gas chromatogram obtained by gas chromatography (GC) analysis or the like. An analytical method was as described below.

1-1 $^1$H-NMR Analysis

As a measuring apparatus, DRX-500 (trade name, Bruker BioSpin Corporation) was used. A sample prepared in Examples and so forth was dissolved into a deuterated solvent such as $CDCl_3$ in which the sample was soluble, and measurement was carried out under the conditions of room temperature, 500 MHz and 24 times of accumulation. In the explanation of the nuclear magnetic resonance spectrum obtained, s, d, t, q and m stand for a singlet, a doublet, a triplet, a quartet and a multiplet, respectively. Tetramethylsilane (TMS) was used for a reference material for a zero point of chemical shifts: δ values.

1-2 GC Analysis

As a measuring apparatus, GC-14B Gas Chromatograph made by Shimadzu Corporation was used. As a column, a capillary column CBP1-M25-025 (length 25 m, bore 0.22 mm, film thickness 0.25 (μm); dimethylpolysiloxane as a stationary liquid phase; non-polar) made by Shimadzu Corporation was used. Helium was used as a carrier gas, and a flow rate was adjusted at 1 mL/min. Temperature in a sample injector was set at 300° C. and temperature of a detector (FID) part was set at 300° C.

A sample was dissolved into toluene to prepare a 1% solution, and then 1 microliter of the solution obtained was injected into the sample injector.

As a recorder, C-R6A Chromatopac made by Shimadzu Corporation or an equivalent thereof was used. The resulting gas chromatogram showed a retention time of a peak and a value of a peak area corresponding to each of component compounds.

As a solvent for diluting the sample, chloroform or hexane, for example, may also be used. Moreover, as the column, capillary column DB-1 (length 30 m, bore 0.32 mm, film thickness 0.25 μm) made by Agilent Technologies Inc., HP-1 (length 30 m, bore 0.32 mm, film thickness 0.25 μm) made by Agilent Technologies Inc., Rtx-1 (length 30 m, bore 0.32 mm, film thickness 0.25 μm) made by Restek Corporation, BP-1 (length 30 m, bore 0.32 mm, film thickness 0.25 μm) made by SGE International Pty. Ltd. and so forth may be used.

A ratio of the peak areas in the gas chromatogram corresponds to a ratio of the component compounds. In general, weight percent of each of the component compounds in an analytical sample is not completely identical with a percentage of each of the peak areas in the analytical sample. However, when the column described above was used in the invention, the weight percent of each of the component compounds in the analytical sample substantially corresponds to the percentage of each of the peak areas in the analytical sample because a correction coefficient is essentially 1 (one). The reason is that no significant difference exists among the correction coefficients of the component compounds. In order to more accurately determine a composition ratio of the liquid crystal compounds in the liquid crystal composition by the chromatogram, an internal standard method by the chromatogram is applied. Each component (test-component) of the liquid crystal compounds and a liquid crystal compound as a standard (standard reference material) as weighed accurately in a fixed amount are simultaneously measured by means of gas chromatography, and relative intensity is calculated in advance relative to a ratio of a peak area of the test-component to a peak area of the standard reference material. When correction is performed using the relative intensity of the peak area of each component to the peak area of the standard reference material, the composition ratio of the liquid crystal compounds in the liquid crystal composition can be more accurately determined from the gas chromatographic analysis.

1-3 Sample for Determining Values of Physical Properties of Liquid Crystal Compound or the Like A sample for determining values of physical properties of the liquid crystal compound is used in two types of cases: a case where a compound per se is used as the sample, and a case where the compound is mixed with a base liquid crystal to be used as the sample.

In the latter case where the sample prepared by mixing the compound with the base liquid crystal is used, measurement is carried out according to the method described below. First, a sample is prepared by mixing 15% of the liquid crystal compound obtained and 85% of the base liquid crystal. Then, according to an extrapolation method based on a calculation formula as described below, extrapolated values are calculated from measured values of the sample obtained. The extrapolated values are described as the values of physical properties of the compound.

(Extrapolated value)={100×(measured value of a sample)−(% of base liquid crystal)×(measured value of the base liquid crystal)}/(% of the compound).

When a smectic phase or crystals precipitated at 25° C. even at the above ratio of the compound to base liquid crystal A (15%:85%), a ratio of the compound to the base liquid crystal was changed in the order of (10%:90%), (5%:95%) and (1%:99%). Then, the physical properties of the sample were measured in a composition at which neither the smectic phase nor the crystals precipitated at 25° C. The extrapolated values were determined according to the above formula, and described as the values of physical properties of the compound.

As the base liquid crystal used for measurement, various kinds exist. For example, a composition (%) of base liquid crystal A is as described below.

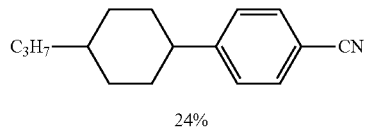

24%

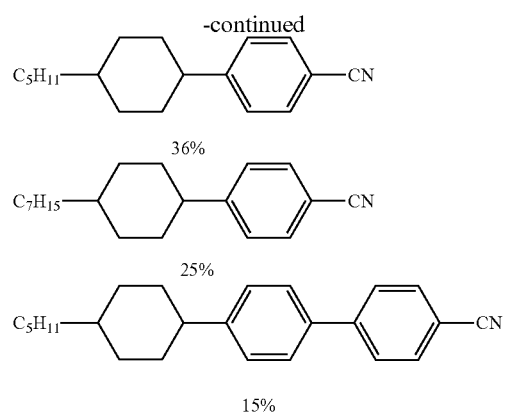

1-4 Method for Determining Values of Physical Properties of Liquid Crystal Compound or the Like Values of physical properties were determined according to the methods described below. Most of the measuring methods are described in EIAJ ED-2521A of the Standard of Electronic Industries Association of Japan, or modified thereon. Moreover, no TFT was attached to a TN device used for measurement.

Among measured values, in the case where the liquid crystal compound per se was used as the sample, values obtained were described as experimental data. In the case where a mixture of the liquid crystal compound with the base liquid crystal was used as the sample, values obtained according to the extrapolation method were described as experimental data.

Phase structure and phase transition temperature (° C.): Measurement was carried out according to method (1) and method (2) as described below.

(1) A compound was placed on a hot plate of a melting point apparatus (FP52 Hot Stage made by Mettler-Toledo International Inc.) equipped with a polarizing microscope, and a state of phase and a change thereof were observed with the polarizing microscope while the compound was heated at a rate of 3° C. per minute, and a kind of the liquid crystal phase was specified.

(2) A sample was heated and then cooled at a rate of 3° C. per minute using a differential scanning calorimeter, DSC-7 System or Diamond DSC System, made by PerkinElmer, Inc. A starting point (on set) of an endothermic peak or an exothermic peak caused by a phase change of the sample was determined by extrapolation, and thus a phase transition temperature was determined.

Hereinafter, the crystals were expressed as K, and when the crystals were further distinguishable, each of the crystals was expressed as $K_1$ or $K_2$. The smectic phase was expressed as Sm, a nematic phase as N, and a chiral nematic phase as N*. A liquid (isotropic) was expressed as I. When smectic B phase or smectic A phase was distinguishable among the smectic phases, the phases were expressed as SmB or SmA, respectively. BP stands for a blue phase or an optically isotropic liquid crystal phase. A coexistence state of the two phases may be occasionally expressed in the form of (N*+I) or (N*+BP). Specifically, (N*+I) stands for a phase in which a non-liquid crystal isotropic phase and the chiral nematic phase coexist, and (N*+BP) stands for a phase in which the BP phase or the optically isotropic liquid crystal phase and the chiral nematic phase coexist. Un stands for an unidentified phase that is not optically anisotropic. As an expression of the phase transition temperature, for example, "K 50.0 N 100.0 I" indicates that a phase transition temperature (KN) from the crystals to the nematic phase is 50.0° C., and a phase transition temperature (NI) from the nematic phase to the liquid is 100.0° C. A same rule applied to other expressions.

1-5 Maximum Temperature of Nematic Phase ($T_{NI}$; ° C.)

A sample (a mixture of a liquid crystal compound and a base liquid crystal) was placed on a hot plate of a melting point apparatus (FP52 Hot Stage made by Mettler-Toledo International Inc.) equipped with a polarizing microscope, and was observed with the polarizing microscope while heating the sample at a rate of 1° C. per minute. Temperature when part of the sample changed from the nematic phase to the isotropic liquid was described as a maximum temperature of the nematic phase. Hereinafter, a maximum temperature of the nematic phase may be occasionally abbreviated simply as "maximum temperature."

1-6 Compatibility at Low Temperature

Samples prepared by mixing a liquid crystal compound with a base liquid crystal for the liquid crystal compound to be 20%, 15%, 10%, 5%, 3% and 1% were put in glass vials. After the glass vials were kept in freezers at −10° C. or −20° C. for a predetermined period of time, whether or not the crystals or the smectic phase precipitated was observed.

1-7 Viscosity (Bulk Viscosity; η; Measured at 20° C.; mPa·s)

A mixture of a liquid crystal compound and a base liquid crystal was measured using a cone-plate type (E type) viscometer.

1-8 Refractive Index Anisotropy (Δn)

Measurement was carried out by an Abbe refractometer with a polarizing plate mounted on an ocular by using light at a wavelength of 589 nm at a temperature of 25° C. A surface of a main prism was rubbed in one direction, and then a sample (a mixture of a liquid crystal compound and base liquid crystal) was added dropwise onto the main prism. A refractive index (n||) was measured when the direction of polarized light was parallel to the direction of rubbing. A refractive index (n⊥) was measured when the direction of polarized light was perpendicular to the direction of rubbing. A value of refractive index anisotropy (Δn) was calculated from an equation: Δn=n||−n⊥.

1-9 Dielectric Anisotropy (Δ∈; Measured at 25° C.)

A sample (a mixture of a liquid crystal compound and a base liquid crystal) was put in a liquid crystal cell in which a distance (gap) between two glass substrates was about 9 micrometers and a twist angle was 80 degrees. A voltage of 20 V was applied to the cell, and a dielectric constant (∈||) in the major axis direction of liquid crystal molecules was measured. A voltage of 0.5 V was applied to the cell, and a dielectric constant (∈⊥) in the minor axis direction of the liquid crystal molecules was measured. Values of dielectric anisotropy were calculated from an equation: Δ∈=∈||−∈⊥.

1-10 Pitch (P; Measured at 25° C.; nm)

A pitch length was measured using selective reflection (Handbook of Liquid Crystals (Ekisho Binran in Japanese), page 196, issued in 2000, Maruzen Co., Ltd.). A relational expression: <n>p/λ=1 holds for selective reflection wavelength λ, in which <n> represents an average refractive index and is provided by the following expression: $<n>=\{(n_\|^2+n_\perp^2)/2\}^{1/2}$. The selective reflection wavelength was measured by a microspectrophotometer (trade name: MSV-350, JEOL Co., Ltd.). The pitch was determined by dividing the resulting reflection wavelength by the average refractive index. A pitch of a cholesteric liquid crystal having a reflection wavelength in a region of a wavelength longer than a wavelength of visible light is proportional to the reciprocal number of a concentration of an optically active compound in a region in which a concentration of the optically active compound is low. Thus, the pitch lengths of liquid crystals having a selective reflection wavelength in a visible light region were measured in several points, and the pitch was determined according to a linear extrapolation method. "Optically active compound" corresponds to a chiral agent in the invention.

Values of physical properties can be determined according to the methods described below. Most of the measuring methods are described in EIAJ ED-2521A of the Standard of Electronic Industries Association of Japan, or modified thereon. Moreover, no TFT was attached to a TN device used for measurement.

1-11 Maximum Temperature of Nematic Phase (NI; ° C.)

A sample was placed on a hot plate of a melting point apparatus equipped with a polarizing microscope, and heated at a rate of 1° C. per minute. Temperature when part of the sample changed from the nematic phase to the isotropic liquid was measured. A maximum temperature of the nematic phase may be occasionally abbreviated simply as "maximum temperature."

1-12 Minimum Temperature of Nematic Phase ($T_c$; ° C.)

Samples each having a nematic phase were kept in freezers at 0° C., −10° C., −20° C., −30° C. and −40° C. for 10 days, and then liquid crystal phases were observed. For example, when a sample maintained the nematic phase at −20° C. and changed to crystals (or a smectic phase) at −30° C., $T_c$ was expressed as $T_c \le -20°$ C. A minimum temperature of the nematic phase may be occasionally abbreviated as "minimum temperature."

1-13 Transition Temperature of Optically Isotropic Liquid Crystal Phase

A sample was placed on a hot plate of a melting point apparatus equipped with a polarizing microscope, and in a state of a crossed nicol, first, heated until the sample reached temperature at which the sample became a non-liquid crystal isotropic phase, and cooled at a rate of 1° C. per minute to completely develop the chiral nematic phase or the optically isotropic liquid crystal phase. Temperature at which phase transition was caused in a cooling process was measured, and then temperature was increased at a rate of 1° C. per minute, and temperature at which phase transition was caused in a heating process was measured. In the invention, unless otherwise noted, the temperature at which the phase transition was caused in the heating process was described as a phase transition temperature. When judgment of the phase transition temperature was difficult in a dark field under the crossed nicol in the optically isotropic liquid crystal phase, the phase transition temperature was measured by shifting a polarizer by 1 to 100 from the state of the crossed nicol.

1-14 Viscosity (Rotational Viscosity; γ1; Measured at 25° C.; mPa·s)

(1) Sample having positive dielectric anisotropy: Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. A voltage was stepwise applied to the device in the range of 16 V to 19.5 V at an increment of 0.5 V. After a period of 0.2 second with no voltage application, a voltage was applied repeatedly under the conditions of only one of rectangular waves (rectangular pulse; 0.2 second) and no voltage application (2 seconds). A peak current and a peak time of a transient current generated by the applied voltage were measured. A value of rotational viscosity was obtained from the measured values and a calculation equation (8) on page 40 of the paper presented by M. Imai et al. A value of dielectric anisotropy necessary for the calculation was determined according to a method as described below by using the device used for measuring the rotational viscosity.

(2) Sample having negative dielectric anisotropy: Measurement was carried out according to the method described in M. Imai et al., Molecular Crystals and Liquid Crystals, Vol. 259, p. 37 (1995). A sample was put in a VA device in which a distance (cell gap) between two glass substrates was 20 micrometers. A voltage was stepwise applied to the device in the range of 30 V to 50 V at an increment of 1 V. After a period of 0.2 second with no voltage application, a voltage was applied repeatedly under the conditions of only one of rectangular waves (rectangular pulse; 0.2 second) and no voltage application (2 seconds). A peak current and a peak time of a transient current generated by the applied voltage were measured. A value of rotational viscosity was obtained from the measured values and a calculation equation (8) on page 40 of the paper presented by M. Imai et al. As for dielectric anisotropy necessary for the calculation, a value of dielectric anisotropy measured as described below was used.

1-15 Refractive Index Anisotropy ($\Delta n$; Measured at 25° C.)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index ($n_\parallel$) was measured when the direction of polarized light was parallel to the direction of rubbing. A refractive index ($n_\perp$) was measured when the direction of polarized light was perpendicular to the direction of rubbing. A value of refractive index anisotropy was calculated from an equation: $\Delta n = n_\parallel - n_\perp$. When the sample was a composition, the refractive index anisotropy was measured according to the method.

1-16 Dielectric Anisotropy ($\Delta\epsilon$; Measured at 25° C.)

(1) Composition having positive dielectric anisotropy: A sample was put in a liquid crystal cell in which a distance (gap) between two glass substrates was about 9 micrometers and a twist angle was 80 degrees. A voltage of 20 V was applied to the device, and a dielectric constant ($\epsilon_\parallel$) in the major axis direction of liquid crystal molecules was measured. A voltage of 0.5 V was applied to the device, and a dielectric constant ($\epsilon_\perp$) in the minor axis direction of the liquid crystal molecules was measured. A value of dielectric anisotropy was calculated from an equation: $\Delta\epsilon = \epsilon_\parallel - \epsilon_\perp$.

(2) Composition having negative dielectric anisotropy: A sample was put in a liquid crystal cell subjected to treatment in homeotropic alignment, a voltage of 0.5 V was applied to the cell, and a dielectric constant ($\epsilon_\parallel$) was measured. A sample was put in a liquid crystal cell subjected to treatment in homogeneous alignment, a voltage of 0.5 V was applied to the cell, and a dielectric constant ($\epsilon_\perp$) was measured. A value of dielectric anisotropy was calculated from an equation: $\Delta\epsilon = \epsilon_\parallel - \epsilon_\perp$.

1-17 Threshold Voltage (Vth; Measured at 25° C.; V)

(1) Composition having positive dielectric anisotropy: A sample was put in a normally white mode liquid crystal display device in which a distance (gap) between two glass substrates (cell gap) was ($0.5/\Delta n$) micrometers and a twist angle was 80 degrees. Here, $\Delta n$ is a value of refractive index anisotropy measured according to the method described above. Rectangular waves having a frequency of 32 Hz were applied to the device. A voltage of rectangular waves was increased, and a value of voltage at 90% transmittance of light transmitted through the device was measured.

(2) Composition having negative dielectric anisotropy: A sample was put in a normally black mode liquid crystal display device subjected to treatment in homeotropic alignment in which a distance (gap) between two glass substrates (cell gap) was about 9 micrometers. Rectangular waves having a frequency of 32 Hz were applied to the device. A voltage of rectangular waves was increased, and a value of voltage at 10% transmittance of light transmitted through the device was measured.

1-18 Voltage Holding Ratio (VHR; Measured at 25° C.; %)

A TN device used for measurement had a polyimide alignment film, and a distance (cell gap) between two glass substrates was 6 micrometers. A sample was put in the device, and then the device was sealed with an ultraviolet-polymerizable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was determined. Area B is an area without decay. A voltage holding ratio is a percentage of area A to area B.

1-19 Helical Pitch (Measured at 20° C.; μm)

For measuring a helical pitch, a Cano's wedge cell method was applied. A sample was injected into a Cano's wedge cell, and a gap between disclination lines (a; unit: μm) as observed from the cell was measured. The helical pitch (P) was calculated according to an equation: $P = 2 \times a \times \tan\theta$, in which $\theta$ is an angle between two glass plates in the wedge cell.

Alternatively, the pitch length was measured using selective reflection (Handbook of Liquid Crystals (Ekisho Binran in Japanese), page 196, issued in 2000, Maruzen Co., Ltd.). A relational expression: $\langle n \rangle p/\lambda = 1$ holds for selective reflection wavelength $\lambda$, in which $\langle n \rangle$ represents an average refractive index and is provided by the following expression: $\langle n \rangle = \{(n_\parallel^2 + n_\perp^2)/2\}^{1/2}$. The selective reflection wavelength was measured by a microspectrophotometer (trade name: MSV-350, JEOL Co., Ltd.). The pitch was determined by dividing the resulting reflection wavelength by the average refractive index.

The pitch of the cholesteric liquid crystal having the reflection wavelength in the region of the wavelength longer than the wavelength of visible light is proportional to the reciprocal number of the concentration of the chiral agent in the region in which the concentration of the chiral agent is low. Thus, the pitch lengths of the liquid crystals having the selective reflection wavelength in the visible light region were measured in several points, and the pitch was determined according to the linear extrapolation method.

A ratio (percentage) of the components or the liquid crystal compounds is expressed in terms of weight percent (%) based on the total weight of the liquid crystal compound. The composition is prepared by measuring weight of the components such as the liquid crystal compounds, and then mixing the components. Accordingly, calculation of weight percent of the components is easy.

Example 1

Synthesis of Compound (1-1-1-S1)

A compound (compound (1-1-1-S1)) represented by formula (1-1-1-S1) described below in which $R^{1a}$ is $C_4H_9$ and $X^{1a}$ is fluorine in formula (1-1-1) was prepared according to schemes described below.

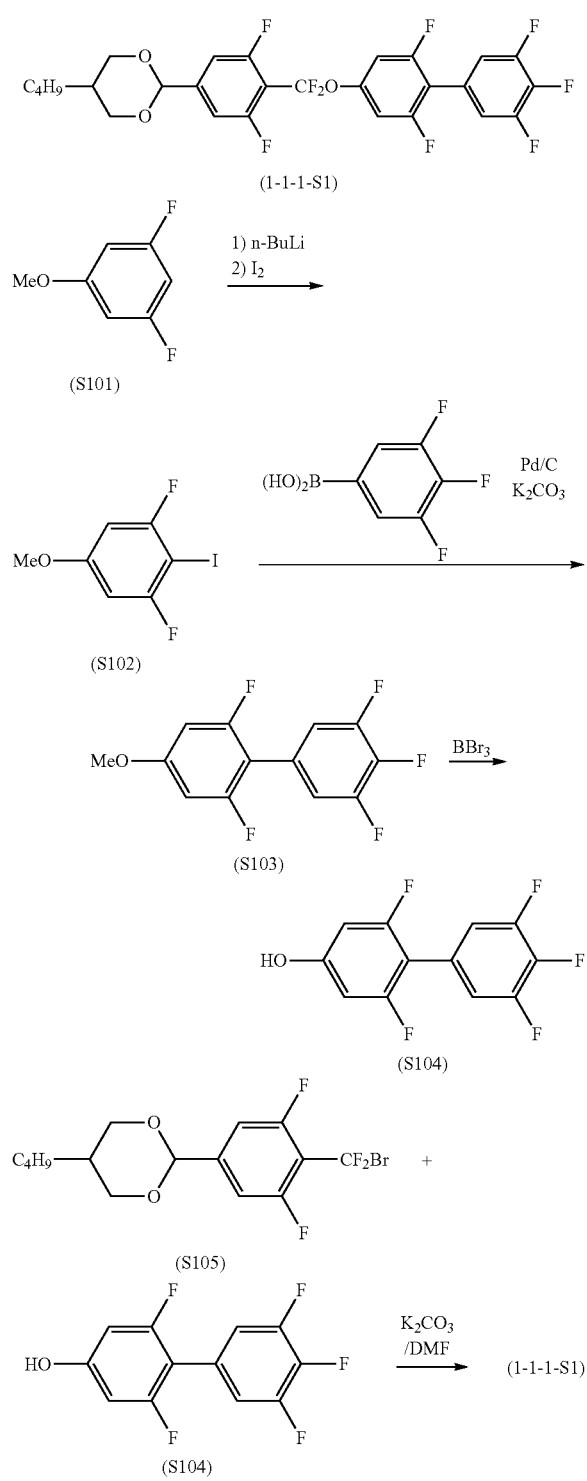

(First Step) Synthesis of Compound (S102)

Compound (S101) is commercially available. Under a nitrogen atmosphere, a THF (200 mL) solution of compound (S101) (38.4 g, 267 mmol) was cooled to −60° C., and then a n-butyllithium/hexane solution (1.66 M/L) (160 mL, 266 mmol) was slowly added dropwise thereto, and the resulting mixture was stirred at an indicated temperature for 1 hour. Subsequently, a THF (200 mL) solution of iodine (68.9 g, 266 mmol) was further added dropwise thereto, and the resulting mixture was stirred for 1 hour while the mixture was gradually returned to room temperature. The resulting reaction liquid was poured into water and subjected to extraction twice with toluene (500 mL), the resulting organic phase was washed twice with an aqueous solution of sodium thiosulfate and twice with water, and then the resulting organic phase was concentrated under reduced pressure. The resulting residue was purified by silica gel chromatography (solvent: n-heptane) to give compound (S102) (46.5 g, 172 mmol).

(Second Step) Synthesis of Compound (S103)

Under a nitrogen atmosphere, compound (S102) (46.5 g, 172 mmol) obtained in the above step, 3,4,5-trifluorophenylboronic acid (33.9 g, 193 mmol), potassium carbonate (72.8 g, 527 mmol), 5% palladium on carbon powder (3.00 g) and a mixed solution of toluene (100 mL)/ethanol (100 mL) were heated and stirred at 80° C. for 2 hours. To the resulting reaction liquid, toluene (300 mL) was added, the resulting organic phase was washed three times with water, and then the resulting organic phase was concentrated under reduced pressure. The resulting residue was purified by silica gel chromatography (solvent: n-heptane) and further purified by recrystallization (toluene/ethanol=5/1 in a volume ratio) and filtration to give compound (S103) (40.1 g, 146 mmol).

(Third Step) Synthesis of Compound (S104)

Under a nitrogen atmosphere, a dichloromethane (200 mL) solution of compound (S103) (40.1 g, 146 mmol) obtained in the above step was cooled to 0° C., and boron tribromide (43.8 g, 175 mmol) was added dropwise thereto, and the resulting mixture was stirred at an indicated temperature for 1 hour. The resulting reaction liquid was poured into water, dichloromethane (200 mL) was added thereto, and the resulting organic phase was washed three times with water, and then concentrated under reduced pressure. The resulting residue was purified by silica gel chromatography (solvent: toluene/ethyl acetate=2/1 in a volume ratio) and further purified by recrystallization (toluene/ethanol=5/1 in a volume ratio) and filtration to give compound (S104) (26.5 g, 102 mmol).

(Fourth Step) Synthesis of Compound (1-1-1-S1)

Compound (S105) can be obtained by a general technique in synthetic organic chemistry. Under a nitrogen atmosphere, compound (S105) (17.4 g (purity 74%), 33.3 mmol), compound (S104) (8.82 g, 33.9 mmol) obtained in the previous step, and a DMF (100 mL) solution of potassium carbonate (9.35 g, 67.7 mmol) were heated and stirred at 80° C. for 3 hours. The resulting reaction liquid was poured into water and subjected to extraction with toluene (200 mL), and the resulting organic phase was washed twice with sodium bicarbonate water and 3 times with water, and then concentrated under reduced pressure. The resulting residue was purified by silica gel chromatography (solvent: toluene/n-heptane=5/1 in a volume ratio) and further purified by recrystallization (ethanol/n-heptane=1/1 in a volume ratio) and filtration to give compound (1-1-1-S1) (6.98 g, 18.1 mmol) being a final objective product. A transition temperature of the compound was C 93.2 I.

$^1$H-NMR: δ (ppm)

0.910 (3H, t), 1.10-1.13 (2H, m), 1.25-1.35 (4H, m), 2.07-2.12 (1H, m), 3.50-3.55 (2H, dd), 4.23-4.26 (2H, dd), 5.37 (1H, s), 6.95-6.98 (2H, d), 7.08-7.11 (2H, d), 7.14-7.16 (2H, d)

$^{19}$F-NMR: δ (ppm)

−61.77--−61.88 (2F, t), −110.5--−110.6 (2F, dt), −112.7--−112.7 (2F, d), −134.8-134.9 (2H, dd), −160.4--−160.6 (1F, tt)

Next, the four compounds described as base liquid crystal A were mixed to prepare base liquid crystal A having a nematic phase. Properties of base liquid crystal A were as described below.

Maximum temperature $(T_{NI})$=71.7° C.; dielectric anisotropy $(\Delta\varepsilon)$=11.0; refractive index anisotropy $(\Delta n)$=0.137.

Liquid crystal composition AS1 formed of base liquid crystal A (90%) and compound (1-1-1-S1) (10%) obtained in Example 1 was prepared. Values of physical properties of the thus obtained liquid crystal composition AS1 were measured, and extrapolated values of physical properties of compound (1-1-1-S1) were calculated by extrapolation of the measured values. The values were as described below.

Maximum temperature $(T_{NI})$=46.7° C.; dielectric anisotropy $(\Delta\varepsilon)$=49.1; refractive index anisotropy $(\Delta n)$=0.117.

Accordingly, compound (1-1-1-S1) was found to have relatively excellent compatibility with other liquid crystal compounds and a large dielectric anisotropy $(\Delta\varepsilon)$.

Example 2

Preparation of Nematic Liquid Crystal Composition (NLC)

As shown in Table 1, nematic liquid crystal compositions NLC-A, NLC-B, NLC-C and NLC-D containing compound (1-1-1-S1) prepared in Example 1 were prepared (Table 1). Moreover, phase transition temperatures of each nematic liquid crystal composition were as shown in Table 2.

Table 1

TABLE 1

| Formulation of nematic liquid crystal composition | | | | | |
|---|---|---|---|---|---|
| | | | Formulation (% by weight) | | |
| | General formula | NLC-A | NLC-B | NLC-C | NLC-D |
| $C_6H_{13}$-[structure]-$CF_2O$-[structure]-F | (3-3) | 0.0 | 0.0 | 0.0 | 0.0 |
| $C_6H_{11}$-[structure]-$CF_2O$-[structure]-F | (3-3) | 3.0 | 3.0 | 4.0 | 2.2 |
| $C_4H_9$-[structure]-$CF_2O$-[structure]-F | (3-3) | 3.0 | 3.0 | 4.0 | 2.2 |
| $C_6H_{13}$-[structure]-$CF_2O$-[structure]-$CF_3$ | (3-3) | 4.0 | 4.0 | 5.0 | 3.6 |
| $C_6H_{11}$-[structure]-$CF_2O$-[structure]-$CF_3$ | (3-3) | 4.0 | 4.0 | 4.0 | 3.6 |
| $C_4H_9$-[structure]-$CF_2O$-[structure]-$CF_3$ | (3-3) | 3.5 | 4.0 | 4.0 | 3.6 |

TABLE 1-continued
Formulation of nematic liquid crystal composition
| | General formula | Formulation (% by weight) | | | |
|---|---|---|---|---|---|
| | | NLC-A | NLC-B | NLC-C | NLC-D |
| 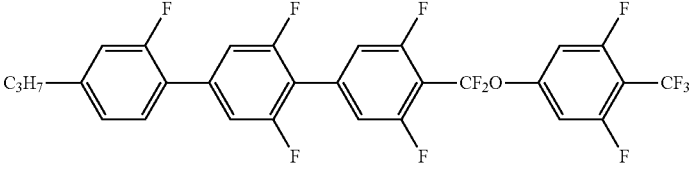 | (3-3) | 3.5 | 4.0 | 4.0 | 3.6 |
| 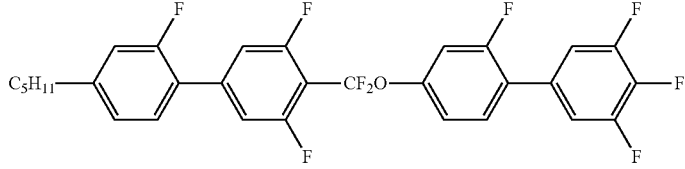 | (3-2) | 7.0 | 8.0 | 8.0 | 2.9 |
| 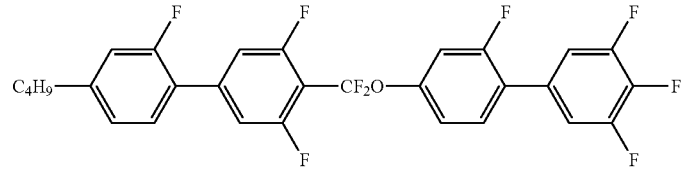 | (3-2) | 7.0 | 8.0 | 8.0 | 2.9 |
| 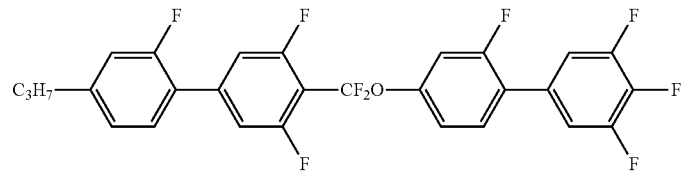 | (3-2) | 7.0 | 7.0 | 8.0 | 2.9 |
| 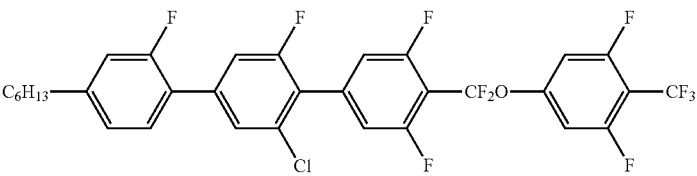 | (2-1-4-3) | 4.0 | 5.0 | 7.0 | 0.0 |
| 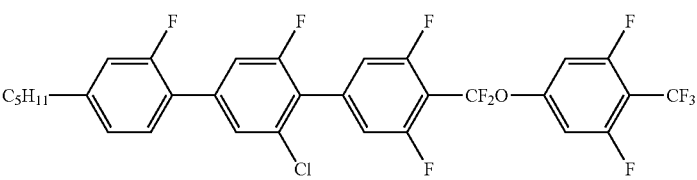 | (2-1-4-3) | 4.0 | 5.0 | 7.0 | 0.0 |
| 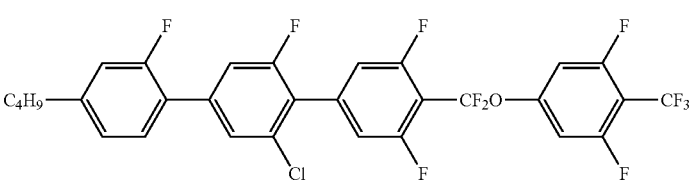 | (2-1-4-3) | 4.0 | 6.0 | 7.0 | 0.0 |
| 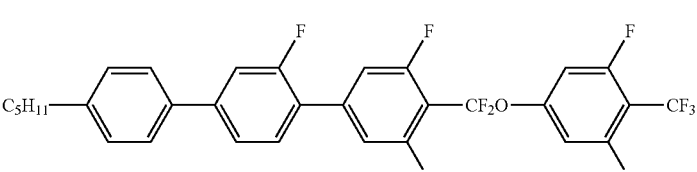 | (4-4) | 3.0 | 3.0 | 3.0 | 0.0 |

TABLE 1-continued
Formulation of nematic liquid crystal composition
| | General formula | Formulation (% by weight) | | | |
|---|---|---|---|---|---|
| | | NLC-A | NLC-B | NLC-C | NLC-D |
| 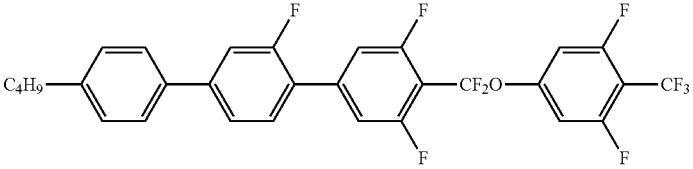 | (4-4) | 3.0 | 3.0 | 3.0 | 0.0 |
| 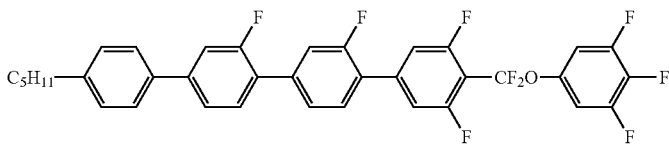 | (4-3) | 2.0 | 3.0 | 4.0 | 0.0 |
| 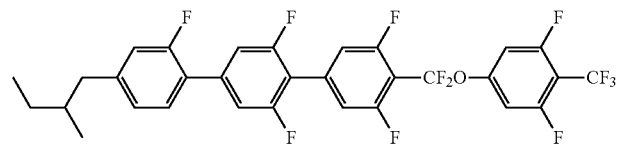 | (3-3) | 10.0 | 10.0 | 10.0 | 0.0 |
| 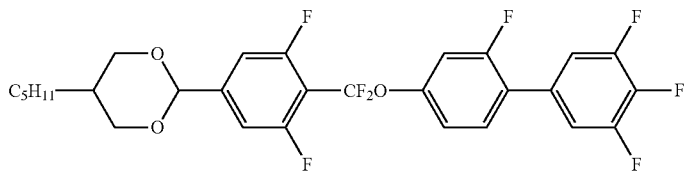 | (7-2-5-F) | 0.0 | 0.0 | 0.0 | 14.3 |
| 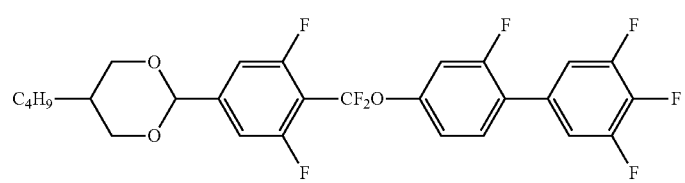 | (7-2-5-F) | 3.0 | 0.0 | 0.0 | 14.3 |
| 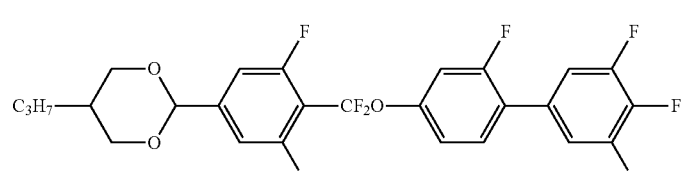 | (7-2-5-F) | 3.0 | 0.0 | 0.0 | 14.3 |
| 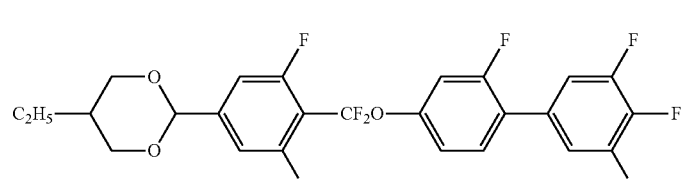 | (7-2-5-F) | 3.0 | 5.0 | 3.0 | 0.0 |
| 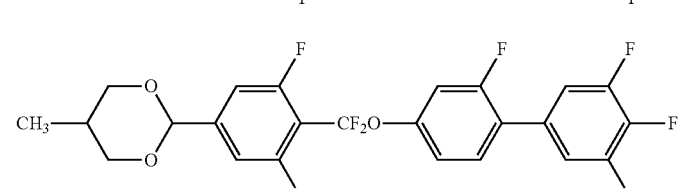 | (7-2-5-F) | 3.0 | 3.0 | 0.0 | 0.0 |

TABLE 1-continued

Formulation of nematic liquid crystal composition

| | General formula | Formulation (% by weight) | | | |
|---|---|---|---|---|---|
| | | NLC-A | NLC-B | NLC-C | NLC-D |
| 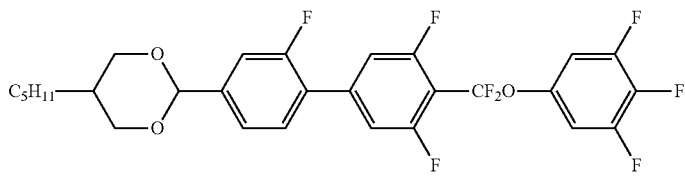 | (7-2-2-F) | 2.0 | 0.0 | 0.0 | 8.6 |
| 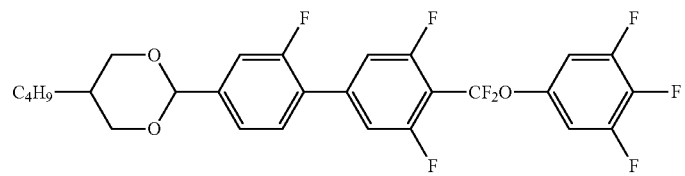 | (7-2-2-F) | 2.0 | 3.0 | 0.0 | 8.6 |
| 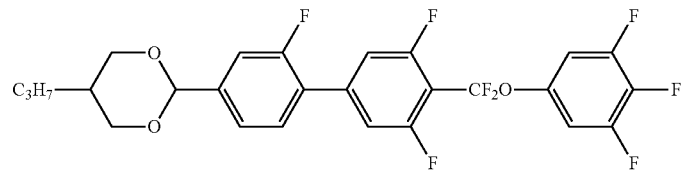 | (7-2-2-F) | 2.0 | 2.0 | 2.0 | 8.0 |
| 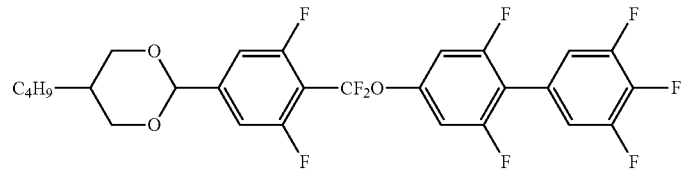 | (1-1-1) | 10.0 | 7.0 | 5.0 | 5.0 |

TABLE 2

| | Phase transition temperature/° C. |
|---|---|
| NLC-A | N 79.4 I |
| NLC-B | N 78.7 I |
| NLC-C | N 81.2 I |
| NLC-D | N 86.6 I |

Example 3

Preparation of Chiral Liquid Crystal Composition (CLC)

Next, chiral liquid crystal compositions CLC-A, CLC-B and CLC-C were prepared by mixing nematic liquid crystal compositions NLC-A, NLC-B and NLC-C shown in Table 1 with chiral agents BN-H4 and BN-H5 described below. Moreover, chiral liquid crystal composition CLC-D was prepared by mixing nematic liquid crystal composition NLC-D shown in Table 1 with chiral agent CD-5 described below. Formulations of the chiral liquid crystal compositions were as described below, and the phase transition temperatures were as shown in Table 3.

CLC-A

| NLC-A | 94.7% |
|---|---|
| BN-H4 | 2.65% |
| BN-H5 | 2.65% |

CLC-B

| NLC-B | 94.7% |
|---|---|
| BN-H4 | 2.65% |
| BN-H5 | 2.65% |

CLC-C

| NLC-C | 94.7% |
|---|---|
| BN-H4 | 2.65% |
| BN-H5 | 2.65% |

CLC-D

| NLC-D | 95.2% |
|---|---|
| CD-5 | 4.8% |

TABLE 3

| | Phase transition temperature/° C. |
|---|---|
| CLC-A | N* 68.2 BP 70.4 I |
| CLC-B | N* 67.6 BP 69.4 I |
| CLC-C | N* 69.3 BP ? I |
| CLC-D | N* 78.5 BP 80.1 I |

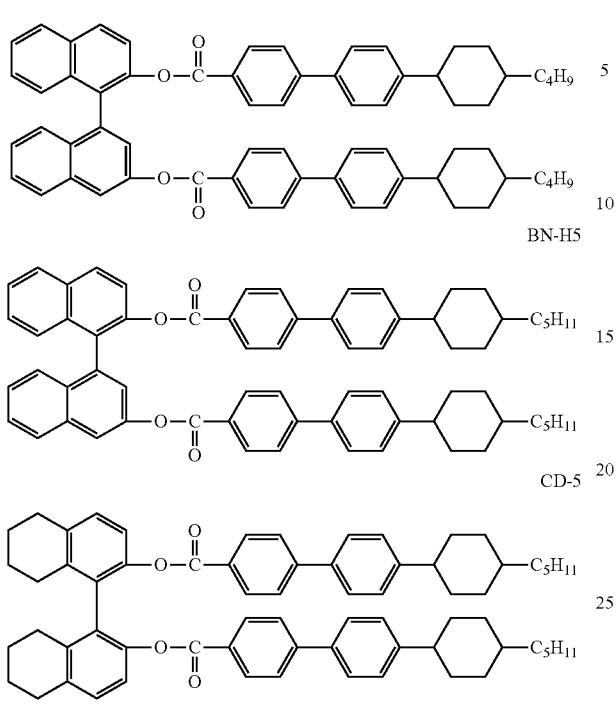

Example 4

Preparation of Liquid Crystal Composition (MLC) being Mixture with Polymerizable Monomer Liquid crystal compositions MLC-A, MLC-B, MLC-C and MLC-D were prepared by heating and mixing mixtures of chiral liquid crystal compositions (CLC) prepared in Example 3 with a polymerizable monomer in an isotropic phase. Formulations and phase transition of the liquid crystal compositions were as shown in Table 4.

| MLC-A | |
|---|---|
| CLC-A | 88.8% |
| n-hexadecyl acrylate | 6.0% |
| LCA-12 | 4.8% |
| DMPA | 0.4% |
| MLC-B | |
| CLC-B | 88.8% |
| n-hexadecyl acrylate | 6.0% |
| LCA-12 | 4.8% |
| DMPA | 0.4% |
| MLC-C | |
| CLC-C | 88.8% |
| n-hexadecyl acrylate | 6.0% |
| LCA-12 | 4.8% |
| DMPA | 0.4% |
| MLC-D | |
| CLC-D | 88.4% |
| n-hexadecyl acrylate | 6.2% |
| LCA-13 | 5.0% |
| DMPA | 0.4% |

Each of LCA-6, LCA-12 and DMPA described above represents 1,4-di(4-(6-(acryloyloxy)hexyloxy)benzoyloxy)-2-methylbenzene (LCA-6), 1,4-di(4-(6-(acryloyloxy)dodecyloxy)benzoyloxy)-2-methylbenzene (LCA-12) and 1,4-di(4-(6-(acryloyloxy)tridecyloxy)benzoyloxy)-2-methylbenzene (LCA-13) and 2,2'-dimethoxyphenylacetophenone, and DMP is a photopolymerization initiator.

TABLE 4

| | Phase transition temperature/° C. |
|---|---|
| MLC-A | N* 39.6 BP |
| MLC-B | N* 39.2 BP |
| MLC-C | N* 40.4 BP |
| MLC-D | N* 51.1 BP |

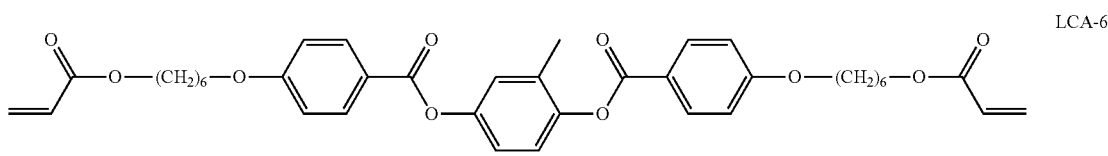

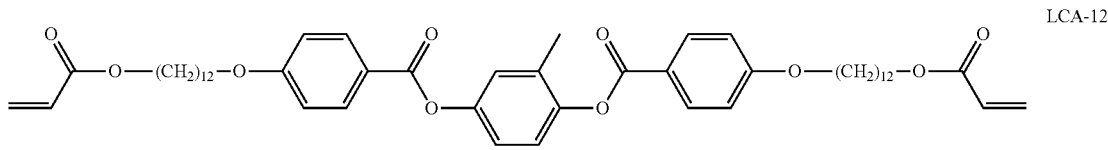

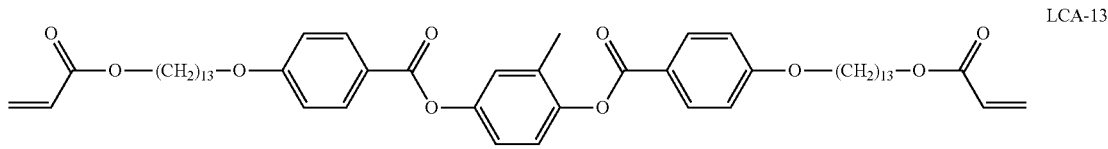

Example 5

Cell in which Polymer/Liquid Crystal Composite Material was Interposed

A liquid crystal composition (MLC) being a mixture of a chiral liquid crystal composition (CLC) and a polymerizable monomer was interposed between a comb-shaped electrode substrate subjected to no alignment treatment and a facing glass substrate (not provided with an electrode), and the resulting cell was heated to a blue phase. In the state, a polymerization reaction was performed by irradiating the resulting composition with ultraviolet light (intensity of ultraviolet light: 23 mWcm$^{-2}$ (365)) for 1 minute to prepare the cells in which polymer/liquid crystal composite materials PSBP-A, PSBP-B, PSBP-C and PSBP-D were interposed (cell thickness: 7 to 9 μm). Polymerization temperatures were as shown in Table 5.

TABLE 5

Polymerization temperatures for preparing polymer/liquid crystal composite material and resulting values of physical properties of polymer/liquid crystal composite material

|  | PSBP-A | PSBP-B | PSBP-C | PSBP-D |
|---|---|---|---|---|
| Kind of MLC used | MLC-A | MLC-B | MLC-C | MLC-D |
| Polymerization temperature (° C.) | 39.8 | 39.4 | 40.6 | 51.3 |
| Vmax(V) | 43 | 52 | 57 | 53 |
| Transmittance (%) during application of Vmax | 84 | 86 | 83 | 87 |
| Rise time (V10-90) (ms) | 1.2 | 1.2 | 1.0 | 1.2 |
| Fall time (V90-10) (ms) | 0.6 | 0.6 | 0.6 | 0.7 |

All of the thus obtained polymer/liquid crystal composite materials (PSBP) maintained the optically isotropic liquid crystal phase, even when the cells were cooled to room temperature.

Example 6

Optical System Using a Cell

Figure 2:
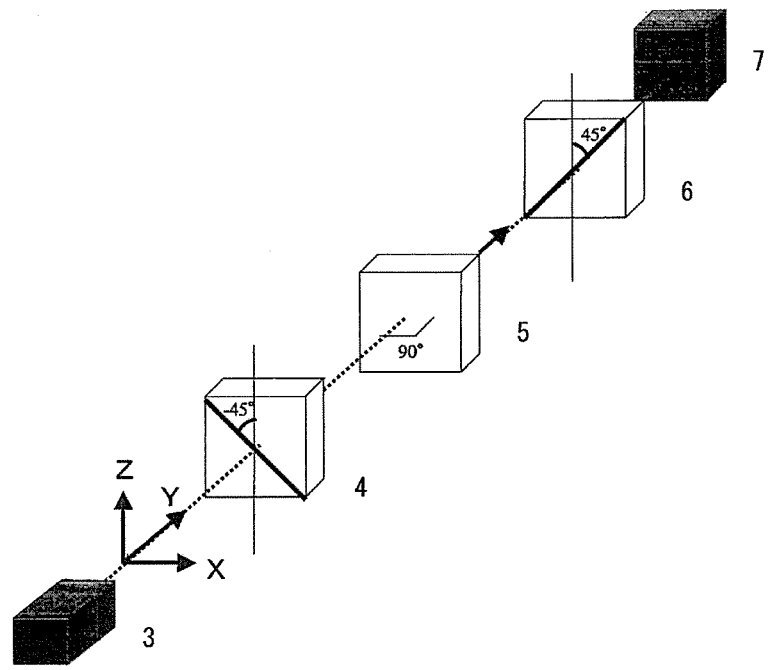
FIG. 2 shows an optical system used in Examples.

The cell in which the polymer/liquid crystal composite material was interposed therebetween as obtained in Example 5 was set to an optical system shown in FIG. 2. Specifically, as a light source 3, a white light source of a polarizing microscope (ECLIPSE LV100POL, made by Nikon Corporation) was used, and the cell in which the polymer/liquid crystal composite material was interposed therebetween as obtained in Example 5 was set such that an angle of incidence to the cell became perpendicular to a cell plane, and a line direction of the comb-shaped electrode 5 became 45 degrees relative to Polarizer 4 and Analyzer 6 polarizing plates, respectively. Photodetector 7 is a luminance meter, and used for measuring transmittance of the cell (FIG. 2).

A relationship between applied voltage and transmittance of the polymer/liquid crystal composite material obtained in Example 5 was investigated at room temperature. Values of physical properties of the polymer/liquid crystal composite materials (PSBP) interposed therebetween in the cells were as shown in Table 5. In addition, data of response time is obtained during saturated voltage application or during removal.

All of PSBP-A to PSBP-D showed a fast response in 2 milliseconds or less, and a high transmittance during saturated voltage application.

As is clear from the Examples described above, the optical device according to the invention has the short response time and the high transmittance, and therefore is superior to a conventional art.

INDUSTRIAL APPLICABILITY

Specific examples of utilization methods according to the invention include an optical device such as a display device using a polymer/liquid crystal composite.

What is claimed is:

1. A liquid crystal composition that contains achiral component T containing at least one compound 1 represented by formula (1), and a chiral agent, and develops an optically isotropic liquid crystal phase:

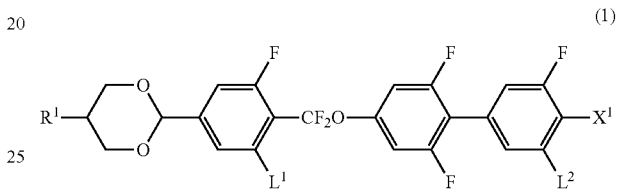

(1)

wherein, in formula (1), $R^1$ is hydrogen or alkyl having 1 to 20 carbons, at least one of —$CH_2$— in the alkyl may be replaced by —O—, —S—, —COO—, —OCO—, —CH═CH—, —CF═CF— or —C≡C—, at least one of hydrogen in the alkyl or in a group in which —$CH_2$— in the alkyl is replaced by —O—, —S—, —COO—, —OCO—, —CH═CH—, —CF═CF— or —C≡C— may be replaced by halogen or alkyl having 1 to 3 carbons; and $L^1$ and $L^2$ are each independently fluorine or hydrogen, and $X^1$ is halogen, —$CF_3$, —$OCF_3$, —C≡N or —N═C═S.

2. The liquid crystal composition according to claim 1, wherein compound 1 is a compound represented by formula (1-1):

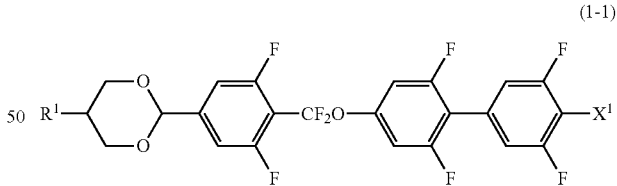

(1-1)

wherein, in formula (1-1), $R^1$ is hydrogen or alkyl having 1 to 20 carbons, at least one of —$CH_2$— in the alkyl may be replaced by —O—, —S—, —COO—, —OCO—, —CH═CH—, —CF═CF— or —C≡C—, at least one of hydrogen in the alkyl or in a group in which —$CH_2$— in the alkyl is replaced by —O—, —S—, —COO—, —OCO—, —CH═CH—, —CF═CF— or —C≡C— may be replaced by halogen or alkyl having 1 to 3 carbons; and $X^1$ is halogen, —$CF_3$, —$OCF_3$, —C≡N or —N═C═S.

3. The liquid crystal composition according to claim 1, wherein, in formula (1) or formula (1-1), $X^1$ is fluorine or —$CF_3$.

4. The liquid crystal composition according to claim 1, further containing at least one compound selected from the group of compound 3 represented by formula (3) and compound 7 represented by formula (7):

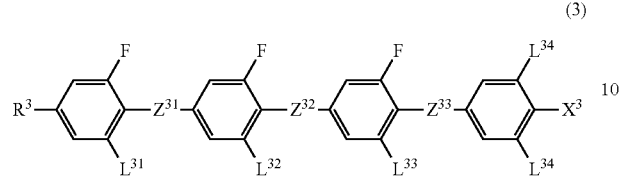

wherein, in formula (3), $R^3$ is hydrogen or alkyl having 1 to 20 carbons, at least one of —$CH_2$— in the alkyl may be replaced by —O—, —S—, —COO— or —OCO—, at least one of —$CH_2$—$CH_2$— in the alkyl or in a group in which at least one of —$CH_2$— in the alkyl is replaced by —O—, —S—, —COO— or —OCO— may be replaced by —CH=CH—, —CF=CF— or —C≡C—, at least one of hydrogen in the alkyl, in the group in which at least one of —$CH_2$— in the alkyl is replaced by —O—, —S—, —COO— or —OCO—, or in a group in which at least one of —$CH_2$—$CH_2$— in the group in which at least one of —$CH_2$— in the alkyl is replaced by —O—, —S—, —COO— or —OCO— may be replaced by fluorine or chlorine, in which, in $R^3$, neither —O— and —CH=CH— nor —CO— and —CH=CH— are adjacent;

$Z^{31}$, $Z^{32}$ and $Z^{33}$ are each independently a single bond, alkylene having 1 to 4 carbons, and at least one of —$CH_2$— in the alkylene may be replaced by —O—, —COO— or —$CF_2O$—;

$L^{31}$, $L^{32}$, $L^{33}$, $L^{34}$ and $L^{35}$ are each independently hydrogen or fluorine;

$X^3$ is hydrogen, halogen, —$SF_5$ or alkyl having 1 to 10 carbons, at least one of —$CH_2$— in the alkyl may be replaced by —O—, —S—, —COO— or —OCO—, at least one of —$CH_2$—$CH_2$— in the alkyl and in a group in which —$CH_2$— in the alkyl is replaced by —O—, —S—, —COO— or —OCO— may be replaced by —CH=CH—, —CF=CF— or —C≡C—, at least one of hydrogen in the alkyl, in the group in which —$CH_2$— in the alkyl is replaced by —O—, —S—, —COO— or —OCO—, and in a group in which at least one of —$CH_2$—$CH_2$— is replaced by —CH=CH— or —C≡C— may be replaced by fluorine or chlorine, in which, in $X^3$, neither —O— and —CH=CH— nor —CO— and —CH=CH— are adjacent:

wherein, in formula (7), $R^7$ is alkyl having 1 to 20 carbons, at least one of —$CH_2$— in the alkyl may be replaced by —O—, —S—, —COO— or —OCO—, at least one of —$CH_2$—$CH_2$— in the alkyl may be replaced by —CH=CH—, —CF=CF— or —C≡C—, at least one of hydrogen in the alkyl, in a group in which at least one of —$CH_2$— in the alkyl is replaced by —O—, —S—, —COO— or —OCO—, or in a group in which at least one of —$CH_2$—$CH_2$— in the group in which at least one of —$CH_2$— in the alkyl is replaced by —O—, —S—, —COO— or —OCO— is replaced by —CH=CH— or —C≡C— may be replaced by fluorine or chlorine, in which, in $R^7$, neither —O— and —CH=CH— nor —CO— and —CH=CH— are adjacent;

$L^{71}$, $L^{72}$, $L^{73}$, $L^{74}$, $L^{75}$, $L^{76}$, $L^{77}$ and $L^{78}$ are each independently hydrogen or fluorine;

$Z^{71}$, $Z^{72}$ and $Z^{73}$ are each independently a single bond, —COO— or —$CF_2O$—, but at least one of $Z^{71}$, $Z^{72}$ and $Z^{73}$ is —COO— or —$CF_2O$—;

n71 and n72 are each independently 0 or 1, and satisfies an expression: n71≥n72;

in which, when both $L^{71}$ and $L^{72}$ are fluorine, $Z^{71}$ is —$CF_2O$— and n71 is 1, $L^{74}$ is hydrogen, $X^7$ is hydrogen, halogen, —$SF_5$ or alkyl having 1 to 10 carbons, at least one of —$CH_2$— in the alkyl may be replaced by —O—, —S—, —COO— or —OCO—, at least one of —$CH_2$—$CH_2$— in the alkyl and in a group in which —$CH_2$— in the alkyl is replaced by —O—, —S—, —COO— or —OCO— may be replaced by —CH=CH—, —CF=CF— or —C≡C—, at least one of hydrogen in the alkyl, in the group in which —$CH_2$— in the alkyl is replaced by —O—, —S—, —COO— or —OCO—, or in the group in which at least one of —$CH_2$—$CH_2$— in the alkyl is replaced by —CH=CH— or —C≡C— may be replaced by fluorine or chlorine, in which, in $X^7$, neither —O— and —CH=CH— nor —CO— and —CH=CH— are adjacent.

5. The liquid crystal composition according to claim 1, containing at least one compound selected from the group represented by formulas (1) and (7) in an amount of 1 to 32% by weight based on the total weight of achiral component T.

6. The liquid crystal composition according to claim 4, wherein compound 3 is at least one selected from the group of compounds represented by formula (3-2) and formula (3-3):

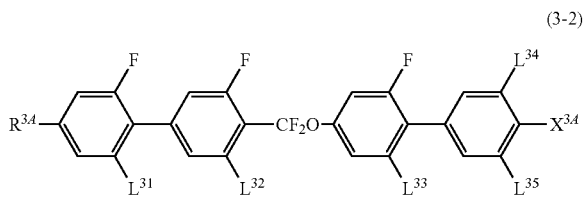

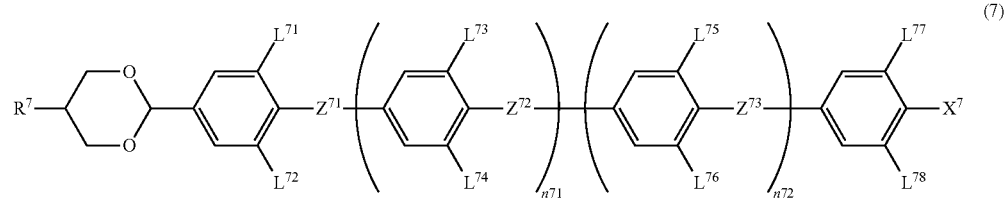

-continued (3-3)

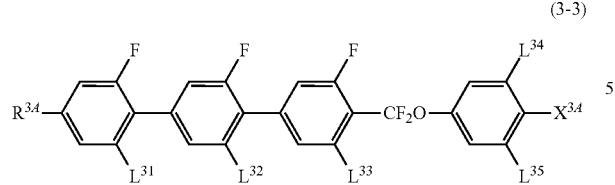

(wherein, $R^{3A}$ is each independently alkyl having 1 to 12 carbons, alkoxy having 1 to 12 carbons, alkenyl having 2 to 12 carbons, or alkenyl having 2 to 12 carbons in which at least one of hydrogen may be replaced by fluorine;

$L^{31}$, $L^{32}$, $L^{33}$, $L^{34}$ and $L^{35}$ are each independently hydrogen or fluorine; and $X^{3A}$ is fluorine, chlorine, —$CF_3$ or —$OCF_3$).

7. The liquid crystal composition according to claim 4, wherein compound 7 is at least one selected from the group of compounds represented by formulas (7-1) to (7-8):

(7-1)

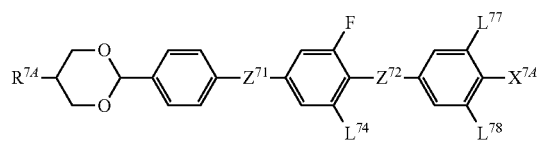

(7-2)

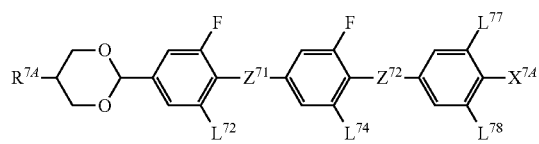

(7-3)

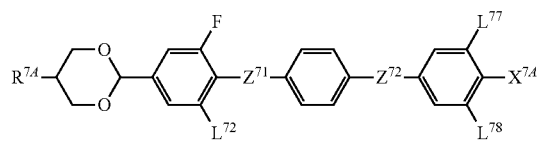

(7-4)

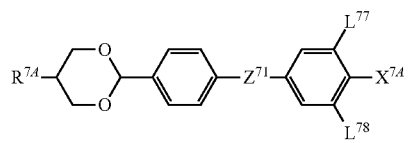

(7-5)

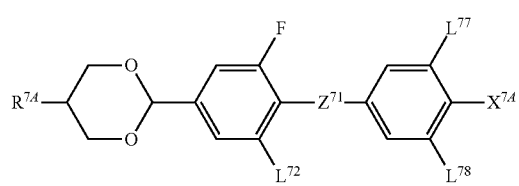

(7-6)

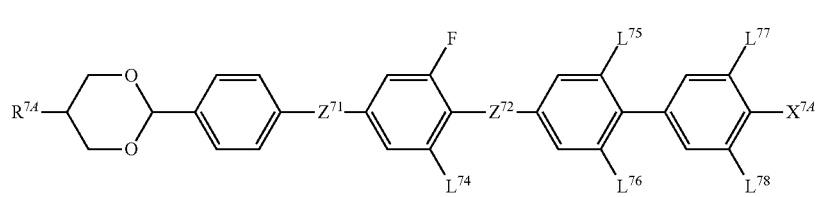

(7-7)

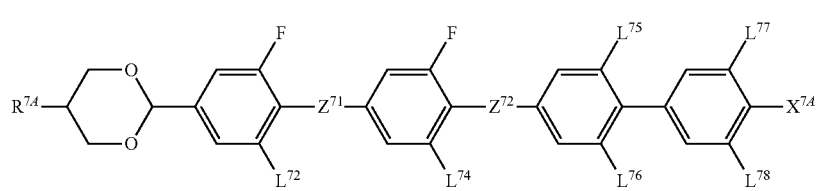

(7-8)

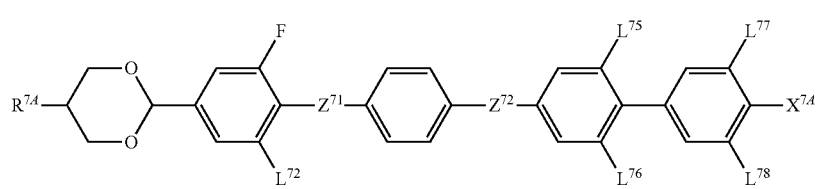

(wherein, $R^{74}$ is hydrogen, alkyl having 1 to 12 carbons, alkoxy having 1 to 11 carbons, alkenyl having 2 to 12 carbons, or alkenyl having 2 to 12 carbons in which at least one of hydrogen is replaced by fluorine;

$L^{72}$, $L^{74}$, $L^{75}$, $L^{76}$, $L^{77}$ and $L^{78}$ are each independently hydrogen or fluorine;

in formulas (7-1) to (7-3) and (7-6) to (7-8), $Z^{71}$ and $Z^{72}$ are each independently a single bond, —COO— or —CF$_2$O—, but at least one of $Z^{71}$ and $Z^{72}$ is —COO— or —CF$_2$O—, in which, in formula (7-3), when both $L^{71}$ and $L^{72}$ are fluorine, $Z^{71}$ is —CF$_2$O— and n71 is 1, $L^{74}$ is hydrogen, and in formulas (7-4) and (7-5), $Z^{71}$ is each independently —COO— or —CF$_2$O—, and $X^{74}$ is fluorine, chlorine, —CF$_3$ or —OCF$_3$).

8. The liquid crystal composition according to claim 4, wherein compound 7 is at least one selected from the group of compounds represented by formulas (7-2-2-E), (7-2-5-E), (7-2-2-F) and (7-2-5-F):

(7-2-2-E)

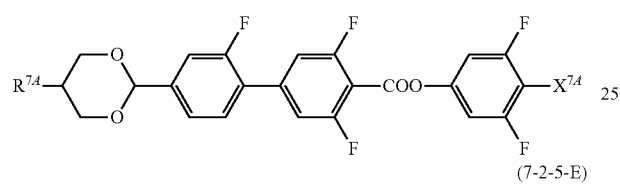

(7-2-5-E)

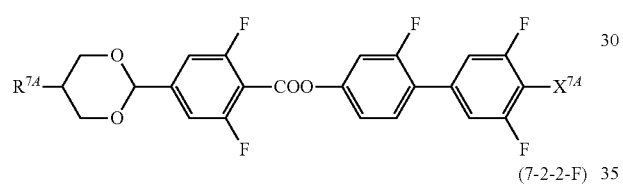

(7-2-2-F)

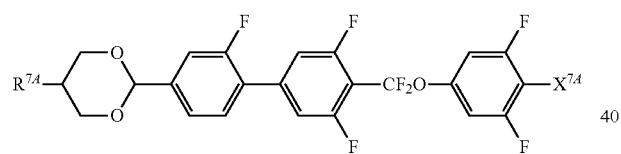

-continued (7-2-5-F)

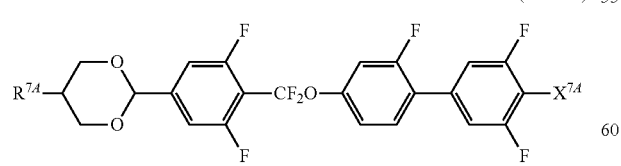

(wherein, $R^{74}$ is alkyl having 1 to 12 carbons, alkoxy having 1 to 11 carbons, alkenyl having 2 to 12 carbons, or alkenyl having 2 to 12 carbons in which at least one of hydrogen is replaced by fluorine; and $X^{74}$ is fluorine, chlorine, —CF$_3$ or —OCF$_3$).

9. The liquid crystal composition according to claim 4, containing compound 1 in a total amount of 3% by weight to 20% by weight, compound 3 in a total amount of 20% by weight to 80% by weight and compound 7 in a total amount of 10% by weight to 27% by weight, based on the total weight of achiral component T.

10. The liquid crystal composition according to claim 1, wherein achiral component T further contains at least one compound selected from the group of compounds of compound 4 represented by formula (4) and compound 2 represented by formula (2):

(4)

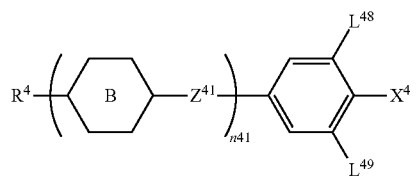

wherein, in formula (4), $R^4$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine;

ring B is each independently 1,4-cyclohexylene, 1,4-phenylene, 2-fluoro-1,4-phenylene, 3-fluoro-1,4-phenylene, 3,5-difluoro-1,4-phenylene, 3,5-dichloro-1,4-phenylene or pyrimidine 2,5-diyl;

$Z^{41}$ is each independently a single bond, ethylene, —COO—, —OCO—, —CF$_2$O— or —OCF$_2$—;

$L^{48}$ and $L^{49}$ are each independently hydrogen or fluorine;

$X^4$ is fluorine, chlorine, —CF$_3$ or —OCF$_3$; and n41 is 1, 2, 3 or 4, in which, when n41 is 3 or 4, at least one of $Z^{41}$ is —CF$_2$O— or —OCF$_2$—, and when n41 is 3, a case where all of ring B are 1,4-phenylene in which replacement by fluorine is caused is excluded;

(2)

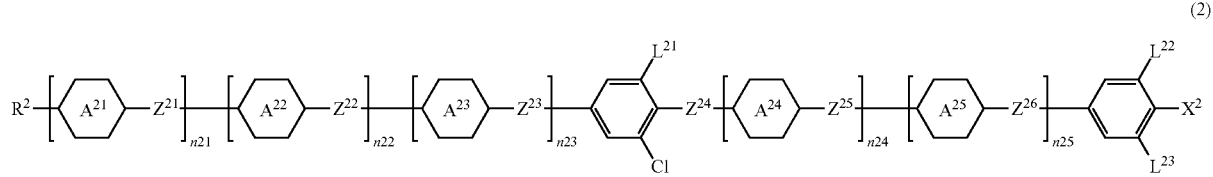

wherein, in formula (2), $R^2$ is hydrogen or alkyl having 1 to 20 carbons, at least one of —CH$_2$— in the alkyl may be replaced by —O—, —S—, —COO— or —OCO—, at least one of —CH$_2$—CH$_2$— in the alkyl may be replaced by —CH=CH—, —CF=CF— or —C≡C—, and at least one of hydrogen in the alkyl, in a group in which at least one of —CH$_2$— in the alkyl is replaced by —O—, —S—, —COO— or —OCO—, or in a group in which at least one of —CH$_2$—CH$_2$— in the group in which at least one of —CH$_2$— in the alkyl is replaced by —O—, —S—, —COO— or —OCO— is replaced by —CH=CH— or —C≡C— may be replaced by fluorine or chlorine, in which, in $R^2$, neither —O— and —CH=CH— nor —CO— and —CH=CH— are adjacent;

ring $A^{21}$, ring $A^{22}$, ring $A^{23}$, ring $A^{24}$ and ring $A^{25}$ are each independently 1,4-cyclohexylene, 1,3-dioxane-2,5-diyl, 1,4-phenylene, 1,4-phenylene in which one or two of hydrogen is replaced by fluorine, 1,4-phenylene in which two of hydrogen is replaced by fluorine and chlorine, respectively, pyridine-2,5-diyl and pyrimidine 2,5-diyl;

$Z^{21}$, $Z^{22}$, $Z^{23}$, $Z^{24}$, $Z^{25}$ and $Z^{26}$ are each independently a single bond or alkylene having 1 to 4 carbons, and at least one of —$CH_2$— in the alkylene may be replaced by —O—, —COO— or —$CF_2O$—;

$L^{21}$, $L^{22}$ and $L^{23}$ are each independently hydrogen or fluorine;

$X^2$ is fluorine, chlorine, —$CF_3$, —$CHF_2$, —$CH_2F$, —$OCF_3$, —$OCHF_2$, —$OCH_2F$, —$OCF_2CFHCF_3$ or —CH=$CHCF_3$; and n21, n22, n23, n24 and n25 are each independently 0 or 1, and satisfies an expression: $2 \leq n21+n22+n23+24+n25 \leq 3$.

11. The liquid crystal composition according to claim 10, wherein compound 4 is at least one selected from the group of compounds represented by formulas (4-1) to (4-9) and compound 2 is at least one selected from the group of compounds represented by formulas (2-1-1-2), (2-1-2-1), (2-1-3-1), (2-1-3-2), (2-1-4-2) and (2-1-4-3):

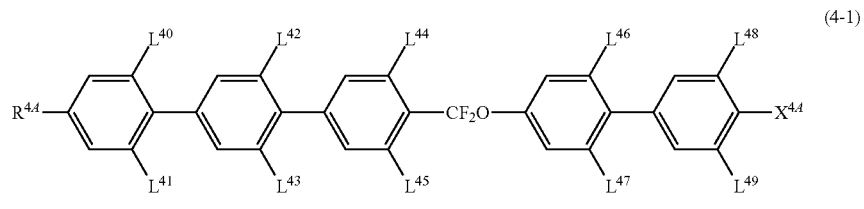

(4-1)

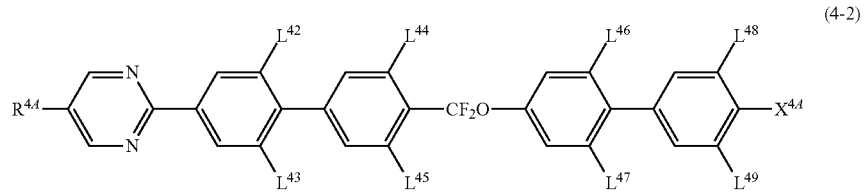

(4-2)

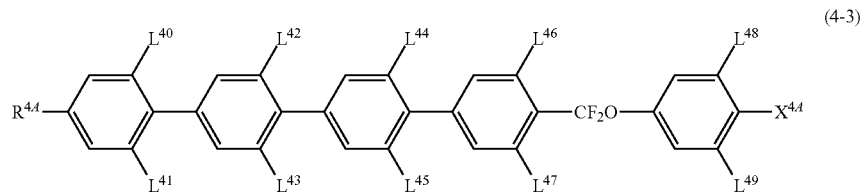

(4-3)

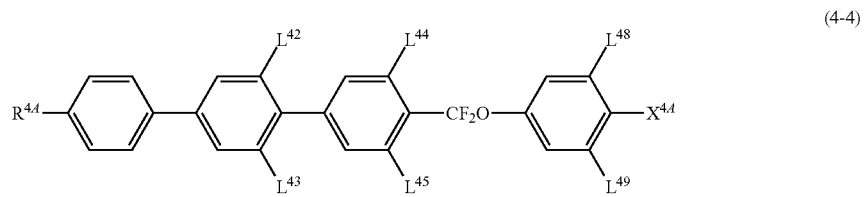

(4-4)

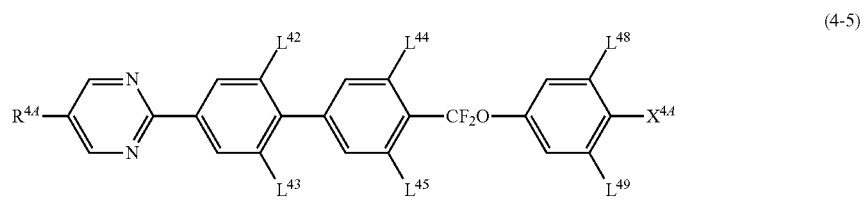

(4-5)

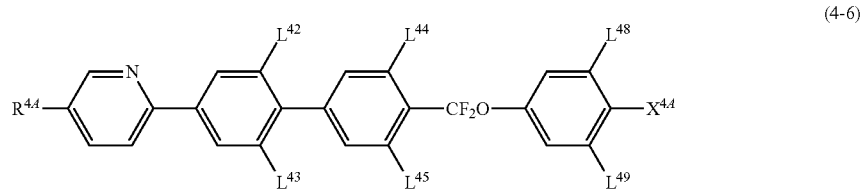

(4-6)

-continued
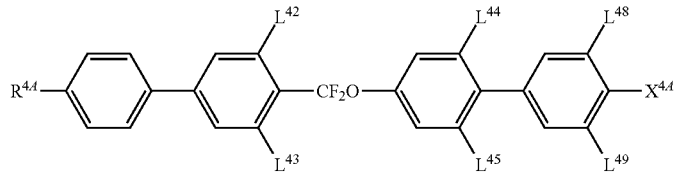
(4-7)
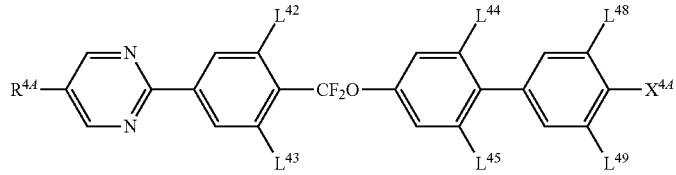
(4-8)
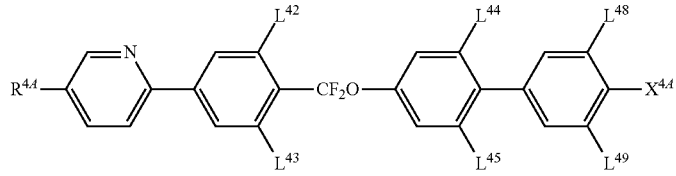
(4-9)
(wherein, $R^{4A}$ is each independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; $X^{4A}$ is fluorine, chlorine, —$CF_3$ or —$OCF_3$; and $L^{40}$ to $L^{49}$ are each independently hydrogen or fluorine;
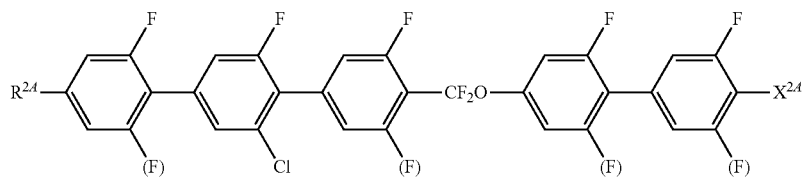
(2-1-1-2)
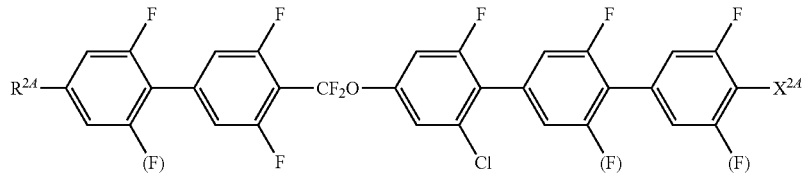
(2-1-2-1)
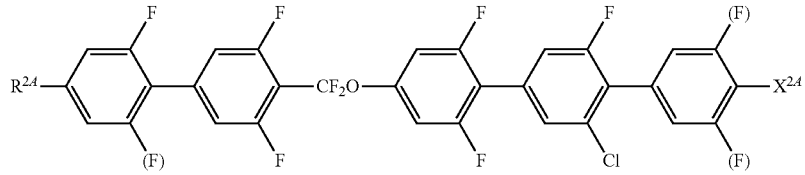
(2-1-3-1)
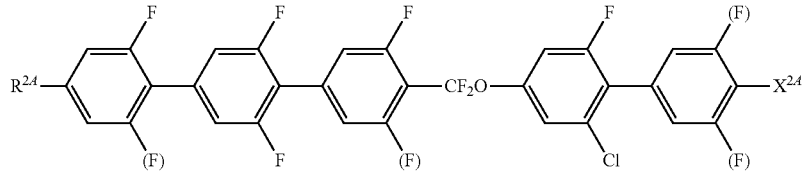
(2-1-3-2)

-continued

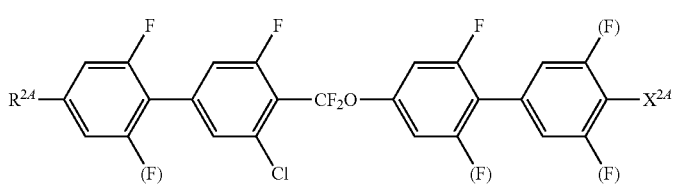
(2-1-4-2)

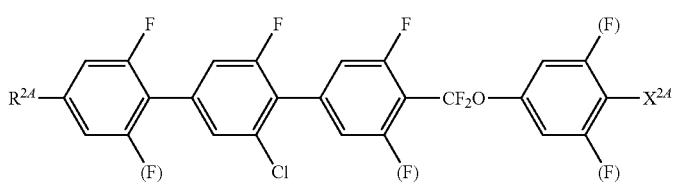
(2-1-4-3)

wherein, $R^{2A}$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine;

(F) is each independently hydrogen or fluorine; and $X^{2A}$ is fluorine, chlorine, —$CF_3$ or —$OCF_3$).

12. The liquid crystal composition according to claim 1, wherein the chiral agent is at least one compound selected from the group of compounds represented by formulas (K1) to (K6):

(K1)
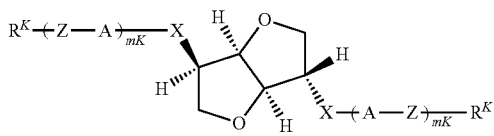

(K2)
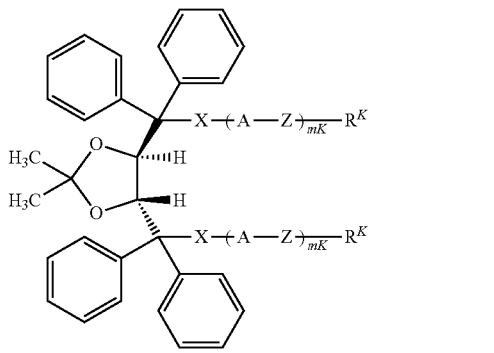

(K3)
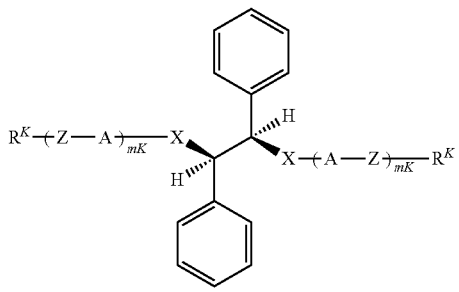

-continued (K4)
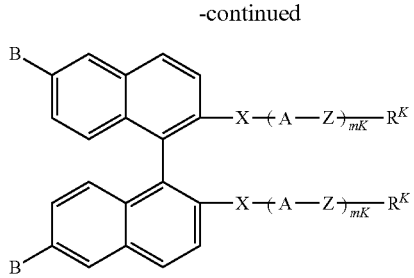

(K5)
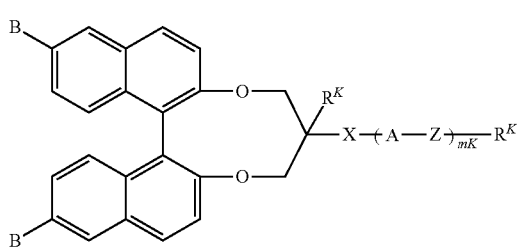

(K6)
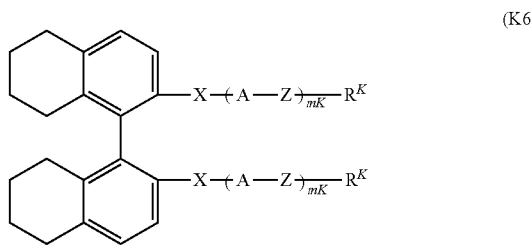

(wherein, $R^K$ is each independently hydrogen, halogen, —C≡N, —N=C=O, —N=C=S or alkyl having 1 to 20 carbons, at least one of —$CH_2$— in the $R^K$ may be replaced by —O—, —S—, —COO— or —OCO—, at least one of —$CH_2$—$CH_2$— in the $R^K$ may be replaced by —CH=CH—, —CF=CF— or —C≡C—, and at least one of hydrogen in the alkyl, in a group in which at least one of —$CH_2$— in the $R^K$ is replaced by —O—, —S—, —COO— or —OCO—, or in a group in which at least one of —$CH_2$—$CH_2$— in the $R^K$ is replaced by —CH=CH— or —C≡C— may be replaced by fluorine or chlorine;

A is each independently a 6- to 8-membered aromatic ring, a 3- to 8-membered non-aromatic ring or a condensed ring having 9 or more carbons, at least one of hydrogen in the rings may be replaced by halogen, alkyl or haloalkyl having 1 to 3 carbons, —$CH_2$— in the rings may be replaced by —O—, —S— or —NH—, and —CH═ may be replaced by —N═;

B is each independently hydrogen, halogen, alkyl having 1 to 3 carbons, haloalkyl having 1 to 3 carbons, a 6- to 8-membered aromatic ring, a 3- to 8-membered non-aromatic ring or a condensed ring having 9 or more carbons, at least one of hydrogen in the rings may be replaced by halogen, alkyl or haloalkyl having 1 to 3 carbons, —CH$_2$— in the rings may be replaced by —O—, —S— or —NH—, and —CH═ may be replaced by —N═;

Z is each independently a single bond, alkylene having 1 to 8 carbons, at least one of —CH$_2$— in the alkylene may be replaced by —O—, —S—, —COO—, —OCO—, —CSO—, —OCS—, —N═N—, —CH═N— or —N═CH—, at least one of —CH$_2$—CH$_2$— in the alkylene may be replaced by —CH═CH—, —CF═CF— or —C≡C—, and in the alkylene, at least one of hydrogen in a group in which at least one of —CH$_2$— in the alkylene is replaced by —O—, —S—, —COO— or —OCO—, or in a group in which at least one of —CH$_2$—CH$_2$— in the alkylene is replaced by —CH═CH—, —CF═CF— or —C≡C— may be replaced by halogen, X is each independently a single bond, —COO—, —OCO—, —CH$_2$O—, —OCH$_2$—, —CF$_2$O—, —OCF$_2$— or —CH$_2$CH$_2$—; and mK is each independently an integer from 1 to 4).

13. The liquid crystal composition according to claim 1, wherein a chiral nematic phase is exhibited in any temperature from −20° C. to −70° C., and a helical pitch is 700 nanometers or less in at least part of the temperature range.

14. A mixture, containing the liquid crystal composition according to claim 1 and a polymerizable monomer.

15. A polymer/liquid crystal composite material, obtained by polymerizing the mixture according to claim 14, and used in a device driven in an optically isotropic liquid crystal phase.

16. An optical device having electrodes arranged on one or both of substrates, a liquid crystal medium arranged between the substrates, and an electric field applying means for applying an electric field to the liquid crystal medium through the electrode, wherein the liquid crystal medium is the liquid crystal composition according to claim 1.

17. An optical device having electrodes arranged on one or both of substrates, a liquid crystal medium arranged between the substrates, and an electric field applying means for applying an electric field to the liquid crystal medium through the electrode, wherein the liquid crystal medium is the liquid crystal composition according to the polymer/liquid crystal composite material according to claim 15.

* * * * *